United States Patent [19]

Jacobs, Jr. et al.

[11] Patent Number: 5,686,590
[45] Date of Patent: Nov. 11, 1997

[54] METHODS AND COMPOSITIONS FOR DETECTING AND TREATING MYCOBACTERIAL INFECTIONS USING AN INHA GENE

[75] Inventors: William R. Jacobs, Jr., City Island, N.Y.; Desmond Michael Collins, Wellington, New Zealand; Asesh Banerjee, Bronx, N.Y.; Geoffrey William de Lisle, Upper Hutt; Theresa Mary Wilson, Wainuiomata, both of New Zealand

[73] Assignee: AgResearch, New Zealand Pastoral Agriculture Research Institute Ltd., Wellington, New Zealand

[21] Appl. No.: 241,766

[22] Filed: May 12, 1994

Related U.S. Application Data

[63] Continuation-in-part of Ser. No. 62,409, May 14, 1993, abandoned.

[51] Int. Cl.$^6$ .......................... C12N 15/00; C07H 21/04; C07K 14/00
[52] U.S. Cl. ..................... 536/23.1; 536/23.2; 536/23.7; 530/350; 530/825; 435/172.3
[58] Field of Search ............................. 536/23.1, 23.2, 536/23.7; 435/172.3

[56] References Cited

U.S. PATENT DOCUMENTS 5,573,915  11/1996  Barry .......................................... 435/6

OTHER PUBLICATIONS

Banerjee et al., "inhA, a gene encoding a target for isoniazid and ethionamide in *Mycobacterium tuberculosis*" *Science* (1994) 263:277–230.

Uhlmann et al., "Antisense oligonucleotides: A new therapeutic principle" *Chem. Reviews* (1990) 90(4):543–584.

Orita et al., "Rapid and sensitive detection of point mutations and DNA polymorphisms using the polymerase chain reaction" *Genomics* (1989) 5:874–879.

Telenti et al., "Rapid identification of Mycobacteria to the species level by polymerase chain reaction and restriction enzyme analysis" *J. Clin. Microbiol.* (1993) 31(2):175–178.

Zhang et al *Nature* 358 591–593, 1992.

*Primary Examiner*—Suzanne E. Ziska
*Attorney, Agent, or Firm*—Gladys H. Monroy

[57] ABSTRACT

The embodiments of the invention are based upon the identification and characterization of genes that determine mycobacterial resistance to the antibiotic isoniazid (INH) and its analogs. These genes, termed inhA, encode a polypeptide, InhA, that is the target of action of mycobacteria for isoniazid. The sequences of wild-type INH-sensitive as well as allelic or mutant INH-resistant inhA genes and their operons are provided. Also provided are isolated InhA polypeptides of both the INH-resistant and INH-sensitive types.

13 Claims, 28 Drawing Sheets

| PLASMID | DESCRIPTION | SOURCE OF INSERT | MIC (μg/ml) INH | MIC (μg/ml) ETH |
|---|---|---|---|---|
| pYUB18 | VECTOR | — | 5 | 20 |
| pYUB314 | pYUB18 :: *inhA* | *M. smegmatis*, $mc^2155$ | 60 | >80 |
| pYUB286 | pYUB18 :: *inhA* | *M. smegmatis*, $mc^2651$ | 60 | >80 |
| pYUB315 | pYUB18 :: *inhA* | *M. tuberculosis* | 15 | >30 |
| pYUB316 | pYUB18 :: *inhA* | *M. bovis* BCG | 15 | >30 |
| pYUB370 | pYUB18 :: *inhA* | *M. bovis* | 20 | >30 |
| pYUB317 | pYUB18 :: *inhA* | *M. avium* | 60 | >80 |

FIG. 1

```
 73 GGATCCGTC..ATGGTCGAAGTGTGCTGAGTCACACCGACAAACGTCACGAGCGTAACCCCA
    ||||||||   |||||||||||||||||||||||||||||||||||||||||||||||||
 73 GGATCCGTC..ATGGTCGAAGTGTGCTGAGTCACACCGACAAACGTCACGAGCGTAACCCCA
    ||||||| |  | ||  || |                                    ||||
  1 GGATCCGCCGCACGG.GGA.G............................... ...CCCC.

133 GTGCGAAAGTTCCCGCCGGAAATCGCAGCCACGTTACGCTCGTGGACATACCGATTTCGGCC
    |||||||||||||||||||||||||||||||||||||||||||||||||||||||||||||
133 GTGCGAAAGTTCCCGCCGGAAATCGCAGCCACGTTACGCTCGTGGACATACCGATTTCGGCC
         ||         ||                                ||||||| | |
 24 ....GA..........GG............................CGATTTCTGGC

195 CGGCCGCGGCGAGACGATAGGTTGTCGGG..................................
    ||||||||||||||||||||||||||||
195 CGGCCGCGGCGAGACGATAGGTTGTCGGG..................................
    || |  |  |  ||| || |||| ||||
 39 TGGACCGGCCAACACGTTAAGTTGACGGGCGAAGACGCAGGACGCGAGGAACAGAGGATGAC
                       RBS                         RBS        START

224 .GTGACTG.........CC.ACA...........GCCACTGAAGGGGCCAAACCCCCATTCG
     |||||||         ||.|||           |||||||||||||||||||||||||||
224 .GTGACTG.........CC.ACA...........GCCACTGAAGGGGCCAAACCCCCATTCG
     |||||||         || |||           ||||||| |||  || |  ||  ||||
101 TGTGACTGACAATCCGGCCGACACCGCGGGCGAGGCCACTGCAGG...CCGCCCGGCGTTCG
     START

264 TATCCCGTTCAGTCCTGGTTACCGGAGGAAACCGGGGGATCGGGCTGGCGATCGCACAGCGG
    |||||||||||||||||||||||||||||||||||||||||||||||||||||||||||||
264 TATCCCGTTCAGTCCTGGTTACCGGAGGAAACCGGGGGATCGGGCTGGCGATCGCACAGCGG
    | |||||||  |||||  ||||| |||||| || ||||| ||||||||||||||  |  ||
160 TCTCCCGTTCGGTGCTGGTGACCGGTGGTAACCGCGGCATCGGCCTGGCGATCGCGCGACGG

326 CTGGCTGCCGACGGCCACAAGGTGGCCGTCACCCACCGTGGATCCGGAGCGCCAAAGGGGCT
    |||||||||||||||||||||||||||||||||||||||||||||||||||||||||||||
326 CTGGCTGCCGACGGCCACAAGGTGGCCGTCACCCACCGTGGATCCGGAGCGCCAAAGGGGCT
    ||||| ||||||| ||||||||||||||||||||||| ||||||| || ||  |  |  ||
222 CTGGCCGCCGACGGGCACAAGGTGGCCGTCACCCACCGCGGTTCCGGTGCACCCGACGACCT

FIG. 2A
```

```
389 GTTTGGCGTCGAATGTGACGTCACCGACAGCGACGCCGTCGATCGCGCCTTCACGGCGGTAG
    |||||||||||||||||||||||||||||||||||||||||||||||||||||||||||||
389 GTTTGGCGTCGAATGTGACGTCACCGACAGCGACGCCGTCGATCGCGCCTTCACGGCGGTAG
    ||| || ||  |||||||||||||||||||| |  ||||| |||||||||| |  ||| |
284 GTTCGGTGTTCAATGTGACGTCACCGACAGCGCTGGTGTCGACCGCGCCTTCAAAGAGGTCG

451 AAGAGCACCAGGGTCCGGTCGAGGTGCTGGTGTCCAACGCCGGCCTATCCGCGGACGCATTC
    |||||||||||||||||||||||||||||||||||||||||||||||||||||||||||||
451 AAGAGCACCAGGGTCCGGTCGAGGTGCTGGTGTCCAACGCCGGCCTATCCGCGGACGCATTC
    |  ||||||||| |||||||||||||||||| ||||||| ||| ||| | |  |||||||
346 AGGAGCACCAGGGCCCGGTCGAGGTGCTGGTGGCCAACGCAGGCATCTCCAAGGACGCATTC

513 CTCATGCGGATGACCGAGGAAAAGTTCGAGAAGGTCATCAACGCCAACCTCACCGGGGCGTT
    |||||||||||||||||||||||||||||||||||||||||||||||||||||||||||||
513 CTCATGCGGATGACCGAGGAAAAGTTCGAGAAGGTCATCAACGCCAACCTCACCGGGGCGTT
    |||||||| |||||||||||   ||||||  |||||||||||  |||||||||||  |||||
408 CTCATGCGCATGACCGAGGAGCGGTTCGAAGAGGTCATCAACACCAACCTCACGGGCGCGTT

575 CCGGGTGGCTCAACGGGCATCGCGCAGCATGCAGCGCAACAAATTCGGTCGAATGATATTCA
    |||||||||||||||||||||||||||||||||||||||||||||||||||||||||||||
575 CCGGGTGGCTCAACGGGCATCGCGCAGCATGCAGCGCAACAAATTCGGTCGAATGATATTCA
    ||||   || || ||||| ||||||  ||||||||||||  |||||  ||  ||  || ||||
470 CCGGTGCGCCCAGCGGGCGTCGCGCACCATGCAGCGCAAGCGGTTCGGGCGCATCATCTTCA

637 TAGGTTCGGTCTCCGGCAGCTGGGGCATCGGCAACCAGGCCAACTACGCAGCCTCCAAGGCC
    |||||||||||||||||||||||||||||||||||||||||||||||||||||||||||||
637 TAGGTTCGGTCTCCGGCAGCTGGGGCATCGGCAACCAGGCCAACTACGCAGCCTCCAAGGCC
    | || ||||||||| ||||  |||||  |||||| |||||||||||||||  ||||||||
532 TCGGGTCGGTCTCGGGCATGTGGGGATCGGCAATCAGGCCAACTACGCGGCCGCCAAGGCG

699 GGAGTGATTGGCATGGCCCGCTCGATCGCCCGCGAGCTGTCGAAGGCAAACGTGACCGCGAA
    |||||||||||||||||||||||||||||||||||||||||||||||||||||||||||||
699 GGAGTGATTGGCATGGCCCGCTCGATCGCCCGCGAGCTGTCGAAGGCAAACGTGACCGCGAA
    || |||| ||||||||||||||||||| |||| ||||| ||||| |||   ||| ||||||||
594 GGCCTGATCGGCATGGCCCGCTCGATCTCCCGTGAGCTGGACAAGGCGGGCGTCACCGCGAA
```

FIG. 2B

```
761 TGTGGTGGCCCCGGGCTACATCGACACCGATATGACCCGCGCGCTGGATGAGCGGATTCAGC
    ||||||||||||||||||||||||||||||||||||||||||||||||||||||||||||||
761 TGTGGTGGCCCCGGGCTACATCGACACCGATATGACCCGCGCGCTGGATGAGCGGATTCAGC
    ||| || |||| || |||||||||||| |||||| ||||| || ||||| || |||
656 CGTGTTGCCCCCGGTTACATCGACACCGAGATGACCCGGGCGCTCGACGAGCGCATCCAGG

823 AGGGGGCGCTGCAATTTATCCCAGCGAAGCGGGTCGGCACCCCCGCCGAGGTCGCCGGGGTG
    |||||||||||||||||||||||||||||||||||||||||||||||||||||||||||||
823 AGGGGGCGCTGCAATTTATCCCAGCGAAGCGGGTCGGCACCCCCGCCGAGGTCGCCGGGGTG
    ||| ||| | |||| |||||| | |||||||||||||||||  || |||||||| || | |
718 GGGGCGCGATCGACTTCATCCCGGACAAGCGGGTCGGCACGGTCGAGGAGGTCGCGGGCGCG

885 GTCAGCTTCCTGGCTTCCGAGGATGCGAGCTATATCTCCGGTGCGGTCATCCCGGTCGACGG
    |||||||||||||||||||||||||||||||||||||||||||||||||||||||||||||
885 GTCAGCTTCCTGGCTTCCGAGGATGCGAGCTATATCTCCGGTGCGGTCATCCCGGTCGACGG
    ||||||||||||| ||||| || ||| ||| | |||||||||| |||||||||
780 GTCAGCTTCCTGGCCTCGGAGGACGCCTCCTACATCGCGGGCGCGGTCATCCCCGTCGACGG

947 CGGCATGGGTATGGGCCAC.............TGACACA..............ACACAAGGA
    |||||||||||||||||||          |||||||             ||||||||
947 CGGCATGGGTATGGGCCAC.............TGACACA..............ACACAAGGA
    ||| ||||| |||||||||                ||||||                ||||||||
842 CGGTATGGGCATGGGCCAC.TAGTCAAAAGCCCGGACACACAAGATTTCTCGCTCACAAGGA
                        STOP        STOP                        RBS

982 CGCAC...ATGACAGGACTGCTGGACGGCAAACGGATTCTGGTTAGCGGAATCATCACCGAC
    |||||   |||||||||||||||||||||||||||||||||||||||||||||||||||||
982 CGCAC...ATGACAGGACTGCTGGACGGCAAACGGATTCTGGTTAGCGGAATCATCACCGAC
    |||       |||||||||| || || |||| || || || || |   || |||||||||||
903 GTCACCAAATGACAGGACTACTCGAAGGCAAGCGCATCCTCGTCACGGGGATCATCACCGAT
            START

1041 TCGTCGATCGCGTTTCACATCGCACGGGTAGCCCAGGAGCAGGGCGCCCAGCTGGTGCTCAC
     |||||||||||||||||||||||||||||||||||||||||||||||||||||||||||||
1041 TCGTCGATCGCGTTTCACATCGCACGGGTAGCCCAGGAGCAGGGCGCCCAGCTGGTGCTCAC
     ||||||||||||| |||||||| ||||| |||||||| || ||| | |||||||| ||| ||
965  TCGTCGATCGCGTTCCACATCGCCAAGGTCGCCCAGGAGGCCGGTGCCGAACTGGTGCTGAC
```

FIG. 2C

```
1103 CGGGTTCGACCGGCTGCGGCTGATTCAGCGCATCACCGACCGGCTGCCGGCAAAGGCCCCGC
     ||||||||||||||||||||||||||||||||||||||||||||||||||||||||||||
1103 CGGGTTCGACCGGCTGCGGCTGATTCAGCGCATCACCGACCGGCTGCCGGCAAAGGCCCCGC
     |||  ||||||||  |||   |  |  |||||||||| |||||||| |||||        ||||||||
1027 CGGTTTCGACCGCCTGAAGTTGGTCAAGCGCATCGCCGACCGCCTGCCCAAGCCGGCCCCGC

1165 TGCTCGAACTCGACGTGCAAAACGAGGAGCACCTGGCCAGCTTGGCCGGCCGGGTGACCGAG
     ||||||||||||||||||||||||||||||||||||||||||||||||||||||||||||
1165 TGCTCGAACTCGACGTGCAAAACGAGGAGCACCTGGCCAGCTTGGCCGGCCGGGTGACCGAG
     ||||  ||||||||||||  ||||||||||||||  ||||||||  ||        ||||||  ||||  |  ||||
1089 TGCTGGAACTCGACGTGCAGAACGAGGAGCACCTGTCGACTCTGGCCGACCGGATCACCGCC

1227 GCGATCGGGGCGGGCAACAAGCTCGACGGGGTGGTGCATTCGATTGGGTTCATGCCGCAGAC
     ||||||||||||||||||||||||||||||||||||||  |||||||||||||||||||||||
1227 GCGATCGGGGCGGGCAACAAGCTCGACGGGGTGGTGCATGCGATTGGGTTCATGCCGCAGAC
     | ||||||  |  |||||||||||  |||||||  ||||||||  ||||  ||||||||||||||||
1151 GAGATCGGTGAGGGCAACAAGATCGACGGTGTGGTGCACTCGATCGGGTTCATGCCGCAGAG
                                              ↓
                                          G MUTATION IN mc² 651

1289 CGGGATGGGCATCAACCCGTTCTTCGACGCGCCCTACGCGGATGTGTCCAAGGGCATCCACA
     ||||||||||||||||||||||||||||||||||||||||||||||||||||||||||||
1289 CGGGATGGGCATCAACCCGTTCTTCGACGCGCCCTACGCGGATGTGTCCAAGGGCATCCACA
     |||  |||||||||||||||||||||||||||  ||||  ||||||||||||||||||||||||
1213 CGGTATGGGCATCAACCCGTTCTTCGACGCGCCGTACGAGGATGTGTCCAAGGGCATCCACA

1351 TCTCGGCGTATTCGTATGCTTCGATGGCCAAGGCGCTGCTGCCGATCATGAACCCCGGAGGT
     ||||||||||||||||||||||||||||||||||||||||||||||||||||||||||||
1351 TCTCGGCGTATTCGTATGCTTCGATGGCCAAGGCGCTGCTGCCGATCATGAACCCCGGAGGT
     ||||||||||  |||||  ||| |  ||||||  ||  |  ||||||||||||||  ||  |||
1275 TCTCGGCGTACTCGTACGCCTCGCTCGCCAAAGCCGTTCTGCCGATCATGAATCCGGGCGGT

1413 TCCATCGTCGGCATGGACTTCGACCCGAGCCGGGCGATGCCGGCCTACAACTGGATGACGGT
     ||||||||||||||||||||||||||||||||||||||||||||||||||||||||||||
1413 TCCATCGTCGGCATGGACTTCGACCCGAGCCGGGCGATGCCGGCCTACAACTGGATGACGGT
     ||||||||  |||||||||||||||  |  ||||||||||||||||||||||||||||||  ||
1337 GGTATCGTCGGTATGGACTTCGACCCCACGCGCGCGATGCCGGCCTACAACTGGATGACCGT
```

FIG. 2D

```
1475 CGCCAAGAGCGCGTTGGAGTCGGTCAACAGGTTCGTGGCGCGCGAGGCCGGCAAGTACGGTG
     |||||||||||||||||||||||||||||||||||||||||||||||||||||||||||||
1475 CGCCAAGAGCGCGTTGGAGTCGGTCAACAGGTTCGTGGCGCGCGAGGCCGGCAAGTACGGTG
     ||||||||||| | || ||||||||| |||||| ||||| ||||| ||||||      || |
1399 CGCCAAGAGCGCGCTCGAATCGGTCAACCGGTTCGTCGCGCGTGAGGCGGGCAAGGTGGGCG

1537 TGCGTTCGAATCTCGTTGCCGCAGGCCCTATCCGGACGCTGGCGATGAGTGCGATCGTCGGC
     |||||||||||||||||||||||||||||||||||||||||||||||||||||||||||||
1537 TGCGTTCGAATCTCGTTGCCGCAGGCCCTATCCGGACGCTGGCGATGAGTGCGATCGTCGGC
     |||| |||||||||||||| ||||| || ||||| ||||||||||||||| ||||| |||
1461 TGCGCTCGAATCTCGTTGCGGCAGGACCGATCCGCACGCTGGCGATGAGCGCAATCGTGGGC

1599 GGTGCGCTCGGCGAGGAGGCCGGCGCCCAGATCCAGCTGCTCGAGGAGGGCTGGGATCAGCG
     |||||||||||||||||||||||||||||||||||||||||||||||||||||||||||||
1599 GGTGCGCTCGGCGAGGAGGCCGGCGCCCAGATCCAGCTGCTCGAGGAGGGCTGGGATCAGCG
     ||||||||||||| |||||||||  |||| ||||||||||||||| |||||||||||||||
1523 GGTGCGCTGGGCGACGAGGCCGGCCAGCAGATGCAGCTGCTCGAAGAGGGCTGGGATCAGCG

1661 CGCTCCGATCGGCTGGAACATGAAGGATGCGACGCCGGTCGCCAAGACGGTGTGCGCGCTGC
     |||||||||||||||||||||||||||||||||||||||||||||||||||||||||||||
1661 CGCTCCGATCGGCTGGAACATGAAGGATGCGACGCCGGTCGCCAAGACGGTGTGCGCGCTGC
     ||| ||| | ||||||||||||||||||  ||||||| |||||||| |||||||| ||||
1585 CGCGCCGCTGGGCTGGAACATGAAGGACCCGACGCCCGTCGCCAAGACCGTGTGCGCACTGC

1723 TGTCTGACTGGCTGCCGGCGACCACGGGTGACATCATCTACGCCGACGGCGGCGCGCACACC
     |||||||||||||||||||||||||||||||||||||||||||||||||||||||||||||
1723 TGTCTGACTGGCTGCCGGCGACCACGGGTGACATCATCTACGCCGACGGCGGCGCGCACACC
     |||| ||||||||||||| ||||||||| |||  ||||||||||||||||||||| || |||
1647 TGTCGGACTGGCTGCCGGCCACCACCGGCACCGTGATCTACGCCGACGGCGGCGCCAGCACG

1785 CAATTGCTCTAGA    1796    M. tuberculosis H37Rv    wt    INHˢ
     |||||||||||||
1785 CAATTGCTCTAGA    1796    M. bovis NZ              mt    INHʳ
     || || | |
1709 CAGCTGTTGTGAT    1721    M. smegmatis mc²155      wt    INHˢ
                STOP
```

FIG. 2E

```
           10         20         30         40         50         60
MTGLLDGKRILVSGIITDSSIAFHIARVAQEQGAQLVLTGFDRLRLIQRITDRLPAKAPL
||||||||||||||||||||||||||||||||||||||||||||||||||||||||||||
MTGLLDGKRILVSGIITDSSIAFHIARVAQEQGAQLVLTGFDRLRLIQRITDRLPAKAPL
||||:|||||.|||||||||:|||.||:|||||||:|.||.|||| .|||
MTGLLEGKRILVTGIITDSSIAFHIAKVAQEAGAELVLTGFDRLKLVKRIADRLPKPAPL
||||||||||||||||||||||||||||||||||||||||||||||||||||||||||||
MTGLLEGKRILVTGIITDSSIAFHIAKVAQEAGAELVLTGFDRLKLVKRIADRLPKPAPL
| |:| ||||||:  ::  |||: ||:: : :|||||::|  :::  ||   |:::   :: ::
M-GFLSGKRILVTGVASKLSIAYGIAQAMHREGAELAFT-YQNDKLKGRVEEFAAQLGSS
| ||||||||||||||||||||||||||||||||||||| ||||||||||||||||||||
M-GFLSGKRILVTGVASKLSIAYGIAQAMHREGAELAFT-YQNDKLKGRVEEFAAQLGSD 70         80         90        100        110
LELDVQNEEHLASLAGRVTEAIGAGN-KLDGVVH [S] IGFMPQTGMGINPFFDAPY-ADV
|||||||||||||||||||||||||| |||||||  .  ||||||||||||||||||| |||
LELDVQNEEHLASLAGRVTEAIGAGN-KLDGVVH [A] IGFMPQTGMGINPFFDAPY-ADV
||||||||||||..|:|:|..||.|| |:||||||  .  ||||||.|||||||||||| .||
LELDVQNEEHLSTLADRITAEIGEGN-KIDGVVH [S] IGFMPQSGMGINPFFDAPY-EDV
|||||||||||||||||||||||||| |||||||    ||||||||||||||||||||  |||
LELDVQNEEHLSTLADRITAEIGEGN-KIDGVVH [A] IGFMPQSGMGINPFFDAPY-EDV
: | : :| |:   | :  |  ||:|:    |:|| ||  . ||| | ::: : :|   |:
IVLPCDVAEDASI--DAMFAELGNVWPKFDGFVH  S  IGFAPGDQLD-GDYVNAVTREGF
|||  |||||||||   | |||||||| ||||||||||  |  |||||||||||||||||||
IVLQCDVAEDASI--DTMFAELGKVWPKFDGFVH  S  IGFAPGDQLD-GDYVNAVTREGF 120        130        140        150        160        170
SKGIH-ISAYSYASMAKALL | PIMNPGGSIVGMDF-DPSRAMPAYNWMTVAK | SALESVN
||||| ||||||||||||||   ||||||||||||||| |||||||||||||||   |||||||
SKGIH-ISAYSYASMAKALL | PIMNPGGSIVGMDF-DPSRAMPAYNWMTVAK | SALESVN
||||| |||||||||:|||:   ||||||:|||||||  ||.||||||||||||   |||||||
SKGIH-ISAYSYASLAKAVL | PIMNPGGGIVGMDF-DPTRAMPAYNWMTVAK | SALESVN
||||| ||||||||||||||   |||||||||||||| ||||||||||||||||   |||||||
SKGIH-ISAYSYASLAKAVL | PIMNPGGGIVGMDF-DPTRAMPAYNWMTVAK | SALESVN
 |  | ||:||:::|||    :::|||:::::::  :::||:|:|:||   |:||   ::||:
-KVAHDISSYSFVAMAKACR   TMLNPGSALLTLSYLGAERAIPNYNVMGLAK   ASLEANV
| |||||||||||||||||||  ||||||||||||||||||||||||||||||||   |||||||
-KIAHDISSYSFVAMAKACR   SMLNPGSALLTLSYLGAERAIPNYNVMGLAK   ASLEANV
```

FIG. 4A

```
          180       190       200       210       220       230
RFVAREAGKYGVRSNLVGAGPIRTLAMSAIVGGALGEEAGAQIQLLEEGWDQRAPIGWNM
||||||||||||||||||||:||||||||||||||||||||||||||||||||||||||
RFVAREAGKYGVRSNLVAAGPIRTLAMSAIVGGALGEEAGAQIQLLEEGWDQRAPIGWNM
|||||||| |||||||||||||||||||||||:|||.|:|||||||||||||||:||||
RFVAREAGKVGVRSNLVAAGPIRTLAMSAIVGGALGDEAGQQMQLLEEGWDQRAPLGWNM
||||||||||||||||||||||||||||||||||||||||||||||||||||||||||
RFVAREAGKVGVRSNLVAAGPIRTLAMSAIVGGALGDEAGQQMQLLEEGWDQRAPLGWNM
|::|::  |   ||| |   ::|||||||   |:|
RYMANAMGPEGVRVNAISAGPIRTLAASGIKDFRKMLAHCEAVTPIRRTVTIEDVGNSAA
||||||||||||||||||||||||||||||||||||||||||||||||||||||||||
RYMANAMGPEGVRVNAISAGPIRTLAASGIKDFRKMLAHCEAVTPIRRTVTIEDVGNSAA
```

```
          240       250       260
KDATPVAKTVCALLSDWLPATTGDIIYADGGAHTQLL      M. tuberculosis         inhA
||||||||||||||||||||||||||||||||||||
KDATPVAKTVCALLSDWLPATTGDIIYADGGAHTQLL      M. bovis               inhA
||:||||||||||||||||||||||.:|||||| ||||
KDPTPVAKTVCALLSDWLPATTGTVIYADGGASTQLL      M. smegmatis, mc²155   inhA-1
|||||||||||||||||||||||||||||||||||||
KDPTPVAKTVCALLSDWLPATTGTVIYADGGASTQLL      M. smegmatis, mc²651   inhA-4

FLCSDLSAGISGEVVHVDGGFSIAAMNELELK           S. typhimurium         envM
|||||||||||||||||||||||||||||||
FLCSDLSAGISGEVVHVDGGFSIAAMNELELK           E. coli                envM
```

FIG. 4B

No. Transformants | Frequency of Cotransformation of
Kan$^r$    Kan$^r$ Inh$^s$ | Kan$^r$ with INH$^s$ 28      19            0.68

Sequence of M. smegmatis inhA gene

```
  1    GGATCCGCCG CACGGGGAGC CCCGAGGCGA TTTCTGGCTG GACCGGCCAA CACGTTAAGT
       CCTAGGCGGC GTGCCCCTCG GGGCTCCGCT AAAGACCGAC CTGGCCGGTT GTGCAATTCA

61    TGACGGGCGA AGACGCAGGA CGCGAGGAAC AGAGGATGAC TGTGACTGAC AATCCGGCCG
       ACTGCCCGCT TCTGCGTCCT GCGCTCCTTG TCTCCTACTG ACACTGACTG TTAGGCCGGC

121    ACACCGCGGG CGAGGCCACT GCAGGCCGCC CGGCGTTCGT CTCCCGTTCG GTGCTGGTGA
       TGTGGCGCCC GCTCCGGTGA CGTCCGGCGG GCCGCAAGCA GAGGGCAAGC CACGACCACT

181    CCGGTGGTAA CCGCGGCATC GGCCTGGCGA TCGCGCGACG GCTGGCCGCC GACGGGCACA
       GGCCACCATT GGCGCCGTAG CCGGACCGCT AGCGCGCTGC CGACCGGCGG CTGCCCGTGT

241    AGGTGGCCGT CACCCACCGC GGTTCCGGTG CACCCGACGA CCTGTTCGGT GTTCAATGTG
       TCCACCGGCA GTGGGTGGCG CCAAGGCCAC GTGGGCTGCT GGACAAGCCA CAAGTTACAC

301    ACGTCACCGA CAGCGCTGGT GTCGACCGCG CCTTCAAAGA GGTCGAGGAG CACCAGGGCC
       TGCAGTGGCT GTCGCGACCA CAGCTGGCGC GGAAGTTTCT CCAGCTCCTC GTGGTCCCGG

361    CGGTCGAGGT GCTGGTGGCC AACGCAGGCA TCTCCAAGGA CGCATTCCTC ATGCGCATGA
       GCCAGCTCCA CGACCACCGG TTGCGTCCGT AGAGGTTCCT GCGTAAGGAG TACGCGTACT

421    CCGAGGAGCG GTTCGAAGAG GTCATCAACA CCAACCTCAC GGGCGCGTTC CGGTGCGCCC
       GGCTCCTCGC CAAGCTTCTC CAGTAGTTGT GGTTGGAGTG CCCGCGCAAG GCCACGCGGG

481    AGCGGGCGTC GCGCACCATG CAGCGCAAGC GGTTCGGGCG CATCATCTTC ATCGGGTCGG
       TCGCCCGCAG CGCGTGGTAC GTCGCGTTCG CCAAGCCCGC GTAGTAGAAG TAGCCCAGCC

541    TCTCGGGCAT GTGGGGGATC GGCAATCAGG CCAACTACGC GGCCGCCAAG GCGGGCCTGA
       AGAGCCCGTA CACCCCCTAG CCGTTAGTCC GGTTGATGCG CCGGCGGTTC CGCCCGGACT

601    TCGGCATGGC CCGCTCGATC TCCCGTGAGC TGGACAAGGC GGGCGTCACC GCGAACGTGT
       AGCCGTACCG GGCGAGCTAG AGGGCACTCG ACCTGTTCCG CCCGCAGTGG CGCTTGCACA

661    TGCCCCCCGG TTACATCGAC ACCGAGATGA CCCGGGCGCT CGACGAGCGC ATCCAGGGGG
       ACGGGGGGCC AATGTAGCTG TGGCTCTACT GGGCCCGCGA GCTGCTCGCG TAGGTCCCCC

721    GCGCGATCGA CTTCATCCCG GACAAGCGGG TCGGCACGGT CGAGGAGGTC GCGGGCGCGG
       CGCGCTAGCT GAAGTAGGGC CTGTTCGCCC AGCCGTGCCA GCTCCTCCAG CGCCCGCGCC

781    TCAGCTTCCT GGCCTCGGAG GACGCCTCCT ACATCGCGGG GCGGGTCATC CCCGTCGACG
       AGTCGAAGGA CCGGAGCCTC CTGCGGAGGA TGTAGCGCCC CGCCAGTAG GGGCAGCTGC

841    GCGGTATGGG CATGGGCCAC TAGTCAAAAG CCCGGACACA CAAGATTTCT CGCTCACAAG
       CGCCATACCC GTACCCGGTG ATCAGTTTTC GGGCCTGTGT GTTCTAAAGA GCGAGTGTTC

901    GAGTCACCAA ATGACAGGCC TACTCGAAGG CAAGCGCATC CTCGTCACGG GGATCATCAC
       CTCAGTGGTT TACTGTCCGG ATGAGCTTCC GTTCGCGTAG GAGCAGTGCC CCTAGTAGTG
```

FIG. 7A

```
 961  CGATTCGTCG ATCGCGTTCC ACATCGCCAA GGTCGCCCAG GAGGCCGGCG CCGAACTGGT
      GCTAAGCAGC TAGCGCAAGG TGTAGCGGTT CCAGCGGGTC CTCCGGCCGC GGCTTGACCA

1021  GCTGACCGGT TTCGACCGCC TGAAGTTGGT CAAGCGCATC GCCGACCGCC TGCCCAAGCC
      CGACTGGCCA AAGCTGGCGG ACTTCAACCA GTTCGCGTAG CGGCTGGCGG ACGGGTTCGG

1081  GGCCCCGCTG CTGGAACTCG ACGTGCAGAA CGAGGAGCAC CTGTCGACTC TGGCCGACCG
      CCGGGGCGAC GACCTTGAGC TGCACGTCTT GCTCCTCGTG GACAGCTGAG ACCGGCTGGC

1141  GATCACCGCC GAGATCGGTG AGGGCAACAA GATCGACGGT GTGGTGCACG CGATCGGGTT
      CTAGTGGCGG CTCTAGCCAC TCCCGTTGTT CTAGCTGCCA CACCACGTGC GCTAGCCCAA

1201  CATGCCGCAG AGCGGTATGG GCATCAACCC GTTCTTCGAC GCGCCGTACG AGGATGTGTC
      GTACGGCGTC TCGCCATACC CGTAGTTGGG CAAGAAGCTG CGCGGCATGC TCCTACACAG

1261  CAAGGGCATC CACATCTCGG CGTACTCGTA CGCCTCGCTC GCCAAAGCCG TTCTGCCGAT
      GTTCCCGTAG GTGTAGAGCC GCATGAGCAT GCGGAGCGAG CGGTTTCGGC AAGACGGCTA

1321  CATGAATCCG GCGGCGGCA TCGTCGGCAT GGACTTCGAC CCCACGCGCG CGATGCCGGC
      GTACTTAGGC CCGCCGCCGT AGCAGCCGTA CCTGAAGCTG GGGTGCGCGC GCTACGGCCG

1381  CTACAACTGG ATGACCGTCG CCAAGAGCGC GCTCGAATCG GTCAACCGGT TCGTCGCGCG
      GATGTTGACC TACTGGCAGC GGTTCTCGCG CGAGCTTAGC CAGTTGGCCA AGCAGCGCGC

1441  TGAGGCGGGC AAGGTGGGCG TGCGCTCGAA TCTCGTTGCG GCAGGACCGA TCCGCACGCT
      ACTCCGCCCG TTCCACCCGC ACGCGAGCTT AGAGCAACGC CGTCCTGGCT AGGCGTGCGA

1501  GGCGATGAGC GCAATCGTGG GCGGTGCGCT GGGCGACGAG GCCGGCCAGC AGATGCAGCT
      CCGCTACTCG CGTTAGCACC CGCCACGCGA CCCGCTGCTC CGGCCGGTCG TCTACGTCGA

1561  GCTCGAAGAG GGCTGGGATC AGCGCGCGCC GCTGGGCTGG AACATGAAGG ACCCGACGCC
      CGAGCTTCTC CCGACCCTAG TCGCGCGCGG CGACCCGACC TTGTACTTCC TGGGCTGCGG

1621  CGTCGCCAAG ACCGTGTGCG CACTGCTGTC GGACTGGCTG CCGGCCACCA CCGGCACCGT
      GCAGCGGTTC TGGCACACGC GTGACGACAG CCTGACCGAC GGCCGGTGGT GGCCGTGGCA

1681  GATCTACGCC GACGGCGGCG CCAGCACGCA GCTGTTGTGA TACCGCCGTG TCGTATGACG
      CTAGATGCGG CTGCCGCCGC GGTCGTGCGT CGACAACACT ATGGCGGCAC AGCATACTGC

1741  CCTTGCTACT GCTGTCGTTC GACGGGCCGG AACTCCCGAG CAGGTGATGC CGTTCTTGGA
      GGAACGATGA CGACAGCAAG CTGCCCGGCC TTGAGGGCTC GTCCACTACG GCAAGAACCT

1801  GAACTCACCA GGGGCCGCGG AATCCCCAGG GAGCGGCTGG AATCGGTGGC CGAGCACTAT
      CTTGAGTGGT CCCCGGCGCC TTAGGGGTCC CTCGCCGACC TTAGCCACCG GCTCGTGATA

1861  CTGCACTTCG GCGGGGTGTC ACCGATCAAC GGCATCAACC GGGACCTGAT CGTCGCGATC
      GACGTGAAGC CGCCCCACAG TGGCTAGTTG CCGTAGTTGG CCCTGGACTA GCAGCGCTAG

1921  GAGGCCGAAC TCGCCCGACG CGGCCGCAAC CTTCCGGTCT ACTTCGGCAA CCGCAACTGG
      CTCCGGCTTG AGCGGGCTGC GCCGGCGTTG GAAGGCCAGA TGAAGCCGTT GGCGTTGACC
```

FIG. 7B

1981 GAGCCGTACG TCGAAGACAC TGTCAAGGCG ATGTCCGACA ACGGAATCCG TCGTGCGGCG
     CTCGGCATGC AGCTTCTGTG ACAGTTCCGC TACAGGCTGT TGCCTTAGGC AGCACGCCGC

2041 GTGTTCGCGA CCTCGGCGTG GGGTGGGTAC TCGGGATGCG CCCAGTACCA GGAGGACATC
     CACAAGCGCT GGAGCCGCAC CCCACCCATG AGCCCTACGC GGGTCATGGT CCTCCTGTAG

2101 GCGCGTGGCC GGGCCGCCGC CGGGCCCGAG GCGCCGGAGC TGGTCAAGCT GCGCCAGTAT
     CGCGCACCGG CCCGGCGGCG GCCCGGGCTC CGCGGCCTCG ACCAGTTCGA CGCGGTCATA

2161 TTCGACCACC CGCTGTTCGT CGAGATGTTC GCCGACGCCG TCGCCGACGC CGCGGCCACC
     AAGCTGGTGG GCGACAAGCA GCTCTACAAG CGGCTGCGGC AGCGGCTGCG GCGCCGGTGG

2221 CTGCCCGAGG AACTGCGGGA CGAAGCGCGG CTGGTGTTCA CCGCCCACTC CATCCCGCTG
     GACGGGCTCC TTGACGCCCT GCTTCGCGCC GACCACAAGT GGCGGGTGAG GTAGGGCGAC

2281 CGTGCCGCGT CGCGTTGCGG TGCAGATCTC TACGAGCGGC AGGTGGGTTA CGCCGCGCGG
     GCACGGCGCA GCGCAACGCC ACGTCTAGAG ATGCTCGCCG TCCACCCAAT GCGGCGCGCC

2341 CTGGTCGCGG CCGCAGCCGG GTACCGCGAA TACGACCAGG TATGGCAGTC CCGGTCCGGC
     GACCAGCGCC GGCGTCGGCC CATGGCGCTT ATGCTGGTCC ATACCGTCAG GGCCAGGCCG

2401 CCGCCGCAGG TGCCGTGGCT CGAACCCGAC GTCGGAGATC ACCTTGAGGC GTTGGCGCGC
     GGCGGCGTCC ACGGCACCGA GCTTGGGCTG CAGCCTCTAG TGGAACTCCG CAACCGCGCG

2461 AACGGCACCA GGGCGGTCAT CGTGTGTCCC CTCGGCTTCG TCGCCGACCA CATCGAGGTG
     TTGCCGTGGT CCCGCCAGTA GCACACAGGG GAGCCGAAGC AGCGGCTGGT GTAGCTCCAC

2521 GTGTGGGATC TGGACAACGA ACTGGCCGAG CAGGCCGCCG AGGCAGGCAT CGCGTTCGCG
     CACACCCTAG ACCTGTTGCT TGACCGGCTC GTCCGGCGGC TCCGTCCGTA GCGCAAGCGC

2581 CGTGCCGCCA CGCCCAACTC CCAGCCACGT TTTGCCCAAC TTGTCGTCGA CCTGATCGAC
     GCACGGCGGT GCGGGTTGAG GGTCGGTGCA AAACGGGTTG AACAGCAGCT GGACTAGCTG

2641 GAAATGCTGC ACGGACTTCC GCCACGCCGG GTCGAGGGGC CCGATCCGTG CCCGCCTACG
     CTTTACGACG TGCCTGAAGG CGGTGCGGCC CAGCTCCCCG GGCTAGGCAC GGGCGGATGC

2701 GCAGCAGTGT CAACGGCGCA CCGTGCACGC CGGCCTGCTC GGCGTGACCC GCCCCGGGCG
     CGTCGTCACA GTTGCCGCGT GGCACGTGCG GCCGGACGAG CCGCACTGGG CGGGGCCCGC

2761 CAGCGAGTCG GGCCGGGCGA TCAAGAACGC CAGGCGGAAT GCAGGATCGC CTCGAGTGCG
     GTCGCTCAGC CCGGCCCGCT AGTTCTTGCG GTCCGCCTTA CGTCCTAGCG GAGCTCACGC

2821 GCCATACGCG CCGAGCGCAC CACCCGCGTG AGGGGGCGCA GCGCCGAGTC GGCGATCTGA
     CGGTATGCGC GGCTCGCGTG GTGGGCGCAC TCCCCGCGT CGCGGCTCAG CCGCTAGACT

2881 ACCTCCGACG AACTCTGCAG ACCGCTCGGG ATCAGACCCG CACTCACCGC GATGATGGCG
     TGGAGGCTGC TTGAGACGTC TGGCGAGCCC TAGTCTGGGC GTGAGTGGCG CTACTACCGC

FIG. 7C

2941 TCGACATGGG CGGCGTTCTC CAGCACCCGC ACAGCCCGGG TCGGCGCGTG GTCGGGACG
     AGCTGTACCC GCCGCAAGAG GTCGTGGGCG TGTCGGGCCC AGCCGCGCAC CAGCCCCTGC

3001 CGGTGCGCGC GCCCGGCGGC GAGGATCTGC TCGACCATCC CGCGCGGATC C
     GCCACGCGCG CGGGCCGCCG CTCCTAGACG AGCTGGTAGG GCGCGCCTAG G

FIG. 7D

Sequence of the M. tuberculosis inhA gene

```
  1 AGCGCGACAT ACCTGCTGCG CAATTCGTAG GGCGTCAATA CACCCGCAGC CAGGGCCTCG
    TCGCGCTGTA TGGACGACGC GTTAAGCATC CCGCAGTTAT GTGGGCGTCG GTCCCGGAGC

61 CTGCCCAGAA AGGGATCCGT CATGGTCGAA GTGTGCTGAG TCACACCGAC AAACGTCACG
    GACGGGTCTT TCCCTAGGCA GTACCAGCTT CACACGACTC AGTGTGGCTG TTTGCAGTGC

121 AGCGTAACCC CAGTGCGAAA GTTCCCGCCG GAAATCGCAG CCACGTTACG CTCGTGGACA
    TCGCATTGGG GTCACGCTTT CAAGGGCGGC CTTTAGCGTC GGTGCAATGC GAGCACCTGT

181 TACCGATTTC GGCCCGGCCG CGGCGAGACG ATAGGTTGTC GGGGTGACTG CCACAGCCAC
    ATGGCTAAAG CCGGGCCGGC GCCGCTCTGC TATCCAACAG CCCCACTGAC GGTGTCGGTG

241 TGAAGGGGCC AAACCCCCAT TCGTATCCCG TTCAGTCCTG GTTACCGGAG GAAACCGGGG
    ACTTCCCCGG TTTGGGGGTA AGCATAGGGC AAGTCAGGAC CAATGGCCTC CTTTGGCCCC

301 GATCGGGCTG GCGATCGCAC AGCGGCTGGC TGCCGACGGC CACAAGGTGG CCGTCACCCA
    CTAGCCCGAC CGCTAGCGTG TCGCCGACCG ACGGCTGCCG GTGTTCCACC GGCAGTGGGT

361 CCGTGGATCC GGAGCGCCAA AGGGGCTGTT TGGCGTCGAA TGTGACGTCA CCGACAGCGA
    GGCACCTAGG CCTCGCGGTT TCCCCGACAA ACCGCAGCTT ACACTGCAGT GGCTGTCGCT

421 CGCCGTCGAT CGCGCCTTCA CGGCGGTAGA AGAGCACCAG GGTCCGGTCG AGGTGCTGGT
    GCGGCAGCTA GCGCGGAAGT GCCGCCATCT TCTCGTGGTC CCAGGCCAGC TCCACGACCA

481 GTCCAACGCC GGCCTATCCG CGGACGCATT CCTCATGCGG ATGACCGAGG AAAAGTTCGA
    CAGGTTGCGG CCGGATAGGC GCCTGCGTAA GGAGTACGCC TACTGGCTCC TTTTCAAGCT

541 GAAGGTCATC AACGCCAACC TCACCGGGGC GTTCCGGGTG GCTCAACGGG CATCGCGCAG
    CTTCCAGTAG TTGCGGTTGG AGTGGCCCCG CAAGGCCCAC CGAGTTGCCC GTAGCGCGTC

601 CATGCAGCGC AACAAATTCG GTCGAATGAT ATTCATAGGT TCGGTCTCCG GCAGCTGGGG
    GTACGTCGCG TTGTTTAAGC CAGCTTACTA TAAGTATCCA AGCCAGAGGC CGTCGACCCC

661 CATCGGCAAC CAGGCCAACT ACGCAGCCTC CAAGGCCGGA GTGATTGGCA TGGCCCGCTC
    GTAGCCGTTG GTCCGGTTGA TGCGTCGGAG GTTCCGGCCT CACTAACCGT ACCGGGCGAG

721 GATCGCCCGC GAGCTGTCGA AGGCAAACGT GACCGCGAAT GTGGTGGCCC CGGGCTACAT
    CTAGCGGGCG CTCGACAGCT TCCGTTTGCA CTGGCGCTTA CACCACCGGG GCCCGATGTA

781 CGACACCGAT ATGACCCGCG CGCTGGATGA GCGGATTCAG CAGGGGGCGC TGCAATTTAT
    GCTGTGGCTA TACTGGGCGC GCGACCTACT CGCCTAAGTC GTCCCCCGCG ACGTTAAATA

841 CCCAGCGAAG CGGGTCGGCA CCCCCGCCGA GGTCGCCGGG GTGGTCAGCT TCCTGGCTTC
    GGGTCGCTTC GCCCAGCCGT GGGGGCGGCT CCAGCGGCCC CACCAGTCGA AGGACCGAAG

901 CGAGGATGCG AGCTATATCT CCGGTGCGGT CATCCCGGTC GACGGCGGCA TGGGTATGGG
    GCTCCTACGC TCGATATAGA GGCCACGCCA GTAGGGCCAG CTGCCGCCGT ACCCATACCC
```

FIG. 8A

```
 961  CCACTGACAC AACACAAGGA CGCACATGAC AGGACTGCTG GACGGCAAAC GGATTCTGGT
      GGTGACTGTG TTGTGTTCCT GCGTGTACTG TCCTGACGAC CTGCCGTTTG CCTAAGACCA

1021  TAGCGGAATC ATCACCGACT CGTCGATCGC GTTTCACATC GCACGGGTAG CCCAGGAGCA
      ATCGCCTTAG TAGTGGCTGA GCAGCTAGCG CAAAGTGTAG CGTGCCCATC GGGTCCTCGT

1081  GGGCGCCCAG CTGGTGCTCA CCGGGTTCGA CCGGCTGCGG CTGATTCAGC GCATCACCGA
      CCCGCGGGTC GACCACGAGT GGCCCAAGCT GGCCGACGCC GACTAAGTCG CGTAGTGGCT

1141  CCGGCTGCCG GCAAAGGCCC CGCTGCTCGA ACTCGACGTG CAAAACGAGG AGCACCTGGC
      GGCCGACGGC CGTTTCCGGG GCGACGAGCT TGAGCTGCAC GTTTTGCTCC TCGTGGACCG

1201  CAGCTTGGCC GGCCGGGTGA CCGAGGCGAT CGGGGCGGGC AACAAGCTCG ACGGGGTGGT
      GTCGAACCGG CCGGCCCACT GGCTCCGCTA GCCCCGCCCG TTGTTCGAGC TGCCCCACCA

1261  GCATTCGATT GGGTTCATGC CGCAGACCGG GATGGGCATC AACCCGTTCT TCGACGCGCC
      CGTAAGCTAA CCCAAGTACG GCGTCTGGCC CTACCCGTAG TTGGGCAAGA AGCTGCGCGG

1321  CTACGCGGAT GTGTCCAAGG GCATCCACAT CTCGGCGTAT TCGTATGCTT CGATGGCCAA
      GATGCGCCTA CACAGGTTCC CGTAGGTGTA GAGCCGCATA AGCATACGAA GCTACCGGTT

1381  GGCGCTGCTG CCGATCATGA ACCCCGGAGG TTCCATCGTC GGCATGGACT TCGACCCGAG
      CCGCGACGAC GGCTAGTACT TGGGGCCTCC AAGGTAGCAG CCGTACCTGA AGCTGGGCTC

1441  CCGGGCGATG CCGGCCTACA ACTGGATGAC GGTCGCCAAG AGCGCGTTGG AGTCGGTCAA
      GGCCCGCTAC GGCCGGATGT TGACCTACTG CCAGCGGTTC TCGCGCAACC TCAGCCAGTT

1501  CAGGTTCGTG GCGCGCGAGG CCGGCAAGTA CGGTGTGCGT TCGAATCTCG TTGGCGCAGG
      GTCCAAGCAC CGCGCGCTCC GGCCGTTCAT GCCACACGCA AGCTTAGAGC AACCGCGTCC

1561  CCCTATCCGG ACGCTGGCGA TGAGTGCGAT CGTCGGCGGT GCGCTCGGCG AAGAGGCCGG
      GGGATAGGCC TGCGACCGCT ACTCACGCTA GCAGCCGCCA CGCGAGCCGC TTCTCCGGCC

1621  CGCCCAGATC CAGCTGCTCG AGGAGGGCTG GGATCAGCGC GCTCCGATCG GCTGGAACAT
      GCGGGTCTAG GTCGACGAGC TCCTCCCGAC CCTAGTCGCG CGAGGCTAGC CGACCTTGTA

1681  GAAGGATGCG ACGCCGGTCG CCAAGACGGT GTGCGCGCTG CTGTCTGACT GGCTGCCGGC
      CTTCCTACGC TGCGGCCAGC GGTTCTGCCA CACGCGCGAC GACAGACTGA CCGACGGCCG

1741  GACCACGGGT GACATCATCT ACGCCGACGG CGGCGCGCAC ACCCAATTGC TCTAGAACGC
      CTGGTGCCCA CTGTAGTAGA TGCGGCTGCC GCCGCGCGTG TGGGTTAACG AGATCTTGCG

1801  ATGCAATTTG ATGCCGTCCT GCTGCTGTCG TTCGGCGGAC CGGAAGGGCC CGAGCAGGTG
      TACGTTAAAC TACGGCAGGA CGACGACAGC AAGCCGCCTG GCCTTCCGG GCTCGTCCAC

1861  CGCCCGTTCC TGGAGAACGT TACCCGGGGC CGCGGTGTGC CTGCCGAACG GTTGGACGCG
      GCGGGCAAGG ACCTCTTGCA ATGGGCCCCG GCGCCACACG GACGGCTTGC CAACCTGCGC

1921  GTGGCCGAGC ACTACCTGCA TTTCGGTGGG GTATCACCGA TCAATGGCAT TAATCGCACA
      CACCGGCTCG TGATGGACGT AAAGCCACCC CATAGTGGCT AGTTACCGTA ATTAGCGTGT
```

FIG. 8B

```
1981  CTGATCGCGG AGCTGGAGGC GCAGCAAGAA CTGCCGGTGT ACTTCGGTAA CCGCAACTGG
      GACTAGCGCC TCGACCTCCG CGTCGTTCTT GACGGCCACA TGAAGCCATT GGCGTTGACC

2041  GAGCCGTATG TAGAAGATGC CGTTACGGCC ATGCGCGACA ACGGTGTCCG GCGTGCAGCG
      CTCGGCATAC ATCTTCTACG GCAATGCCGG TACGCGCTGT TGCCACAGGC CGCACGTCGC

2101  GTCTTTGCGA CATCTGCGTG GAGCGGTTAC TCGAGCTGCA CACAGTACGT GGAGGACATC
      CAGAAACGCT GTAGACGCAC CTCGCCAATG AGCTCGACGT GTGTCATGCA CCTCCTGTAG

2161  GCGCGGCCCC CCGCGCGGCC GGGCGCGACG CGCCTGAACT GGTAAAACTG CGGCCCTACT
      CGCGCCGGGG GGCGCGCCGG CCCGCGCTGC GCGGACTTGA CCATTTTGAC GCCGGGATGA

2221  TCGACCATCC GCTGTTCGTC GAGATGTTCG CCGACGCCAT CACCGCGGCC GCCGCAACCG
      AGCTGGTAGG CGACAAGCAG CTCTACAAGC GGCTGCGGTA GTGGCGCCGG CGGCGTTGGC

2281  TGCGCGGTGA TGCCCGGCTG GTGTTCACCG CGCATTCGAT CCCGACGGCC GCCGACCGCC
      ACGCGCCACT ACGGGCCGAC CACAAGTGGC GCGTAAGCTA GGGCTGCCGG CGGCTGGCGG

2341  GCTGTGGCCC CAACCTCTAC AGCCGCCAAG TCGCCTACGC CACAAGGCTG GTCGCGGCCG
      CGACACCGGG GTTGGAGATG TCGGCGGTTC AGCGGATGCG GTGTTCCGAC CAGCGCCGGC

2401  CTGCCGGATA CTGCGACTTT GACCTGGCCT GGCAGTCGAG ATCGGGCCCG CCGCAGGTGC
      GACGGCCTAT GACGCTGAAA CTGGACCGGA CCGTCAGCTC TAGCCCGGGC GGCGTCCACG

2461  CCTGGCTGGA GCCAGACGTT ACCGACCAGC TCACCGGTCT GGCTGGGGCC GGCATCAACG
      GGACCGACCT CGGTCTGCAA TGGCTGGTCG AGTGGCCAGA CCGACCCCGG CCGTAGTTGC
2521  CGGTGATCGT GTGTCCCATT GGATTCGTCG CCGACCATAT CGAGGTGGTG TGGGATCTCG
      GCCACTAGCA CACAGGGTAA CCTAAGCAGC GGCTGGTATA GCTCCACCAC ACCCTAGAGC

2581  ACCACGAGTT GCGATTACAA GCCGAGGCAG CGGGCATCGC GTACGCCCGG GCCAGCACCC
      TGGTGCTCAA CGCTAATGTT CGGCTCCGTC GCCCGTAGCG CATGCGGGCC CGGTCGTGGG

2641  CCAATGCCGA CCCGCGGTTC GCTCGACTAG CCAGAGGTTT GATCGACGAA CTCCGTTACG
      GGTTACGGCT GGGCGCCAAG CGAGCTGATC GGTCTCCAAA CTAGCTGCTT GAGGCAATGC

2701  GCCGTATACC TGCGCGGGTG AGTGGCCCCG ATCCGGTGCC GGGCTGTCTG TCCAGCATCA
      CGGCATATGG ACGCGCCCAC TCACCGGGGC TAGGCCACGG CCCGACAGAC AGGTCGTAGT

2761  ACGGCCAGCC ATGCCGTCCG CCGCACTGCG TGGCTAGCGT CAGTCCGGCC AGGCCGAGTG
      TGCCGGTCGG TACGGCAGGC GGCGTGACGC ACCGATCGCA GTCAGGCCGG TCCGGCTCAC

2821  CAGGATCGCC GTGACCGCGG ACATCCGGGC CGAGCGCACC ACGGCGGTCA ACGGTCTCAA
      GTCCTAGCGG CACTGGCGCC TGTAGGCCCG GCTCGCGTGG TGCCGCCAGT TGCCAGAGTT

2881  CGCATCGGTG GCACGCTGAG CGTCCGACAA CGACTGCGTT CCGATCGGCA ATCGACTCAG
      GCGTAGCCAC CGTGCGACTC GCAGGCTGTT GCTGACGCAA GGCTAGCCGT TAGCTGAGTC

2941  CCCGGCACTG ACCGCGATGA TCGCATCGAC GTGCGCGGCA TTCTCGAGCA CCCGCAATGC
      GGGCCGTGAC TGGCGCTACT AGCGTAGCTG CACGCGCCGT AAGAGCTCGT GGGCGTTACG
```

FIG. 8C

```
3001  GCGCGATGGC GCGTGGTCGG GAACCCGGTG TTGCCGTGAC GATTCGAGCA ACTGCTCGAC
      CGCGCTACCG CGCACCAGCC CTTGGGCCAC AACGGCACTG CTAAGCTCGT TGACGAGCTG

3061  GAGGCCACGG GGCTTGGCGA CGTCGCTAGA TCCCAGTCCG ATGGTGCTCA AGGCTTCGGC
      CTCCGGTGCC CCGAACCGCT GCAGCGATCT AGGGTCAGGC TACCACGAGT TCCGAAGCCG
```

FIG. 8D

Amino acid sequence of pS5

```
      GTTCGCTCCGGCGCGGTCACGCGCATGCCCTCGATGACGCAGATCTCGTCGGGCTCGATG
  1   ---------+---------+---------+---------+---------+---------+

CGCTCTTCCCAGACTTGCAGCCCCGGGGCACGGCGGCGGTTGGTGTCGATGATCGCGGCG
 61   ---------+---------+---------+---------+---------+---------+

GGAAGATCCGCGTCGATCCACTTGGCGCCATGGAAGGCAGAAGCCGAGTAGCCGGCCAGC
121   ---------+---------+---------+---------+---------+---------+

ACGCCGCGGCGGCGCGAGCGCAGCCACAGCGCTTTTGCACGCAATTGCGCGGTCAGTTCC
181   ---------+---------+---------+---------+---------+---------+

ACACCCTGCGGCACGTACACGTCTTTATGTAGCGCGACATACCTGCTGCGCAATTCGTAG
241   ---------+---------+---------+---------+---------+---------+

GGCGTCAATACACCCGCAGCCAGGGCCTCGCTGCCCAGAAAGGGATCCGTCATGGTCGAA
301   ---------+---------+---------+---------+---------+---------+

GTGTGCTGAGTCACACCGACAAACGTCACGAGCGTAACCCCAGTGCGAAAGTTCCCGCCG
361   ---------+---------+---------+---------+---------+---------+

GAAATCGCAGCCACGTTACGCTCGTGGACATACCGATTTCGGCCCGGCCGCGGCGAGACG
421   ---------+---------+---------+---------+---------+---------+

ATAGGTTGTCGGGGTGACTGCCACAGCCACTGAAGGGGCCAAACCCCCATTCGTATCCCG
481   ---------+---------+---------+---------+---------+---------+
                     V  T  A  T  A  E  G  A  K  P  P  F  V  S  R

TTCAGTCCTGGTTACCGGAGGAAACCGGGGGATCGGGCTGGCGATCGCACAGCGGCTGGC
541   ---------+---------+---------+---------+---------+---------+
       S  V  L  V  T  G  G  N  R  G  I  G  L  A  I  A  Q  R  L  A
```

FIG. 9A

```
        TGCCGACGGCCACAAGGTGGCCGTCACCCACCGTGGATCCGGAGCGCCAAAGGGGCTGTT
601     ---------+---------+---------+---------+---------+---------+
         A  D  G  H  K  V  A  V  T  H  R  G  S  G  A  P  K  G  L  F

TGGCGTCGAATGTGACGTCACCGACAGCGACGCCGTCGATCGCGCCTTCACGGCGGTAGA
661     ---------+---------+---------+---------+---------+---------+
         G  V  E  C  D  V  T  D  S  D  A  V  D  R  A  F  T  A  V  E

AGAGCACCAGGGTCCGGTCGAGGTGCTGGTGTCCAACGCCGGCCTATCCGCGGACGCATT
721     ---------+---------+---------+---------+---------+---------+
         E  H  Q  G  P  V  E  V  L  V  S  N  A  G  L  S  A  D  A  F

CCTCATGCGGATGACCGAGGAAAAGTTCGAGAAGGTCATCAACGCCAACCTCACCGGGGC
781     ---------+---------+---------+---------+---------+---------+
         L  M  R  M  T  E  E  K  F  E  K  V  I  N  A  N  L  T  G  A

GTTCCGGGTGGCTCAACGGGCATCGCGCAGCATGCAGCGCAACAAATTCGGTCGAATGAT
841     ---------+---------+---------+---------+---------+---------+
         F  R  V  A  Q  R  A  S  R  S  M  Q  R  N  K  F  G  R  M  I

ATTCATAGGTTCGGTCTCCGGCAGCTGGGGCATCGGCAACCAGGCCAACTACGCAGCCTC
901     ---------+---------+---------+---------+---------+---------+
         F  I  G  S  V  S  G  S  W  G  I  G  N  Q  A  N  Y  A  A  S

CAAGGCCGGAGTGATTGGCATGGCCCGCTCGATCGCCCGCGAGCTGTCGAAGGCAAACGT
961     ---------+---------+---------+---------+---------+---------+
         K  A  G  V  I  G  M  A  R  S  I  A  R  E  L  S  K  A  N  V

GACCGCGAATGTGGTGGCCCCGGGCTACATCGACACCGATATGACCCGCGCGCTGGATGA
1021    ---------+---------+---------+---------+---------+---------+
         T  A  N  V  V  A  P  G  Y  I  D  T  D  M  T  R  A  L  D  E

GCGGATTCAGCAGGGGGCGCTGCAATTTATCCCAGCGAAGCGGGTCGGCACCCCCGCCGA
1081    ---------+---------+---------+---------+---------+---------+
         R  I  Q  Q  G  A  L  Q  F  I  P  A  K  R  V  G  T  P  A  E
```

FIG. 9B

```
      GGTCGCCGGGGTGGTCAGCTTCCTGGCTTCCGAGGATGCGAGCTATATCTCCGGTGCGGT
1141  ---------+---------+---------+---------+---------+---------+
       V  A  G  V  V  S  F  L  A  S  E  D  A  S  Y  I  S  G  A  V

CATCCCGGTCGACGGCGGCATGGGTATGGGCCACTGACACAACACAAGGACGCACATGAC
1201  ---------+---------+---------+---------+---------+---------+
       I  P  V  D  G  G  M  G  M  G  H  *                    M  T

AGGACTGCTGGACGGCAAACGGATTCTGGTTAGCGGAATCATCACCGACTCGTCGATCGC
1261  ---------+---------+---------+---------+---------+---------+
       G  L  L  D  G  K  R  I  L  V  S  G  I  I  T  D  S  S  I  A

GTTTCACATCGCACGGGTAGCCCAGGAGCAGGGCGCCCAGCTGGTGCTCACCGGGTTCGA
1321  ---------+---------+---------+---------+---------+---------+
       F  H  I  A  R  V  A  Q  E  Q  G  A  Q  L  V  L  T  G  F  D

CCGGCTGCGGCTGATTCAGCGCATCACCGACCGGCTGCCGGCAAAGGCCCCGCTGCTCGA
1381  ---------+---------+---------+---------+---------+---------+
       R  L  R  L  I  Q  R  I  T  D  R  L  P  A  K  A  P  L  L  E

ACTCGACGTGCAAAACGAGGAGCACCTGGCCAGCTTGGCCGGCCGGGTGACCGAGGCGAT
1441  ---------+---------+---------+---------+---------+---------+
       L  D  V  Q  N  E  E  H  L  A  S  L  A  G  R  V  T  E  A  I

CGGGGCGGGCAACAAGCTCGACGGGGTGGTGCATGCGATTGGGTTCATGCCGCAGACCGG
1501  ---------+---------+---------+---------+---------+---------+
       G  A  G  N  K  L  D  G  V  V  H  A  I  G  F  M  P  Q  T  G

GATGGGCATCAACCCGTTCTTCGACGCGCCCTACGCGGATGTGTCCAAGGGCATCCACAT
1561  ---------+---------+---------+---------+---------+---------+
       M  G  I  N  P  F  F  D  A  P  Y  A  D  V  S  K  G  I  H  I

CTCGGCGTATTCGTATGCTTCGATGGCCAAGGCGCTGCTGCCGATCATGAACCCCGGAGG
1621  ---------+---------+---------+---------+---------+---------+
       S  A  Y  S  Y  A  S  M  A  K  A  L  L  P  I  M  N  P  G  G
```

FIG. 9C

```
      TTCCATCGTCGGCATGGACTTCGACCCGAGCCGGGCGATGCCGGCCTACAACTGGATGAC
1681  ---------+---------+---------+---------+---------+---------+
       S  I  V  G  M  D  F  D  P  S  R  A  M  P  A  Y  N  W  M  T

GGTCGCCAAGAGCGCGTTGGAGTCGGTCAACAGGTTCGTGGCGCGCGAGGCCGGCAAGTA
1741  ---------+---------+---------+---------+---------+---------+
       V  A  K  S  A  L  E  S  V  N  R  F  V  A  R  E  A  G  K  Y

CGGTGTGCGTTCGAATCTCGTTGCCGCAGGCCCTATCCGGACGCTGGCGATGAGTGCGAT
1801  ---------+---------+---------+---------+---------+---------+
       G  V  R  S  N  L  V  A  A  G  P  I  R  T  L  A  M  S  A  I

CGTCGGCGGTGCGCTCGGCGAGGAGGCCGGCGCCCAGATCCAGCTGCTCGAGGAGGGCTG
1861  ---------+---------+---------+---------+---------+---------+
       V  G  G  A  L  G  E  E  A  G  A  Q  I  Q  L  L  E  E  G  W

GGATCAGCGCGCTCCGATCGGCTGGAACATGAAGGATGCGACGCCGGTCGCCAAGACGGT
1921  ---------+---------+---------+---------+---------+---------+
       D  Q  R  A  P  I  G  W  N  M  K  D  A  T  P  V  A  K  T  V

GTGCGCGCTGCTGTCTGACTGGCTGCCGGCGACCACGGGTGACATCATCTACGCCGACGG
1981  ---------+---------+---------+---------+---------+---------+
       C  A  L  L  S  D  W  L  P  A  T  T  G  D  I  I  Y  A  D  G

CGGCGCGCACACCCAATTGCTCTAGAACGCATGCAATTTGATGCCGTCCTGCTGCTGTCG
2041  ---------+---------+---------+---------+---------+---------+
       G  A  H  T  Q  L  L  *

TTCGGCGGACCGGAAGGGCCCGAGCAGGTGCGGCCGTTCCTGGAGAACGTTACCCGGGGC
2101  ---------+---------+---------+---------+---------+---------+

CGCGGTGTGCCTGCCGAACGGTTGGACGCGGTGGCCGAGCACTACCTGCATTTCGGTGGG
2161  ---------+---------+---------+---------+---------+---------+

GTATCACCGATC
2221  ---------+--
```

FIG. 9D

Amino acid sequence of pS5 encoded by nucleic acid residues 1256-2062

```
MTGLLDGKRI  LVSGIITDSS  IAFHIARVAQ  EQGAQLVLTG  FDRLRLIQRI
TDRLPAKAPL  LELDVQNEEH  LASLAGRVTE  AIGAGNKLDG  VVHAIGFMPQ
TGMGINPFFD  APYADVSKGI  HISAYSYASM  AKALLPIMNP  GGSIVGMDFD
PSRAMPAYNW  MTVAKSALES  VNRFVAREAG  KYGVRSNLVA  AGPIRTLAMS
AIVGGALGEE  AGAQIQLLEE  GWDQRAPIGW  NMKDATPVAK  TVCALLSDWL
PATTGDIIYA  DGGAHTQLL
```

FIG. 10

Amino acid sequence of pS5 encoded by nucleic acid residues 494-1234

```
VTATATEGAK PPFVSRSVLV TGGNRGIGLA IAQRLAADGH KVAVTHRGSG
APKGLFGVEC DVTDSDAVDR AFTAVEEHQG PVEVLVSNAG LSADAFLMRM
TEEKFEKVIN ANLTGAFRVA QRASRSMQRN KFGRMIFIGS VSGSWGIGNQ
ANYAASKAGV IGMARSIARE LSKANVTANV VAPGYIDTDM TRALDERIQQ
GALQFIPAKR VGTPAEVAGV VSFLASEDAS YISGAVIPVD GGMGMGH
```

FIG. 11

DNA Sequence of pS5

```
   1   GTTCGCTCCG GCGCGGTCAC GCGCATGCCC TCGATGACGC AGATCTCGTC
  51   GGGCTCGATG CGCTCTTCCC AGACTTGCAG CCCCGGGGCA CGGCGGCGGT
 101   TGGTGTCGAT GATCGCGGCG GGAAGATCCG CGTCGATCCA CTTGGCGCCA
 151   TGGAAGGCAG AAGCCGAGTA GCCGGCCAGC ACGCCGCGGC GGCGCGAGCG
 201   CAGCCACAGC GCTTTTGCAC GCAATTGCGC GGTCAGTTCC ACACCCTGCG
 251   GCACGTACAC GTCTTTATGT AGCGCGACAT ACCTGCTGCG CAATTCGTAG
 301   GGCGTCAATA CACCCGCAGC CAGGGCCTCG CTGCCCAGAA AGGGATCCGT
 351   CATGGTCGAA GTGTGCTGAG TCACACCGAC AAACGTCACG AGCGTAACCC
 401   CAGTGCGAAA GTTCCCGCCG GAAATCGCAG CCACGTTACG CTCGTGGACA
 451   TACCGATTTC GGCCCGGCCG CGGCGAGACG ATAGGTTGTC GGGGTGACTG
 501   CCACAGCCAC TGAAGGGGCC AAACCCCCAT TCGTATCCCG TTCAGTCCTG
 551   GTTACCGGAG GAAACCGGGG GATCGGGCTG GCGATCGCAC AGCGGCTGGC
 601   TGCCGACGGC CACAAGGTGG CCGTCACCCA CCGTGGATCC GGAGCGCCAA
 651   AGGGGCTGTT TGGCGTCGAA TGTGACGTCA CCGACAGCGA CGCCGTCGAT
 701   CGCGCCTTCA CGGCGGTAGA AGAGCACCAG GGTCCGGTCG AGGTGCTGGT
 751   GTCCAACGCC GGCCTATCCG CGGACGCATT CCTCATGCGG ATGACCGAGG
 801   AAAAGTTCGA GAAGGTCATC AACGCCAACC TCACCGGGGC GTTCCGGGTG
 851   GCTCAACGGG CATCGCGCAG CATGCAGCGC AACAAATTCG GTCGAATGAT
 901   ATTCATAGGT TCGGTCTCCG GCAGCTGGGG CATCGGCAAC CAGGCCAACT
 951   ACGCAGCCTC CAAGGCCGGA GTGATTGGCA TGGCCCGCTC GATCGCCCGC
1001   GAGCTGTCGA AGGCAAACGT GACCGCGAAT GTGGTGGCCC CGGGCTACAT
1051   CGACACCGAT ATGACCCGCG CGCTGGATGA GCGGATTCAG CAGGGGGCGC
1101   TGCAATTTAT CCCAGCGAAG CGGGTCGGCA CCCCGCCGA GGTCGCCGGG
1151   GTGGTCAGCT TCCTGGCTTC CGAGGATGCG AGCTATATCT CCGGTGCGGT
1201   CATCCCGGTC GACGGCGGCA TGGGTATGGG CCACTGACAC AACACAAGGA
1251   CGCACATGAC AGGACTGCTG GACGGCAAAC GGATTCTGGT TAGCGGAATC
1301   ATCACCGACT CGTCGATCGC GTTTCACATC GCACGGGTAG CCCAGGAGCA
1351   GGGCGCCCAG CTGGTGCTCA CCGGGTTCGA CCGGCTGCGG CTGATTCAGC
1401   GCATCACCGA CCGGCTGCCG GCAAAGGCCC CGCTGCTCGA ACTCGACGTG
```

FIG. 12A

```
1451  CAAAACGAGG AGCACCTGGC CAGCTTGGCC GGCCGGGTGA CCGAGGCGAT
1501  CGGGGCGGGC AACAAGCTCG ACGGGGTGGT GCATGCGATT GGGTTCATGC
1551  CGCAGACCGG GATGGGCATC AACCCGTTCT TCGACGCGCC CTACGCGGAT
1601  GTGTCCAAGG GCATCCACAT CTCGGCGTAT TCGTATGCTT CGATGGCCAA
1651  GGCGCTGCTG CCGATCATGA ACCCCGGAGG TTCCATCGTC GGCATGGACT
1701  TCGACCCGAG CCGGGCGATG CCGGCCTACA ACTGGATGAC GGTCGCCAAG
1751  AGCGCGTTGG AGTCGGTCAA CAGGTTCGTG GCGCGCGAGG CCGGCAAGTA
1801  CGGTGTGCGT TCGAATCTCG TTGCCGCAGG CCCTATCCGG ACGCTGGCGA
1851  TGAGTGCGAT CGTCGGCGGT GCGCTCGGCG AGGAGGCCGG CGCCCAGATC
1901  CAGCTGCTCG AGGAGGGCTG GGATCAGCGC GCTCCGATCG GCTGGAACAT
1951  GAAGGATGCG ACGCCGGTCG CCAAGACGGT GTGCGCGCTG CTGTCTGACT
2001  GGCTGCCGGC GACCACGGGT GACATCATCT ACGCCGACGG CGGCGCGCAC
2051  ACCCAATTGC TCTAGAACGC ATGCAATTTG ATGCCGTCCT GCTGCTGTCG
2101  TTCGGCGGAC CGGAAGGGCC CGAGCAGGTG CGGCCGTTCC TGGAGAACGT
2151  TACCCGGGGC CGCGGTGTGC CTGCCGAACG GTTGGACGCG GTGGCCGAGC
2201  ACTACCTGCA TTTCGGTGGG GTATCACCGA TC
```

FIG. 12B

METHODS AND COMPOSITIONS FOR DETECTING AND TREATING MYCOBACTERIAL INFECTIONS USING AN INHA GENE

CROSS-REFERENCE TO RELATED APPLICATIONS

This is a Continuation-in-Part of application Ser. No. 08/062,409 filed May 14, 1993 now abandoned entitled USE OF GENES OF *M. TUBERCULOSIS* AND *M. SMEGMATIS* WHICH CONFER ISONIAZID RESISTANCE TO TREAT TUBERCULOSIS AND TO ASSESS DRUG RESISTANCE, which is hereby incorporated by reference herein in its entirety.

STATEMENT OF GOVERNMENT INTEREST

This invention was made with government support under NIH Grant No. A126170 and National Cooperative Drug Discovery Group Grant No. UO1A130189. As such, the United States government has certain rights in the invention.

FIELD OF THE INVENTION

The invention relates to materials and methods used in the diagnosis and treatment of mycobacterial diseases, and more specifically to DNA sequence(s) associated with resistance to isoniazid and its analogs in mycobacteria, methods for isolating such sequence(s), and the use of such sequence(s) in human and animal medical practice.

BACKGROUND OF THE INVENTION

Tuberculosis caused by members of the *M. tuberculosis* complex including *M. tuberculosis, M. bovis,* and *M. africanum* remains the largest cause of human death in the world from a single infectious disease, and is responsible for one in four avoidable adult deaths in developing countries. In addition, in 1990, there was a 10% increase in the incidence of tuberculosis in the United States. Further, *M. bovis* causes tuberculosis in a wide range of animals, and is a major cause of animal suffering and economic loss in animal industries.

Infection with drug-sensitive strains of the *M. tuberculosis* complex can be effectively cured with a combination of antibiotics, including isoniazid (isonicotinic acid hydrazide, INH), rifampicin, and pyrazinamide. INH was first reported to be active against *M. tuberculosis* in 1952, and particularly active against *M. tuberculosis* and *M. bovis.* However, mutants resistant to INH have emerged since then, and today such mutants account for as many as 26% of the clinical *M. tuberculosis* isolates in certain U.S. cities.

Some INH-resistant strains are associated with a loss of catalase activity, and deletions of the catalase-peroxidase gene (katG) correlate with INH resistance in certain *M. tuberculosis* isolates. Furthermore, transfer of the wild-type (wt) *M. tuberculosis* katG gene to INH-resistant *M. smegmatis* and *M. tuberculosis* confers INH sensitivity, suggesting that catalase-peroxidase activity is required for INH-sensitivity. However, in some studies only 10 to 25% of the INH-resistant isolates appear to be catalase negative, indicating that INH resistance can be due to other factors.

Drug resistance can be caused by many mechanisms, including mutations in the drug target that reduce the binding of the drug or mutations that lead to increased production of the target. The mechanism by which INH inhibits mycobacteria and its precise target of action are unknown. Biochemical evidence has suggested that both INH and ethionamide (ETH, a structural analog of INH) block mycolic acid biosynthesis in mycobacteria. INH has been found to inhibit mycolic acid biosynthesis in cell-free extracts of mycobacteria, but the target protein has not been identified. In addition, in certain cases, low-level INH resistance correlates not with the loss of catalase activity but with the coacquisition of ETH resistance, suggesting that the two drugs may share a common target.

Because such a high percentage of the *M. tuberculosis* complex strains are resistant to INH, a great need exists to identify its targets of action, and thereby to devise rapid methods for identification of INH-resistant strains and methods of treating individuals for prevention and/or treatment of the disease associated with them.

SUMMARY OF THE INVENTION

This invention is based upon the discovery of a gene, inhA (also called ps5), that encodes an enzyme (InhA). InhA is the target of action of isoniazid in mycobacteria. Mutations within the inhA gene result in isoniazid resistance. Thus, the present invention provides isolated and recombinant polynucleotide sequences and polypeptides encoded therein that are associated with resistance to INH and its structural analogs in members of the genus mycobacteria, particularly those of the *M. tuberculosis* complex, including *M. tuberculosis, M. africanum* and *M. bovis;* the *M. avium* complex, including *M. avium, M. intracellulare, M. scrofulaceum,* and *M. paratuberculosis; M. smegmatis.* It also provides the allelic counterparts that are associated with INH sensitivity. The polynucleotides of the invention have many uses. For example, they are useful in assessing the susceptibility of various strains of the *M. tuberculosis* complex to isoniazid type antibiotics, as decoys and antisense oligonucleotides to prevent the expression of polypeptides associated with isoniazid resistance, and for the expression of the polypeptides encoded therein. The polypeptides encoded in the polynucleotides and/or antibodies directed to them may also have use in immunoassays for the detection of INH-resistant strains, in the determination of whether an INH-type antibiotic may be effective against tuberculosis, and in the treatment of individuals for infection with these strains.

Accordingly, embodiments of the invention include the following.

An isolated wild-type gene which encodes an enzyme which is the target of action for isoniazid.

An isolated wild-type gene which encodes a polypeptide (InhA) which is the target of action for isoniazid (INH). These wild type genes also include those from *M. tuberculosis, M. avium, M. smegmatis,* and *M. bovis.*

An isolated mutant gene that encodes InhA wherein the mutant gene is associated with INH-resistance.

An isolated polynucleotide encoding an InhA polypeptide or fragment or variant thereof. These polynucleotides include recombinant expression vectors comprised of control sequences operably linked to a segment encoding the InhA polypeptide of fragment or variant thereof.

A host cell comprised of any of the aforementioned polynucleotides.

A method of treating an individual for infection caused by a member of the mycobacterial complex comprising:

(a) providing a composition comprised of a polynucleotide capable of inhibiting mRNA activity from an inhA operon of the infecting species and a suitable excipient; and (b) administering a pharmacologically effective amount of said composition to the individual.

The above-mentioned method wherein the mode of administration of the polynucleotides is oral, enteral, subcutaneous, intraperitoneal or intravenous.

A method of assessing susceptibility of a strain of mycobacteria in a biological sample to INH comprising:

(a) providing the mycobacterial DNA from the biological sample;

(b) amplifying a region of the inhA operon;

(c) determining whether a mutation exists within the inhA operon from the biological sample, the presence of the mutation indicating that said mycobacterial strain is resistant to INH.

The aforementioned method of wherein the amplification is by a polymerase chain reaction (PCR).

In addition, the aforementioned method further comprised of providing a comparable portion of wild-type INH-sensitive inhA operon from the mycobacteria, and the determination of whether a mutation exists in the biological sample is by comparison with the wild-type inhA operon.

The aforementioned method wherein determining whether a mutation exists is performed by single strand conformation polymorphism analysis.

A method of determining whether a drug is effective against mycobacterial infection comprising:

(a) providing isolated InhA;

(b) providing a candidate drug;

(c) mixing InhA with substrates for mycolic acid biosynthesis in the presence or absence of the candidate drug; and (d) measuring the inhibition of biosynthesis of mycolic acid caused by the presence of the drug, if any.

A method of producing a tuberculosis-specific mycolic acid comprising adding purified InhA to substrates required for the biosynthesis of mycolic acid.

A method for producing a compound that inhibits InhA activity comprising:

a. providing purified InhA;

b. determining the molecular structure of said InhA;

c. creating a compound with a similar molecular structure to INH; and d. determining that said compound inhibits the biochemical activity of InhA.

An isolated InhA polypeptide or fragment or variant thereof.

A recombinant mycobacterial vaccine comprised of attenuated mutants selected from the group consisting of BCG, M. tuberculosis, and M. bovis, wherein the mutants are host cells containing a mutated inhA gene.

BRIEF DESCRIPTION OF THE DRAWINGS

FIG. 1 is a table listing inhA genes from different mycobacteria that confer resistance to INH and ETH in M. smegmatis $mc^2$ 155.

FIG. 2 (SEQ ID NO:1, SEQ ID NO:2, and SEQ ID NO:3), presents a comparison of the coding strands of DNA sequences from M. bovis that confer resistance to INH and from M. tuberculosis* and *M. smegmatis* that confer sensitivity to INH. The mutation in $mc^2651$ that causes INH-resistance is indicated by the arrow.

FIG. 3 is a diagram of the subcloning strategy used to demonstrate that the isoniazid resistance phenotype is conferred by the inhA open reading frame.

FIG. 4 (SEQ ID NO:4 through SEQ ID NO:9) shows the alignment of the amino acid sequences of InhA proteins from *M. tuberculosis* H37R, *M. bovis*, *M. bovis* NZ, *M. smegmatis* $mc^2155$ and *M. smegmatis* $mc^2651$ with EnvM proteins from *S. typhimurium* and *E. coli*.

FIG. 5 is a bar graph showing the results of cell-free assays of mycolic acid biosynthesis, and the effect of insertion of inhA genes on the effect of INH.

FIG. 6 is a diagram of the allelic exchange experiment demonstrating that the point mutation in the $mc^2651$ inhA polynucleotide results in INH-resistance, and the results obtained from the experiment.

FIG. 7 (SEQ ID NO:10), comprised of sheets 7A, 7B, and 7C, shows the nucleic acid sequence that includes the *M. smegmatis* inhA gene.

FIG. 8 (SEQ ID NO:11), comprised of sheets 8A, 8B, and 8C, shows the nucleic acid sequence that includes the *M. tuberculosis* inhA gene.

FIG. 9 (SEQ ID NO:12, SEQ ID NO:3, and SEQ ID NO:14), comprised of sheets 9A, 9B, 9C and 9D, shows the nucleic acid sequence for pS5 and the amino acid sequence from two large open reading frames encompassed within it.

FIG. 10 (SEQ ID NO:14) presents the amino acid sequence of a fragment encoded by nucleic acid residues 1256–2062 (ORF2) of the pS5 operon.

FIG. 11 presents the amino acid sequence encoded by nucleic acid residues 494–1234 (ORF1) of the pS5 operon.

FIG. 12 (SEQ ID NO:12) presents the nucleic acid sequence of the *M. bovis* pS5 operon.

FIG. 13 presents a restriction enzyme map of pYUB18 showing some significant features of the genome.

DETAILED DESCRIPTION OF THE INVENTION

The invention stems from the discovery of inhA, a gene that encodes a polypeptide that is a target for INH and ETH in members of the *M. tuberculosis* complex. Mutations of the gene render mycobacteria INH- and ETH-resistant. The gene and mutations within it were identified using a genetic strategy. Genomic libraries were constructed in shuttle cosmid vectors from INH-resistant mutants of *M. smegmatis* and *M. bovis*. Transferral of the libraries into wild type (i.e., INH-sensitive) *M. smegmatis* strains allowed the identification of clones that consistently conferred INH-resistance (shown in the table in FIG. 1). The transformation of cosmids containing a cross-hybridizing DNA fragment from wt (INH-ETH-sensitive) strains of *M. smegmatis*, *M. tuberculosis*, *M. bovis*, *M. bovis* BCG, and *M. avium* yielded clones that conferred INH-ETH resistance. These results were suggestive that overexpression of a putative target gene, inhA, on a multi-copy plasmid conferred an INH-resistance phenotype. This led to the conclusion that InhA, the gene product of inhA, is the target of action for INH in members of the *M. tuberculosis* complex. Moreover, the results showing that a 3 kb BamHI DNA fragment from the *M. smegmatis* cosmid that conferred INH-resistance strongly hybridized to all of eleven mycobacterial species tested demonstrated that the inhA gene is highly conserved among mycobacteria.

The DNA fragments that conferred INH-sensitivity to *M. smegmatis* and *M. tuberculosis*, as well as those that were isolated from mutant INH-resistant *M. smegmatis* and *M. bovis* were subjected to DNA sequencing. These DNA sequences are shown in FIG. 2. FIG. 2 presents the DNA sequences of the INH-resistant polynucleotide from *M. bovis* and the INH-sensitive polynucleotides of *M. tuberculosis* and *M. smegmatis*. Sequence analysis revealed two ORFs, encoding proteins of 29 and 32 kD. Subcloning analyses of the *M. smegmatis* fragment demonstrated that the ORF encoding the 29 kD protein was responsible for the INH-resistance phenotype, and was termed the inhA gene. In the *M. bovis* and *M. tuberculosis* genomes, it appears that the inhA genes are positioned such that they are subject to the same transcriptional control elements (including the promoter) as is ORF1, whereas the inhA gene has its own promoter in the *M. smegmatis* genome.

Figure 3:
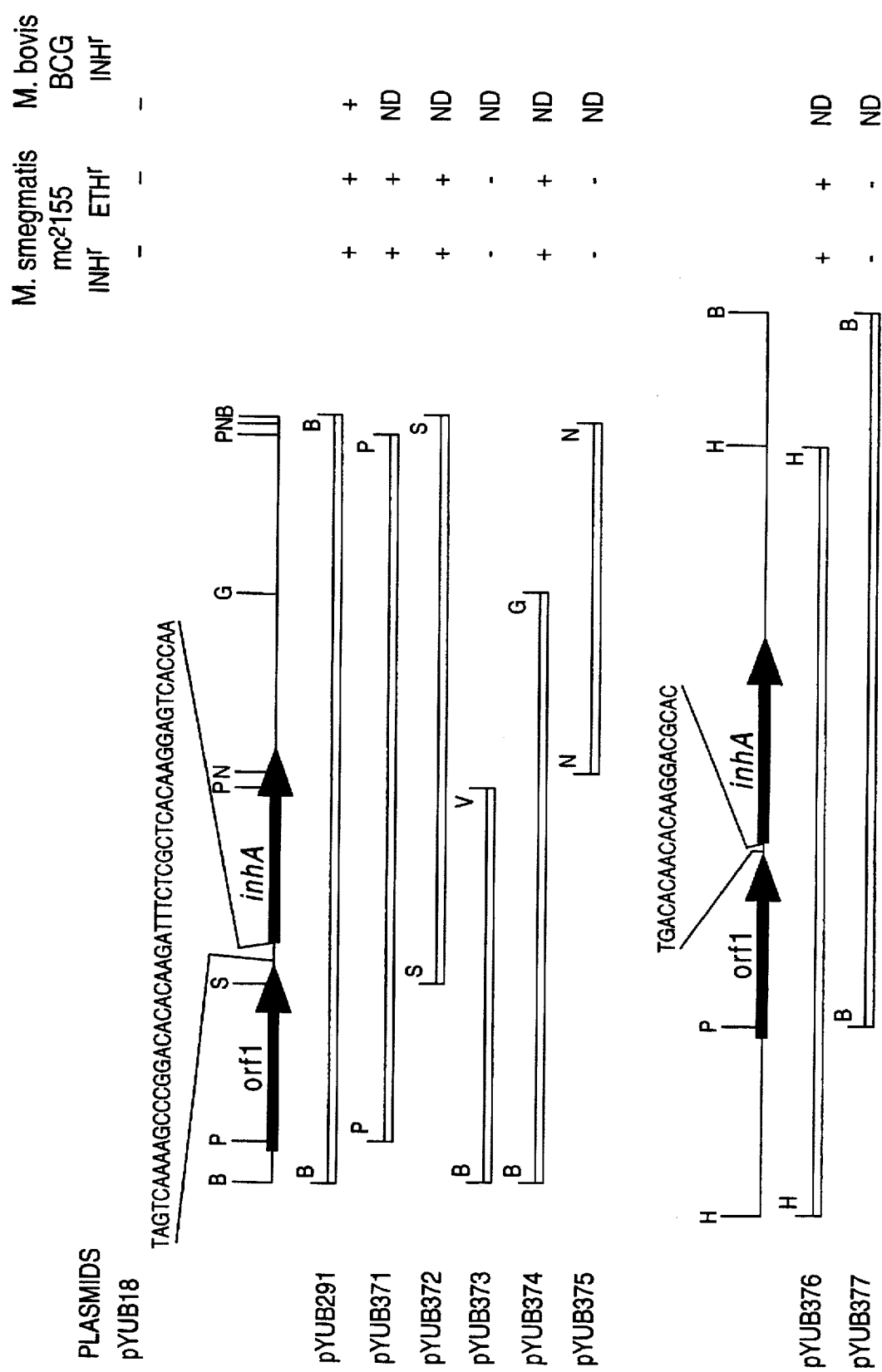

The *M. tuberculosis* and *M. smegmatis* inhA gene products show 38 and 40% homologies to the envM gene product of *S. typhimurium*. In addition, in the *M. smegmatis, M tuberculosis*, and *M. bovis* genomes the inhA ORFs are preceded by another ORF that shares 40% identity with acetyl CoA reductases. The similarities of the inhA ORF and ORF1 to lipid biosynthetic genes are consistent with the hypothesis that INH inhibits an enzyme involved in mycolic acid biosynthesis.

Sequence analysis and comparison of inhA from the mutant INH-resistant and wt INH-sensitive strains of *M. smegmatis* (See FIG. 4) and *M. bovis* revealed the presence of a single base pair difference that resulted in the amino acid substitution of an alanine for a serine at position 94 of the InhA protein. (See FIG. 4.) As shown in the Examples, this difference caused the Inh-resistance phenotype.

Polynucleotides from *M. smegmatis, M. tuberculosis*, and *M. bovis* that encode InhA have been identified, isolated, cloned, sequenced and characterized. The nucleic acid sequences for these polynucleotides are shown in FIGS. 7, 8, and 9 respectively. FIG. 9 also shows the amino acids encoded in the polynucleotide.

A comparison of the sequences for *M. tuberculosis* inhA and *M. bovis* inhA shows that the inhA gene from INH-sensitive *M. tuberculosis* and INH-sensitive *M. bovis* are identical. Given that the mutation of Ser to Ala conferring INH-resistance is conserved in *M. smegmatis* and *M. bovis* phenotypes, it can be anticipated that other INH-resistant isolates will be found that are due to mutations in the inhA operon. For example, INH-resistance may also be due to missense mutations in the coding region of inhA, or to mutations that cause the overexpression of InhA (e.g., mutations in the regulatory regions of the operon, and/or duplications that allow overexpression).

The discovery of inhA genes and operons of the mycobacterial complex that confer INH-resistance allows for the preparation and use of compositions and methods useful in the diagnosis and treatment of pathogenic states resulting from infection with these microorganisms, and particularly with INH-resistant strains.

The practice of the present invention will employ, unless otherwise indicated, conventional techniques of molecular biology, microbiology, recombinant DNA, and immunology, which are within the skill of the art. Such techniques are explained fully in the literature. See e.g., Sambrook, Fritsch, and Maniatis, MOLECULAR CLONING: A LABORATORY MANUAL, Second Edition (1989), OLIGONUCLEOTIDE SYNTHESIS (M. J. Gait Ed., 1984), the series METHODS IN ENZYMOLOGY (Academic Press, Inc.); GENE TRANSFER VECTORS FOR MAMMALIAN CELLS (J. M. Miller and M. P. Calos eds. 1987), HANDBOOK OF EXPERIMENTAL IMMUNOLOGY, (D. M. Weir and C. C. Blackwell, Eds.), CURRENT PROTOCOLS IN MOLECULAR BIOLOGY (F. M. Ausubel, R. Brent, R. E. Kingston, D. D. Moore, J. G. Siedman, J. A. Smith, and K. Struhl, eds., 1987), and CURRENT PROTOCOLS IN IMMUNOLOGY (J. E. Coligan, A. M. Kruisbeek, D. H. Margulies, E. M. Shevach and W. Strober, eds., 1991).

As used herein the term "target of action for isoniazid" refers to a polypeptide, InhA, encoded in an inhA operon of mycobacteria, and preferably in members of the mycobacterial complex.

As used herein, the term "inhA gene" refers to a polynucleotide that encodes a polypeptide that is present in mycobacteria, wherein the polypeptide has substantial amino acid homology and equivalent function to the InhA proteins of *M. tuberculosis, M. bovis,* or *M. smegmatis*; amino acid sequences of variants of these InhA proteins are shown in FIG. 4. In this context substantial amino acid homology means at least about 60% homology, generally at least about 70% homology, even more generally at least about 80% homology, and at times at least about 90% homology to any of the indicated polypeptides.

As used herein the term "polynucleotide" refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art (e.g., Sambrook, et al.), methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

The invention includes as an embodiment an isolated polynucleotide comprised of a sequence encoding a polypeptide associated with isoniazid (INH) resistance in mycobacteria or active fragment thereof. These isolated polynucleotides contain less than about 50%, preferably less than about 70%, and more preferably less than about 90% of the chromosomal genetic material with which the sequence encoding the polypeptide is usually associated in nature. An isolated polynucleotide "consisting essentially of" a sequence encoding an isoniazid resistance associated polypeptide lacks other sequences encoding other polypeptides derived from the mycobacterial chromosome.

As used herein "isoniazid" ("INH") refers to isoniazid and analogs thereof that inhibit mycobacterial replication by inhibiting the activity of the same polypeptide(s) INH inhibits, for example, ethonamide (ETH).

The invention also includes as embodiments recombinant polynucleotides containing a region encoding inhA gene products for mycobacteria. The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature; or (2) is linked to a polynucleotide other than that to which it is linked in nature; or (3) does not occur in nature.

A purified or recombinant polynucleotide comprised of a sequence encoding InhA of mycobacteria or variant or active fragment thereof, may be prepared by any technique known to those of skill in the art using the polynucleotide sequences provided herein. For example, they can be prepared by isolating the polynucleotides from a natural source, or by chemical synthesis, or by synthesis using recombinant DNA techniques.

It is contemplated that the sequence encoding an InhA encodes a polypeptide that is associated with isoniazid resistance or sensitivity in mycobacteria, and that allelic variations of the sequences, some of which are shown in the Figures are contemplated herein. The term "polypeptide" refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as the modifications known in the art, both naturally occurring and non-naturally occurring.

Also contemplated within the invention are cloning vectors and expression vectors comprised of a sequence encoding InhA or variant or fragment thereof. Suitable cloning vectors may be constructed according to standard techniques, or may be selected from the large number of cloning vectors available in the art. While the cloning vector selected may vary according to the host cell intended to be used, useful cloning vectors will generally have the ability to self replicate, may possess a single target for a restriction endonuclease, and may carry genes for a readily selectable marker (e.g., antibiotic resistance or sensitivity markers). Suitable examples include plasmids and bacterial viruses, e.g., PUC18, mp 18, mp19, PBR322, pMB9, ColE1, pCR1, RP4, phage DNAs, and shuttle vectors (e.g., pSA3 and pAT28. Preferred vectors include pBluescript IIks (Stratagene), and pYUB18.

Expression vectors generally are replicable polynucleotide constructs that encode a polypeptide operably linked to suitable transcriptional and translational regulatory elements. Examples of regulatory elements usually included in expression vectors are promoters, enhancers, ribosomal binding sites, and transcription and translation initiation and termination sequences. The regulatory elements employed in the expression vectors containing a polynucleotide encoding InhA or an active fragment would be functcenal in the host cell used for expression. It is also contemplated that the regulatory sequences may be derived from the inhA operon; thus, a promoter or terminator sequence may be homologous (i.e., from mycobacteria) to the coding sequence.

The invention also includes recombinant host cells comprised of any of the above described polynucleotides that contain a sequence encoding an InhA polypeptide of mycobacteria. The polynucleotides may be inserted into the host cell by any means known in the art. As used herein, "recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental, or deliberate mutation. Hosts which may be used include prokaryotic cells (e.g., bacterial cells such as *E. coli*, mycobacteria, and the like) and eukaryotic cells (e.g., fungal cells, insect cells, animal cells, and plant cells, and the like). Prokaryotic cells are generally preferred, and *E. coli* and *M. smegmatis* are particularly suitable. Of the latter, mc$^2$155 is particularly preferred.

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

The polynucleotides comprised of sequences encoding InhA are of use in the detection of INH-resistant forms of mycobacteria in biological samples. As used herein, a "biological sample" refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively infected cells, recombinant cells, and cell components). As used herein, the term "clinical sample" is synonymous with "biological sample".

The term "individual" as used herein refers to vertebrates, particularly members of the mammalian or avian species, and includes but is not limited to domestic animals, sports animals, and primates, including humans.

Using the disclosed portions of the isolated polynucleotides encoding InhA as a basis, oligomers of approximately 8 nucleotides or more can be prepared, either by excision from recombinant polynucleotides or synthetically, which hybridize with the mycobacterial sequences in the plasmids and are useful in identification of the INH-resistant and INH-sensitive mycobacteria. The probes are a length which allows the detection of the InhA encoding sequences by hybridization. While 6–8 nucleotides may be a workable length, sequences of 10–12 nucleotides are preferred, and about 20 nucleotides appears optimal. These probes can be prepared using routine methods, including automated oligonucleotide synthetic methods. For use as probes, complete complementarity is desirable, though it may be unnecessary as the length of the fragment is increased.

Thus, a polynucleotide comprising all or part of the nucleic acid sequences of an inhA operon, and particularly an inhA gene may be used as probes for identifying nucleic acids which code for polynucleotides associated with INH-resistance. The probes may be labelled, for example with radioactive isotopes. Usual isotopes include, for example $^{32}$P and $^{33}$P. The probes are capable of hybridizing to the genetic elements associated with INH-resistance. Preferably, the probes are specific for sequences that encode the INH-resistance gene. By way of example, the probe may be the entire nucleotide sequence depicted in FIG. 12. However, shorter probes are preferred.

For use of such probes as diagnostics, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are usually labeled. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies. The probes can be made completely complementary to the allelic form of polynucleotide that has been targeted. With this goal, high stringency conditions usually are desirable in order to prevent false positives. The stringency of hybridization is determined by a number of factors during hybridization and during the washing procedure, including temperature, ionic strength, length of time, and concentration of formamide. These factors are outlined in, for example, Maniatis, T. (1982).

It may be desirable to use amplification techniques in hybridization assays. Such techniques are known in the art and include, for example, the polymerase chain reaction (PCR) technique described which is by Saiki et al. (1986), by Mullis, U.S. Pat. No. 4,683,195, and by Mullis et al. U.S. Pat. No. 4,683,202. This technique may be used in conjunction with other techniques, for example, in single-strand conformation polymorphism analysis (see infra., in the Examples).

The probes can be packaged into diagnostic kits. Diagnostic kits include the probe DNA, which may be labeled; alternatively, the probe DNA may be unlabeled and the ingredients for labeling may be included in the kit in separate containers. The kit may also contain other suitably packaged reagents and materials needed for the particular hybridization protocol, for example, standards, as well as instructions for conducting the test. If the kit is to be used for an assay system which includes PCR technology it may also include primers for the PCR reaction.

The inhA gene sequence and polypeptides encoded therein may also be used for screening for drugs against mycobacteria, particularly members of the mycobacterial complex, and more particularly *M. tuberculosis* and *M. bovis*. For example, it can be used to express the INH-resistant and INH-sensitive polypeptides encoded in the allelic forms of inhA. Utilizing these polypeptides in vitro assays, one could monitor the effect of candidate drugs on mycolic acid biosynthesis. Drugs that inhibit mycolic acid biosynthesis are candidates for therapy of mycobacterial diseases. Drugs that may be tested for effectiveness in this type of system include INH, ETH, rifampicin, streptomycin, ethambutol, ciprofloxacin, novobiocin and cyanide.

The inhA operon sequences may also be used to design polynucleotides that can be used for treatment of mycobacterial infections, including those caused by *M. tuberculosis*, *M. avium*, *M. smegmatis*, and *M. bovis*. One method of treating a mycobacterial infection utilizing the InhA gene is by providing antisense polynucleotides or triplex forming polynucleotides which can be used to inhibit the transcription or translation of mRNA from the inhA operon, for example antisense polynucleotides, triplex forming polynucleotides, decoys, and ribozymes. Thus, these types of polynucleotides are also included within the invention. These polynucleotides may be prepared by a variety of techniques known in the art, including chemical synthesis and recombinant technology. After preparation they can then be administered, either alone or in combination with other compositions to treat mycobacterial infections, including tuberculosis. The compositions containing these polynucleotides may also include suitable excipients.

The sequence of inhA can also be used to assess the susceptibility of various strains of mycobacteria, and particularly of *M. tuberculosis* or *M. bovis*, in a clinical sample to INH. This susceptibility comparison is based upon the detection of a mutant allele as compared to the wild-type inhA allele that is INH-sensitive. Procedures to perform this type of assessment will be readily evident to those of skill in the art. For example, one procedure to perform this assessment is described in the Examples, and is based upon isolation of the chromosomal DNA of the bacterium, amplification of the inhA region by PCR using primers specific for the region (based upon the inhA sequences provided herein), and determination whether a mutation exists in the isolated DNA by the method of single strand conformation polymorphism analysis.

In addition, compounds which block the activity of InhA polypeptides (which may be enzymes) can be prepared utilizing the sequence information of inhA. This is performed by overexpressing InhA, purifying the polypeptide, and then performing X-ray crystallography on the purified InhA polypeptide to obtain its molecular structure. Next, compounds are created which have similar molecular structures to all or portions of the polypeptide. The compounds are then combined with the polypeptide and attached thereto so as to block the biochemical activity of the InhA polypeptide.

The inhA polynucleotides may also be used produce or improve live attenuated or killed tuberculosis vaccines. For example, a tuberculosis strain which contains a mutated inhA can be administered in vaccine form to eliminate INH-resistance which is typically conferred by mutant inhA. In addition, mutated inhA genes may be added to BCG or *M. tuberculosis* vaccines to provide attenuated mutant tuberculosis vaccines. These vaccines may be used to treat and prevent a wide variety of diseases, including tuberculosis, AIDS, leprosy, polio, malaria and tetanus.

The polypeptides of the invention include those encoded in allelic variants of inhA, some of which are shown in the Figures herein, and are in purified or recombinant form. These polypeptides include fragments of the entire polypeptides encoded in the ORFs, particularly fragments that exhibit activity in mycolic acid biosynthesis. In addition, polypeptides of the invention include variants of InhA which differ from the native amino acid sequences by the insertion, substitution, or deletion of one or more amino acids. These variants may be prepared chemically, or by alteration of the polynucleotide sequence encoding InhA, using techniques known in the art, for example, by site-specific primer directed mutagenesis. These polypeptides can be purified by any means known in the art, including, for example freeze-thaw extraction, salt fractionation, column chromatography, affinity chromatography and the like.

The polypeptides of the invention may find use as therapeutic agents for treatment of mycobacterial infection. "Treatment" as used herein refers to prophylaxis and/or therapy.

The InhA polypeptides can be prepared as discrete entities or incorporated into a larger polypeptide, and may find use as described herein. The immunogenicity of the epitopes of InhA may also be enhanced by preparing them in mammalian or yeast systems fused with or assembled with particle-forming proteins such as, for example, that associated with hepatitis B surface antigen. See, e.g., U.S. Pat. No. 4,722, 840. Vaccines may be prepared from one or more immunogenic polypeptides derived from InhA.

The preparation of vaccines which contain an immunogenic polypeptide(s) as active ingredients, is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1,'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing an InhA antigenic sequence resulting from administration of this polypeptide in vaccines which are also comprised of the various adjuvants.

The vaccines are conventionally administered parenterally, by injection, for example, either subcutaneously or intramuscularly. Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25%–70%.

The proteins may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be prophylactically and/or therapeutically effective. The quantity to be administered, which is generally in the range of 5 micrograms to 250 micrograms of antigen per dose, depends on the subject to be treated, capacity of the subject's immune system to synthesize antibodies, and the degree of protection desired. Precise amounts of active ingredient required to be administered may depend on the judgment of the practitioner and may be peculiar to each subject.

The vaccine may be given in a single dose schedule, or preferably in a multiple dose schedule. A multiple dose schedule is one in which a primary course of vaccination may be with 1–10 separate doses, followed by other doses given at subsequent time intervals required to maintain and or reenforce the immune response, for example, at 1–4 months for a second dose, and if needed, a subsequent dose(s) after several months. The dosage regimen will also, at least in part, be determined by the need of the individual and be dependent upon the judgment of the practitioner.

In addition, the vaccine containing the immunogenic InhA antigen(s) may be administered in conjunction with other immunoregulatory agents, for example, immune globulins, as well as antibiotics.

The InhA antigens may be used for the preparation of antibodies. The immunogenic polypeptides prepared as described above are used to produce antibodies, including polyclonal and monoclonal. If polyclonal antibodies are desired, a selected mammal (e.g., mouse, rabbit, goat, horse, etc.) is immunized with an immunogenic polypeptide bearing an InhA epitope(s). Serum from the immunized animal is collected and treated according to known procedures. If serum containing polyclonal antibodies to an InhA epitope contains antibodies to other antigens, the polyclonal antibodies can be purified by immunoaffinity chromatography. Techniques for producing and processing polyclonal antisera are known in the art, see for example, Mayer and Walker (1987).

Monoclonal antibodies directed against InhA epitopes can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980); Hammerling et al. (1981); Kennett et al. (1980); see also, U.S. Pat. Nos. 4,341,761; 4,399,121; 4,427,783; 4,444,887; 4,466,917; 4,472,500; 4,491,632; and 4,493,890. Panels of monoclonal antibodies produced against InhA epitopes can be screened for various properties; i.e., for isotype, epitope affinity, etc.

Antibodies, both monoclonal and polyclonal, which are directed against InhA epitopes are particularly useful in diagnosis, and those which are neutralizing may be useful in passive immunotherapy. Monoclonal antibodies, in particular, may be used to raise anti-idiotype antibodies.

Anti-idiotype antibodies are immunoglobulins which carry an "internal image" of the antigen of the infectious agent against which protection is desired. See, for example, Nisonoff, A., et al. (1981) and Dreesman et al. (1985). Techniques for raising anti-idiotype antibodies are known in the art. See, for example, Grzych (1985), MacNamara et al. (1984), and Uytdehaag et al. (1985). These anti-idiotype antibodies may also be useful for treatment, vaccination and/or diagnosis of mycobacterial infections, as well as for an elucidation of the immunogenic regions of InhA antigens.

Both the InhA polypeptides and anti-InhA antibodies are useful in immunoassays to detect presence of antibodies to mycobacteria, or the presence of the InhA antigens, and particularly the presence of INH-resistant InhA in biological samples. Design of the immunoassays is subject to a great deal of variation, and many formats are known in the art. The immunoassay will utilize at least one epitope derived from InhA. In one embodiment, the immunoassay uses a combination of epitopes derived from InhA. These epitopes may be derived from the same or from different bacterial polypeptides, and may be in separate recombinant or natural polypeptides, or together in the same recombinant polypeptides. An immunoassay may use, for example, a monoclonal antibody directed towards an InhA epitope(s), a combination of monoclonal antibodies directed towards epitopes of one mycobacterial antigen, monoclonal antibodies directed towards epitopes of different mycobacterial antigens, polyclonal antibodies directed towards the same antigen, or polyclonal antibodies directed towards different antigens. Protocols may be based, for example, upon competition, or direct reaction, or sandwich type assays. Protocols may also, for example, use solid supports, or may be by immunoprecipitation. Most assays involve the use of labeled antibody or polypeptide; the labels may be, for example, enzymatic, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Typically, an immunoassay for an anti-InhA antibody(s) will involve selecting and preparing the test sample suspected of containing the antibodies, such as a biological sample, then incubating it with an antigenic (i.e., epitope-containing) InhA polypeptide(s) under conditions that allow antigen-antibody complexes to form, and then detecting the formation of such complexes. Suitable incubation conditions are well known in the art. The immunoassay may be, without limitations, in a heterogenous or in a homogeneous format, and of a standard or competitive type.

In a heterogeneous format, the polypeptide is typically bound to a solid support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immulon), diazotized paper, nylon membranes, activated beads, and Protein A beads. For example, Dynatech Immulon™[1] or Immulon ™ microtiter plates or 0.25 inch polysterene beads (Precision Plastic Ball) can be used in the heterogeneous format. The solid support containing the antigenic polypeptide is typically washed after separating it from the test sample, and prior to detection of bound antibodies. Both standard and competitive formats are known in the art.

Complexes formed comprising anti-InhA antibody (or, in the case of competetive assays, the amount of competing antibody) are detected by any of a number of known techniques, depending on the format. For example, unlabeled anti-InhA antibodies in the complex may be detected using a conjugate of antixenogeneic Ig complexed with a label, (e.g., an enzyme label).

In immunoassays where InhA polypeptides are the analyte, the test sample, typically a biological sample, is incubated with anti-InhA antibodies under conditions that allow the formation of antigen-antibody complexes. It may be desirable to treat the biological sample to release putative bacterial components prior to testing. Various formats can be employed. For example, a "sandwich assay" may be employed, where antibody bound to a solid support is incubated with the test sample; washed; incubated with a second, labeled antibody to the analyte, and the support is washed again. Analyte is detected by determining if the second antibody is bound to the support. In a competitive format, which can be either heterogeneous or homogeneous, a test sample is usually incubated with antibody and a labeled, competing antigen is also incubated, either sequentially or simultaneously. These and other formats are well known in the art.

The following examples are provided only for illustrative purposes, and not to limit the scope of the present invention.

In light of the present disclosure numerous embodiments within the scope of the claims will be apparent to those of ordinary skill in the art.

EXAMPLES

Example 1

Selection of INH-Resistant *M. bovis* Strains

In order to select *M. bovis* INH-resistant strains, a virulent wild-type New Zealand strain of *M. bovis* was cloned by four serial passages using a combination of liquid Tween albumin broth (TAB) and 7H10 pyruvate agar culture media. A single colony of *M. bovis* was inoculated into TAB and incubated until visible growth was apparent. An appropriate dilution of the bacterial suspension in TAB was plated onto the agar media to obtain discrete colonies. After incubation, a single colony was picked and inoculated into TAB and the cloning procedure was repeated. After four cloning cycles a G4 strain was obtained. INH-resistant strains were obtained by growing the G1 strain in liquid TAB media containing differing concentrations of INH. After incubation, the strain that had luxuriant growth in the highest concentration of INH was inoculated onto INH-containing solid media and incubated for growth. A colony was picked, used as inoculum for INH-containing TAB, and incubated under growth conditions. When visible growth was apparent, the medium was used to inoculate liquid TAB media containing INH, and the inoculated medium was allowed to incubate under growth conditions. Aliquots of the culture were then grown again in liquid TAB media containing increased differing concentrations of INH, and cloning of a colony from a strain that had luxuriant growth in the highest concentration of INH was repeated. This selection procedure was repeated and a series of clones of *M. bovis* with increasing resistance to isoniazid were obtained. The last strain selected, G4/100, was resistant to 100 µg/ml of INH.

Example 2

Figure 13:
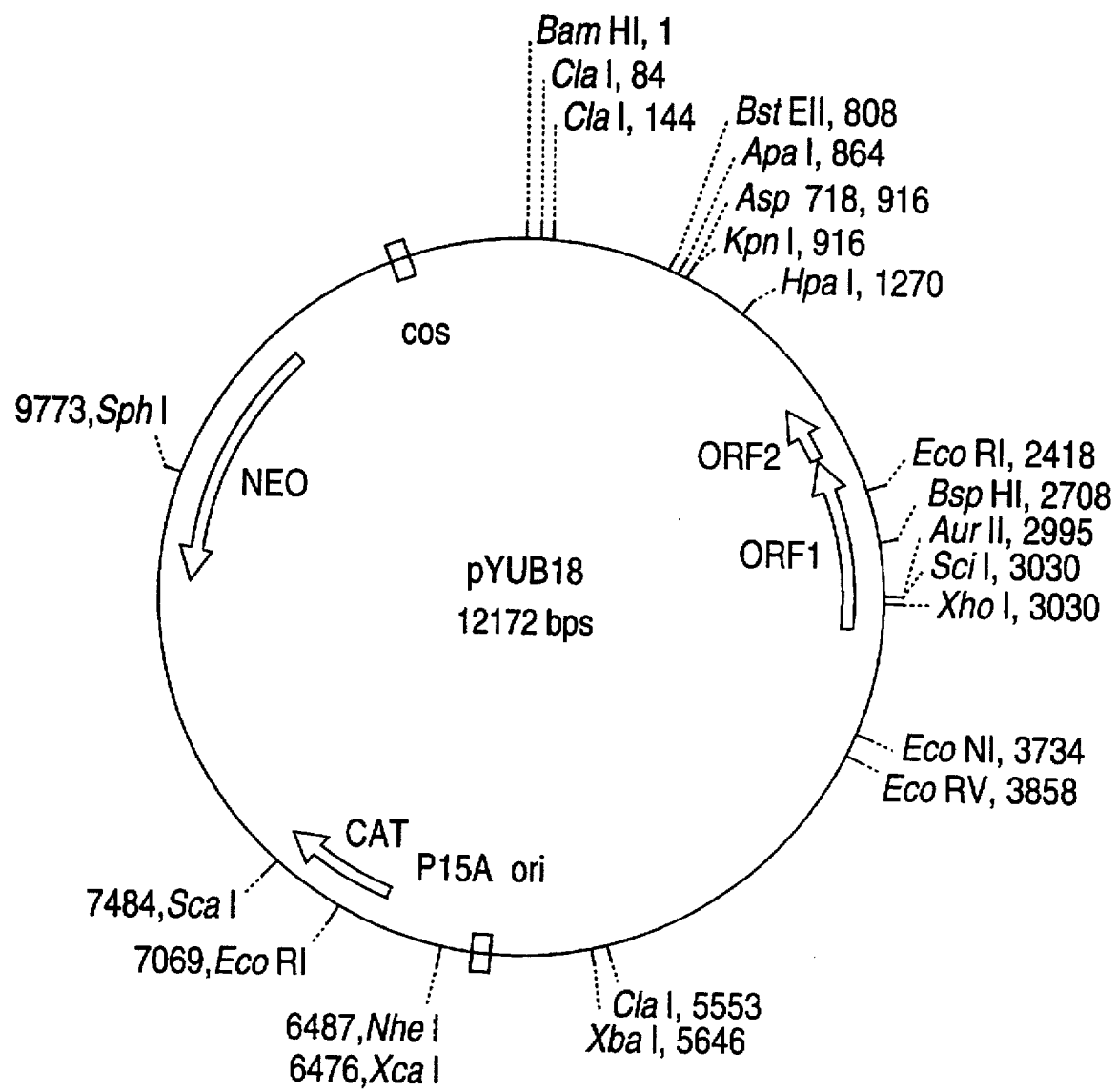

Isolation of INH-resistant Clones from a Cosmid Library prepared from an INH-Resistant Strain A cosmid library from strain G4/100 was prepared in the shuttle vector pYUB18. Plasmid pYUB18 is a multicopy *E. coli*-mycobacteria shuttle cosmid that contains a selectable kanamycin gene and a cos site (J. T. Beslile et al., J. Bacteriol. 173, 6991 (1991); S. B. Snapper et al., Mol. Microbiol. 4:1911 (1990); W. R. Jacobs et al., Methods Enzymol. 204:537 (1991)). A restriction enzyme map of pYUB18 showing some significant features of the genome is shown in FIG. 13.

The cosmid library was prepared as follows using standard techniques. Chromosomal DNA was purified from G4/100, and subjected to partial digestion with Sau3A1; fragments between about 30–50 kb were purified by sucrose gradient purification and ligated to linearized pYUB18. Resulting cosmids were packaged into λ-phage using a commercial kit (Gigapack Gold Stratagene) according to the manufacturer's directions, and transfected into *E. coli*; approximately 5000 colonies were obtained. The colonies were pooled and the plasmids amplified, using standard plasmid preparation techniques.

The cosmid library was then transformed into *M. smegmatis* strain mc$^2$155 by electroporation. Transformants were selected by growth on medium containing kanamycin. Approximately 1200 kanamycin resistant clones were patched onto media containing INH. Four INH resistant clones were identified.

Example 3

Isolation and Sequencing of pS5

In order to obtain a plasmid containing mycobacterial genetic material that conferred INH-resistance, the plasmids were extracted from the transformants. Cultures of *M. smegmatis* (5 ml) were incubated with cycloserine and ampicillin for 3 hours before harvest. The cells were pelleted and resuspended in 0.25 ml of 40 mM Tris acetate, 2 mM EDTA, pH 7.9. To this, 0.5 ml of lysing solution was added (50 mM Tris, 3% sodium dodecylsulfate (SDS)) and the solution was mixed for 30 minutes. The sample was heated to 60° C for 20 minutes, cooled for 10 minutes and the DNA was extracted by adding 0.8 ml of phenol (containing 50 mM NaCl). This was centrifuged and the upper layer containing the DNA was removed. To precipitate the DNA, a half volume of 7.5M ammonium acetate was added, incubated on ice for 30 minutes and then centrifuged for 30 minutes. The DNA was resuspended in 10 mM Tris, 1 mM EDTA.

The smallest plasmid obtained which conferred an Inh-resistance phenotype on *M. smegmatis* was 2.3 kb in size and was designated pS5.

The sequence of pS5 was obtained as follows. pS5 was cloned into the vector pBluescript II KS+ (Stratagene, Calif.). This vector contains the T3 and T7 promoters which were used for the sequencing. Sequencing was carried out using the dsDNA cycle sequencing system from GIBCO BRL, Life Technologies, according to the manufacturer's directions. The radioactive labelled nucleotide was either [γ-$^{32}$P] ATP or [γ-$^{33}$P] ATP, available from Amersham. The sequencing program used was GCG. Sequence analysis software package. The nucleic acid sequence for pS5 and the amino acid sequence from two large open reading frames encompassed within it are shown in FIG. 9. FIG. 10 presents the amino acid sequence of a fragment encoded by nucleic acid residues 1256–2062 (the InhA gene) of the pS5 operon. FIG. 11 presents the amino sequence of a fragment encoded by nucleic acid residues 494–1234 of the pS5 operon. FIG. 12 presents the nucleic acid sequence of the pS5 *M. bovis* NZ operon.

Example 4

Determination of Catalase Activity in an INH-Resistant Strain

Catalase activity of an INH-sensitive strain of *M. bovis* was determined. The enzyme was first isolated from the strain by pelleting a culture of *M. bovis*, resuspending it in 50 mM potassium phosphate buffer, pH 7, and adding it to a tube containing 0.5 g zirconium beads (Biospecs products), and vortexing for 5 min. The sample was centrifuged briefly, the supernatant collected and diluted to 4 ml with 50 mM potassium phosphate buffer, and filter sterilized through 0.22 μm filters.

Catalase catalyzes the conversion of $H_2O_2$ to and $O_2$. Catalase activity was assayed by incubating an aliquot of supernatant, prepared as above, with 3 μm $H_2O_2$ in a total volume of 3 ml for 5 minutes. The reaction was stopped by adding 1.5 ml of titanium tetrachloride reagent (1.5 mg/ml $TiCl_4$ in 4.5M $H_2SO_4$). The absorbance was read at 410 nm and the catalase activity was calculated using a standard curve of the amount of hydrogen peroxide versus wavelength at 410 nm; the activity was expressed as μmol/min/mg protein.

Catalase activity of G4/100, G4 and another virulent *M. bovis* strain were also determined using the above-described procedure. The G4 strain and other virulent *M. bovis* strains contained similar levels of catalase activity. Catalase activity was not detected in the G4/100 strain.

To demonstrate that the development of INH-resistance in G4/100 was not due entirely to loss of catalase activity, the plasmid pS5 was electroporated into G4 to produce G4(S5). G4(S5) grew on media containing a level of INH that prevented growth of G4. Using the method described above, catalase activity was tested in both G4 and G4(S5). G4(S5) which is INH-resistant, and G4 which is INH-sensitive, both showed similar levels of catalase activity.

Example 5

Identification of the InhA Gene of *M. smegmatis*

A spontaneous INH-ETH-resistant mutant of *M. smegmatis*, mc$^2$651, was isolated from wt *M. smegmatis* in a single step with a mutational frequency of $10^{-7}$. A genomic library from mc$^2$651 was constructed in a multicopy (5 to 10 copies) shuttle cosmid vector; the vector was described by Y. Zhang et al., Mol. Microbiol. 8, 521 (1993). Upon transfer of the library into wt *M. smeqmatitis* strains, cosmid clones were identified that consistently conferred INH-ETH resistance. These results are shown in the table in FIG. 1.

Cells of *M. smegmatis* mc$^2$155 bearing the indicated plasmids (derived from insertion into pYUB18) were grown in 7H9 broth containing kanamycin (15μg/ml), and dilutions were plated on 7H10 agar plates containing kanamycin alone or kanamycin with various concentrations of INH or ETH. The strains without any plasmid were grown in 7H9 broth, and dilutions were plated on 7H10 agar plates and on 7H10 agar plates with various concentrations of INH or ETH.

The transformation of cosmids containing a cross-hybridizing DNA fragment from wt ( INH-ETH-sensitive strains) of *M. smegmatis, M. tuberculosis, M. bovis, M. bovis* BCG, and *M. avium* yielded clones that conferred INH-ETH resistance. The INH-ETH resistance conferred by the transfer of the wt DNA fragment could be due to overexpression of the target, as is the case for the resistance phenotype seen with several antibiotics.

A 3-kb Bam HI DNA fragment from the *M. smegmatis* cosmid pYUB286 that conferred INH resistance was used as a probe for Southern (DNA) analysis. This probe strongly hybridized to all of the 11 different mycobacterial species tested, including the pathogenic strains *M. tuberculosis, M. bovis, M. avium,* and *M. leprae,* demonstrating that this sequence is highly conserved among the mycobacteria.

The DNA fragments hybridizable with those that conferred resistance to INH were isolated from the wt (INH-sensitive) strains of *M. smegmatis, M. bovis,* and *M. tuberculosis,* as well as from the INH-resistant mutants of *M. smegmatis* and *M. bovis.* Sequence analysis revealed that each strain contains two open reading frames (ORFs), one encoding a 29-kD protein followed by another encoding a 32-kD protein. FIG. 2 presents the DNA sequences of INH-resistant polynucleotides from *M. tuberculosis, M. bovis,* and *M. smegmatis.* The point mutation that differs between the INH-resistant and INH-sensitive *M. smegmatis* strains, and that determines resistance, is shown in the Figure.

Subcloning studies to determine the smallest fragments to confer INH-resistance were performed; the strategy is shown in FIG. 3. In the Figure, panel A is subcloning of *M.*

*smegmatis* mc²155, and panel B is of *M. tuberculosis* H37Rv. The *M. smegmatis* mc²155 were transformed with a pool of *E. coli*-mycobacteria shuttle cosmids, and individual clones were scored for resistance (r,+) or sensitivity (−) to INH and ETH. The ORF preceding inhA is labeled orfl and the sequence of the intervening DNA is shown. The ribosome binding sites are indicated in boldface letters. The following enzymes were used for subcloning: B, Bam HI; P, Pst I;, S, Spe I, V, Pvu II, N, Nla III; G, Bgl II, H, Nhe I. All the subclones were tested in both orientations. Subcloning analysis of *M. bovis* DNA yielded results similar to those obtained with *M. tuberculosis*. Plasmid pYUB291 was also shown to confer INH and ETH resistance in *M. bovis* BCG host.

The subcloning studies demonstrated that the second ORF from *M. smegmatis* was sufficient to confer the INH-resistance phenotype. This second ORF was thus named the inhA gene. In contrast to the *M. smegmatis* gene, the *M. tuberculosis* and *M. bovis* inhA genes appear to be in an operon with the gene encoding the 29-kD ORF, an observation confirmed by subcloning. In *M. tuberculosis* and *M. bovis* DNA, the noncoding region between the two ORFs was substantially shorter than that in *M. smegmatis* and may lack a promoter that appears to be present in the latter strain. The inhA DNA sequences have been submitted to GenBank. The accession numbers are U02530 (for *M. smegmatis*) and U02492 (for *M. tuberculosis*). The *M. bovis* sequence is identical to that of *M. tuberculosis*.

The InhA protein may use nicotinamide or flavin nucleotides as substrates or cofactors, as translation of the putative protein encoded therein indicates that it has a putative binding site for these molecules.

Example 6

Effect of InhA on Mycolic Acid Biosynthesis

As shown in FIG. 4, the predicted InhA proteins of *M. tuberculosis*, *M. bovis*, and *M. smegmatis* show strong sequence similarity (about 40% identity over 203 amino acids) to the EnvM proteins of *S. typhimurium* and *E. coli*. The figure aligns the amino acid sequences of InhA proteins from the indicated strains with the EnvM proteins from *E. coli* and *S. typhimurium*. The amino acid sequences were obtained by conceptual translation of the inhA and envM ORFs. Over a stretch of 203 amino acids, InhA and EnvM show about 75% sequence similarity (40% identity). InhA is highly conserved among mycobacterial strains. The InhA proteins of *M. tuberculosis* H37Rv and *M. bovis* are identical and hence are represented by a single sequence. The *M. tuberculosis*-*M. bovis* InhA has greater than 95% identity with the *M. smegmatis* InhA. The various envM gene products are also highly conserved (98% identity) (F. Turnowsky et al., J. Bacteriol. 171, 6555 (1989); H. Bergler et al., J. Gen. Microbiol. 138, 2093 (1992). The protein EnvM is thought to be involved in fatty acid biosynthesis. The relatively close homologies suggest that inhA may be involved in lipid biosynthesis.

Figure 5:
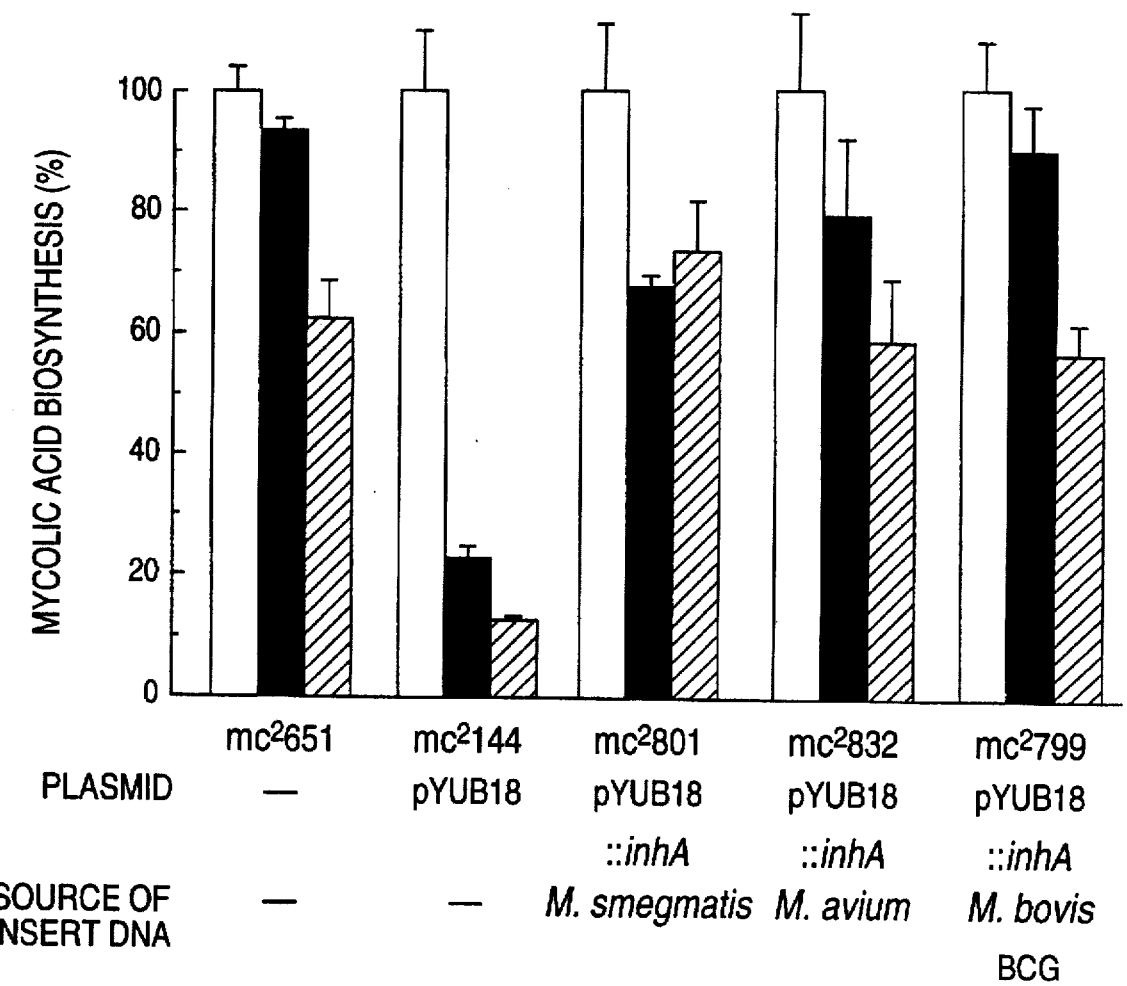

The effect of inhA on mycolic acid biosynthesis was determined in cell-free assays. The *M. smegmatis* mc²155 gene was transformed with pYUB18 vector (strain mc²144), or pYUB18 carrying the inhA genes of *M. smegmatis* (pYUB291, product of subcloning of pYUB286, strain mc²801), *M. avium* (pYUB317, strain mc²832), or *M. bovis* BCG (pYUB316, strain mc²799). Cell-free extracts were prepared from each of these strains and from the spontaneous INH-resistant mutant (mc²651 of *M. smegmatis*. Incorporation of [1-$^{14}$C]acetate into mycolic acids was measured using an assay described in L. M. Lopez-Marin et al., Biochim. Biophys. Acta 1086, 22 (1991), after preincubation with or without Inh. Protein concentrations in cell-free extracts were adjusted to 0.37 to 0.50 mg/ml, which resulted in the linear incorporation of radioactivity into the mycolic acids after a 1-hour incubation of the cell-free extract with the radioactive acetate. Each assay was done in duplicate, and the experimental error between different experiments was no more than 15%. The results of the cell-free assays of mycolic acid biosynthesis are shown in FIG. 5. The INH concentration necessary for strong inhibition of mycolic acid biosynthesis in cell-free extracts of the sensitive strain was about 20 times greater than the MIC (here, 20×MIC×100 μg/ml, solid bars.) Open bars, 0 μg/ml; crosshatched bars, 250 μg/ml. A 20- to 50-fold accumulation of INH has been reported to occur inside the mycobacteria.

As seen from the results in FIG. 5, compared to wt extracts, cell-free extracts from the resistant mutant mc²651 or from resistant merodiploids containing multiple copies of inhA showed marked resistance to the INH-mediated inhibition of mycolic acid biosynthesis. This result is supportive of the suggestion that InhA is required for mycolic acid biosynthesis.

Example 7

Allele Exchange of inhA Genes Conferring Inh-Resistance and Sensitivity Phenotypes The InhA protein from the INH-resistant mutant (mc²651) differs from the wt (mc²155) by a single substitution of Ser to Ala at position 94. To test whether this difference caused the INH resistance phenotype in mc²651, an allele exchange was performed on the *M. smegmatis* chromosome. The mc²651 cells were transformed with a 45 kb *M. smegmatis* DNA fragment that contained the wt inhA gene linked to a kan$^r$ marker gene.

Figure 6:
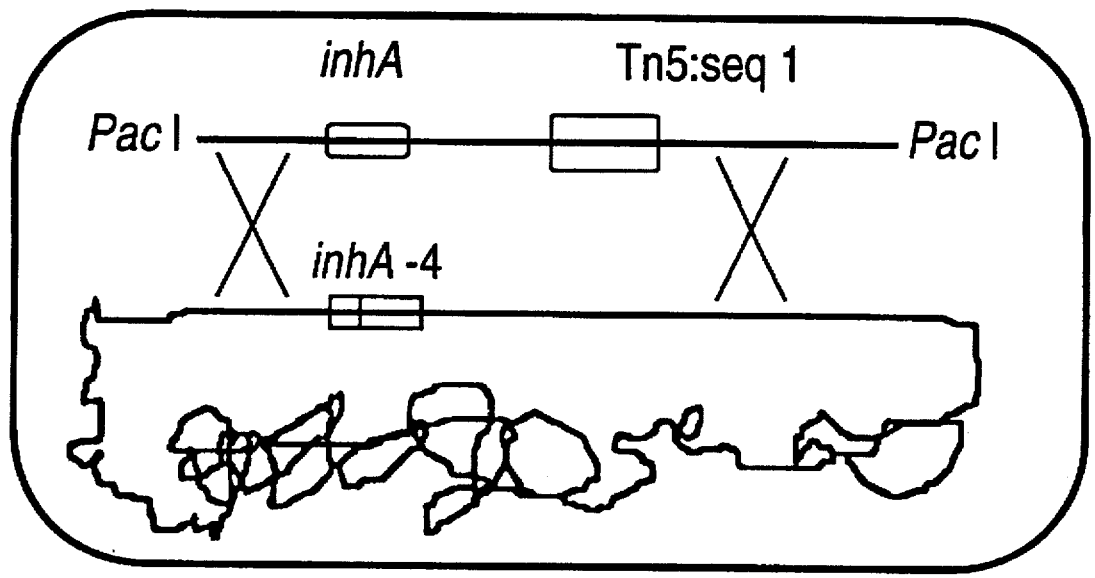

A 45 kb long DNA fragment containing the inhA allele from mc²155 was cloned into a vector with Pac I sites flanking the insert, and a Tn5sequ1 transposon (containing the kan$^r$ gene) was introduced near inhA. The linear Pac I fragment containing inhA linked to kan$^r$ was transformed into mc²651 by electroporation. The transformants were plated on 7H10 plates containing kanamycin (15 mg/ml). The kanamycin-resistant transformants were then scored for INH sensitivity on 7H10 plates containing both kanamycin (15 μg/ml) and INH (10 μg/ml). INH sensitivity contransformed with kanamycin resistance in 93 of 130 (72%) transformants tested. The remaining transformants were as resistant to INH as was mc²651 (MIC=50 μg/ml). FIG. 6 presents a diagram of the allelic exchange experiment.

Allelic exchange was confirmed by restriction fragment length polymorphism analysis of the inhA polymerase chain reaction (PCR) products obtained from the recombinants and by Southern blots.

This result provides evidence that the mutation of Ser to Ala$^{94}$ mediates the INH-resistance phenotype in *M. smegmatis*.

An allelic exchange could not be performed in *M. bovis* because a homologous recombination system is lacking. However, the mutant *M. bovis* gene conferred a higher level of resistance to INH (100% survival in 20 μg/ml of INH, MIC=30 μg/ml) than did the wt M. bovis gene (0% survival in 20 μg/ml of INH, MIC=15 μg/ml) when transformed into *M. smegmatis* mc²155 on a pYUB18 cosmid vector. These results shown in the table in FIG. 1, demonstrate that the identical mutation of Ser to Ala caused INH resistance in *M. bovis* NZ.

Example 8

Susceptibility of M. tuberculosis in a Clinical Sample to INH: Single Strand Polymorphism Conformation Analysis A polynucleotide encoding InhA can be used to assess the susceptibility of various strains of *M. tuberculosis* in a clinical sample to INH.

The chromosomal DNA of *M. tuberculosis* is isolated from a clinical sample. Oligonucleotides are prepared using the wild-type inhA sequence of *M. tuberculosis.* This sequence is depicted in FIG. 8. Regions of the inhA gene of *M. tuberculosis* from the clinical sample which are identified by use of the oligonucleotides are amplified using polymerase chain reaction (PCR) to obtain double stranded DNA. Next, in order to determine whether a mutant inhA gene exists, single strand conformation polymorphism analysis is performed. An example of single strand conformation polymorphism analysis is described by Telenti et al. in "Detection of Rifampicin-Resistance Mutations in *Mycobacterium Tuberculosis*", Vol. 341 pages 647–650 (March 1993).

In order to perform single strand conformation polymorphism, PCR is performed after substitution of half of the dCTP by $^{32}$P-α-dCTP or chemiluminescent substrates per reaction to generate a labelled 157 bp product. After amplification, the PCR product is diluted to an appropriate concentration with dilution buffer. An aliquot of diluted product is mixed with an appropriate aliquot of sequence loading buffer (Sequenase kit), heated for ten minutes at about 94° C., cooled on ice and loaded onto a non-denaturing sequencing format 0.5% MDE gel (Hydrolink, AT Biochem, Malvern, Pa.) Electrophoresis is then performed at room termperature and constant power overnight. The gels are then dried and exposed for autoradiography overnight.

We claim:

1. An isolated polynucleotide comprised of a sequence encoding a mycobacterial InhA polypeptide, wherein the polypeptide has at least 80% sequence identity to the mycobacterial polypeptide encoded in SEQ ID NO:1 and is involved in mycolic acid biosynthesis.

2. The isolated polynucleotide of claim 1, wherein the polypeptide can confer isoniazid (INH) sensitivity to mycobacterium.

3. The isolated polynucleotide of claim 1, wherein the polypeptide can confer INH resistance to mycobacterium.

4. An isolated polynucleotide comprised of a sequence encoding a mycobacterial InhA polypeptide, wherein the polypeptide has at least 80% sequence identity to the mycobacterial polypeptide encoded in SEQ ID NO:3 and is involved in mycolic acid biosynthesis.

5. The isolated polynucleotide of claim 4, wherein the polypeptide can confer INH sensitivity to mycobacterium.

6. The isolated polynucleotide of claim 4, wherein the polypeptide can confer INH resistance to mycobacterium.

7. An isolated polynucleotide according to claim 1, wherein the polypeptide has at least 90% sequence identity to the mycobacterial polypeptide encoded in SEQ ID NO:1.

8. The isolated polynucleotide of claim 7, wherein the polypeptide can confer INH sensitivity to mycobacterium.

9. The isolated polynucleotide of claim 7, wherein the polypeptide can confer INH resistance to mycobacterium.

10. An isolated polynucleotide according to claim 1, wherein the InhA polypeptide has the amino acid sequence present in that of SEQ ID NO:4.

11. An isolated polynucleotide according to claim 1, wherein the InhA polypeptide has the amino acid sequence present in that of SEQ ID NO:5.

12. An isolated polynucleotide according to claim 1, wherein the InhA polypeptide has the amino acid sequence present in that of SEQ ID NO:6.

13. An isolated polynucleotide according to claim 1, wherein the InhA polypeptide has the amino acid sequence present in that of SEQ ID NO:7.

* * * * *

UNITED STATES PATENT AND TRADEMARK OFFICE

CERTIFICATE OF CORRECTION

PATENT NO. : 5,686,590

DATED : November 11, 1997

INVENTOR(S) : William R. Jacobs, Jr., et al.

It is certified that error appears in the above-identified patent and that said Letters Patent is hereby corrected as shown below:

*Column 3, line 54:* please change "mc² 155" to -- mc²155 --.

*Column 13, line 36:* please change "Immulon™1" to -- Immulon™ --.

*Column 18, line 48:* please change "contransformed" to -- cotransformed --.

Signed and Sealed this

Tenth Day of February, 1998

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 1723 base pairs
( B ) TYPE: nucleic acid
( C ) STRANDEDNESS: single
( D ) TOPOLOGY: linear ( x i ) SEQUENCE DESCRIPTION: SEQ ID NO:1:

```
GGATCCGTCA TGGTCGAAGT GTGCTGAGTC ACACCGACAA ACGTCACGAG CGTAACCCCA     60
GTGCGAAAGT TCCCGCCGGA AATCGCAGCC ACGTTACGCT CGTGGACATA CCGATTTCGG    120
CCCGGCCGCG GCGAGACGAT AGGTTGTCGG GGTGACTGCC ACAGCCACTG AAGGGGCCAA    180
ACCCCCATTC GTATCCCGTT CAGTCCTGGT TACCGGAGGA AACCGGGGGA TCGGGCTGGC    240
GATCGCACAG CGGCTGGCTG CCGACGGCCA CAAGGTGGCC GTCACCCACC GTGGATCCGG    300
AGCGCAAAGG GGCTGTTTGG CGTCGAATGT GACGTCACCG ACAGCGACGC CGTCGATCGC    360
GCCTTCACGG CGGTAGAAGA GCACCAGGGT CCGGTCGAGG TGCTGGTGTC CAACGCCGGC    420
CTATCCGCGG ACGCATTCCT CATGCGGATG ACCGAGGAAA AGTTCGAGAA GGTCATCAAC    480
GCCAACCTCA CCGGGGCGTT CCGGGTGGCT CAACGGGCAT CGCGCAGCAT GCAGCGCAAC    540
AAATTCGGTC GAATGATATT CATAGGTTCG GTCTCCGGCA GCTGGGGCAT CGGCAACCAG    600
GCCAACTACG CAGCCTCCAA GGCCGGAGTG ATTGGCATGG CCCGCTCGAT CGCCCGCGAG    660
CTGTCGAAGG CAAACGTGAC CGCGAATGTG GTGGCCCCGG GCTACATCGA CACCGATATG    720
ACCCGCGCGC TGGATGAGCG GATTCAGCAG GGGGCGCTGC AATTTATCCC AGCGAAGCGG    780
GTCGGCACCC CCGCCGAGGT CGCCGGGGTG GTCAGCTTCC TGGCTTCCGA GGATGCGAGC    840
TATATCTCCG GTGCGGTCAT CCCGGTCGAC GGCGGCATGG GTATGGGCCA CTGACACAAC    900
ACAAGGACGC ACATGACAGG ACTGCTGGAC GGCAAACGGA TTCTGGTTAG CGGAATCATC    960
ACCGACTCGT CGATCGCGTT TCACATCGCA CGGGTAGCCC AGGAGCAGGG CGCCCAGCTG   1020
GTGCTCACCG GGTTCGACCG GCTGCGGCTG ATTCAGCGCA TCACCGACCG GCTGCCGGCA   1080
AAGGCCCCCG CTGCTCGAAC TCGACGTGCA AAACGAGGAG CACCTGGCCA GCTTGGCCGG   1140
```

-continued

```
CCGGGTGACC GAGGCGATCG GGGCGGGCAA CAAGCTCGAC GGGGTGGTGC ATTTCGATTG    1200
GGTTCATGCC GCAGACCGGG ATGGGCATCA ACCCGTTCTT CGACGCGCCC TACGCGGATG    1260
TGTCCAAGGG CATCCACATC TCGGCGTATT CGTATGCTTC GATGGCCAAG GCGCTGCTGC    1320
CGATCATGAA CCCCGGAGGT TCCATCGTCG GCATGGACTT CGACCCGAGC CGGGCGATGC    1380
CGGCCTACAA CTGGATGACG GTCGCCAAGA GCGCGTTGGA GTCGGTCAAC AGGTTCGTGG    1440
CGCGCGAGGC CGGCAAGTAC GGTGTGCGTT CGAATCTCGT TGCCGCAGGC CCTATCCGGA    1500
CGCTGGCGAT GAGTGCGATC GTCGGCGGTG CGCTGGCGAG GAGGCCGGCG CCCAGATCCA    1560
GCTGCTCGAG GAGGCTGGGA TCAGCGCGCT CCGATCGGCT GGAACATGAA GGATGCGACG    1620
CCGGTCGCCA AGACGGTGTG CGCGCTGCTG TCTGACTGGC TGCCGGCGAC CACGGGTGAC    1680
ATCATCTACG CCGACGGCGG CGCGCACACC CAATTGCTCT AGA                     1723
```

( 2 ) INFORMATION FOR SEQ ID NO:2:

( i ) SEQUENCE CHARACTERISTICS:
        ( A ) LENGTH: 1723 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
GGATCCGTCA TGGTCGAAGT GTGCTGAGTC ACACCGACAA ACGTCACGAG CGTAACCCCA     60
GTGCGAAAGT TCCCGCCGGA AATCGCAGCC ACGTTACGCT CGTGGACATA CCGATTTCGG    120
CCCGGCCGCG GCGAGACGAT AGGTTGTCGG GGTGACTGCC ACAGCCACTG AAGGGGCCAA    180
ACCCCCATTC GTATCCCGTT CAGTCCTGGT TACCGGAGGA AACCGGGGGA TCGGCTGGC    240
GATCGCACAG CGGCTGGCTG CCGACGGCCA CAAGGTGGCC GTCACCCACC GTGGATCCGG    300
AGCGCAAAGG GGCTGTTTGG CGTCGAATGT GACGTCACCG ACAGCGACGC CGTCGATCGC    360
GCCTTCACGG CGGTAGAAGA GCACCAGGGT CCGGTCGAGG TGCTGGTGTC CAACGCCGGC    420
CTATCCGCGG ACGCATTCCT CATGCGGATG ACCGAGGAAA AGTTCGAGAA GGTCATCAAC    480
GCCAACCTCA CCGGGGCGTT CCGGGTGGCT CAACGGGCAT CGCGCAGCAT GCAGCGCAAC    540
AAATTCGGTC GAATGATATT CATAGGTTCG GTCTCCGGCA GCTGGGGCAT CGGCAACCAG    600
GCCAACTACG CAGCCTCCAA GGCCGGAGTG ATTGGCATGG CCCGCTCGAT CGCCCGCGAG    660
CTGTCGAAGG CAAACGTGAC CGCGAATGTG GTGGCCCCGG GCTACATCGA CACCGATATG    720
ACCCGCGCGC TGGATGAGCG GATTCAGCAG GGGGCGCTGC AATTTATCCC AGCGAAGCGG    780
GTCGGCACCC CCGCCGAGGT CGCCGGGGTG GTCAGCTTCC TGGCTTCCGA GGATGCGAGC    840
TATATCTCCG GTGCGGTCAT CCCGGTCGAC GGCGGCATGG GTATGGGCCA CTGACACAAC    900
ACAAGGACGC ACATGACAGG ACTGCTGGAC GGCAAACGGA TTCTGGTTAG CGGAATCATC    960
ACCGACTCGT CGATCGCGTT TCACATCGCA CGGGTAGCCC AGGAGCAGGG CGCCCAGCTG   1020
GTGCTCACCG GGTTCGACCG GCTGCGGCTG ATTCAGCGCA TCACCGACCG GCTGCCGGCA   1080
AAGGCCCCCG CTGCTCGAAC TCGACGTGCA AAACGAGGAG CACCTGGCCA GCTTGGCCGG   1140
CCGGGTGACC GAGGCGATCG GGCGGGCAA CAAGCTCGAC GGGGTGGTGC ATTGCGATTG   1200
GGTTCATGCC GCAGACCGGG ATGGGCATCA ACCCGTTCTT CGACGCGCCC TACGCGGATG   1260
TGTCCAAGGG CATCCACATC TCGGCGTATT CGTATGCTTC GATGGCCAAG GCGCTGCTGC   1320
CGATCATGAA CCCCGGAGGT TCCATCGTCG GCATGGACTT CGACCCGAGC CGGGCGATGC   1380
CGGCCTACAA CTGGATGACG GTCGCCAAGA GCGCGTTGGA GTCGGTCAAC AGGTTCGTGG   1440
CGCGCGAGGC CGGCAAGTAC GGTGTGCGTT CGAATCTCGT TGCCGCAGGC CCTATCCGGA   1500
```

| | | | | | |
|---|---|---|---|---|---|
| CGCTGGCGAT | GAGTGCGATC | GTCGGCGGTG | CGCTGGCGAG | GAGGCCGGCG | CCCAGATCCA | 1560 |
| GCTGCTCGAG | GAGGCTGGGA | TCAGCGCGCT | CCGATCGGCT | GGAACATGAA | GGATGCGACG | 1620 |
| CCGGTCGCCA | AGACGGTGTG | CGCGCTGCTG | TCTGACTGGC | TGCCGGCGAC | CACGGGTGAC | 1680 |
| ATCATCTACG | CCGACGGCGG | CGCGCACACC | CAATTGCTCT | AGA | | 1723 |

(2) INFORMATION FOR SEQ ID NO:3:

(i) SEQUENCE CHARACTERISTICS:
        (A) LENGTH: 1721 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1190
        (D) OTHER INFORMATION: /note="In mutant form mc2 651 this
           position is T."

(xi) SEQUENCE DESCRIPTION: SEQ ID NO:3:

| | | | | | |
|---|---|---|---|---|---|
| GGATCCGCCG | CACGGGAGC | CCCGAGGCGA | TTTCTGGCTG | GACCGGCCAA | CACGTTAAGT | 60 |
| TGACGGGCGA | AGACGCAGGA | CGCGAGGAAC | AGAGGATGAC | TGTGACTGAC | AATCCGGCCG | 120 |
| ACACCGCGGG | CGAGGCCACT | GCAGGCCGCC | CGGCGTTCGT | CTCCCGTTCG | GTGCTGGTGA | 180 |
| CCGGTGGTAA | CCGCGGCATC | GGCCTGGCGA | TCGCGCGACG | GCTGGCCGCC | GACGGGCACA | 240 |
| AGGTGGCCGT | CACCCACCGC | GGTTCCGGTG | CACCCGACGA | CCTGTTCGGT | GTTCAATGTG | 300 |
| ACGTCACCGA | CAGCGCTGGT | GTCGACCGCG | CCTTCAAAGA | GGTCGAGGAG | CACCAGGGCC | 360 |
| CGGTCGAGGT | GCTGGTGGCC | AACGCAGGCA | TCTCCAAGGA | CGCATTCCTC | ATGCGCATGA | 420 |
| CCGAGGAGCG | GTTCGAAGAG | GTCATCAACA | CCAACCTCAC | GGGCGCGTTC | CGGTGCGCCC | 480 |
| AGCGGGCGTC | GCGCACCATG | CAGCGCAAGC | GGTTCGGGCG | CATCATCTTC | ATCGGGTCGG | 540 |
| TCTCGGGCAT | GTGGGGATC | GGCAATCAGG | CCAACTACGC | GGCCGCCAAG | GCGGGCCTGA | 600 |
| TCGGCATGGC | CCGCTCGATC | TCCCGTGAGC | TGGACAAGGC | GGGCGTCACC | GCGAACGTGT | 660 |
| TGCCCCCCGG | TTACATCGAC | ACCGAGATGA | CCCGGGCGCT | CGACGAGCGC | ATCCAGGGGG | 720 |
| GCGCGATCGA | CTTCATCCCG | GACAAGCGGG | TCGGCACGGT | CGAGGAGGTC | GCGGGCGCGG | 780 |
| TCAGCTTCCT | GGCCTCGGAG | GACGCCTCCT | ACATCGCGGG | CGCGGTCATC | CCCGTCGACG | 840 |
| GCGGTATGGG | CATGGGCCAC | TAGTCAAAAG | CCCGGACACA | CAAGATTTCT | CGCTCACAAG | 900 |
| GAGTCACCAA | ATGACAGGAC | TACTCGAAGG | CAAGCGCATC | CTCGTCACGG | GGATCATCAC | 960 |
| CGATTCGTCG | ATCGCGTTCC | ACATCGCCAA | GGTCGCCCAG | GAGGCCGGTG | CCGAACTGGT | 1020 |
| GCTGACCGGT | TTCGACCGCC | TGAAGTTGGT | CAAGCGCATC | GCCGACCGCC | TGCCCAAGCC | 1080 |
| GGCCCCGCTG | CTGGAACTCG | ACGTGCAGAA | CGAGGAGCAC | CTGTCGACTC | TGGCCGACCG | 1140 |
| GATCACCGCC | GAGATCGGTG | AGGGCAACAA | GATCGACGGT | GTGGTGCACT | CGATCGGGTT | 1200 |
| CATGCCGCAG | AGCGGTATGG | GCATCAACCC | GTTCTTCGAC | GCGCCGTACG | AGGATGTGTC | 1260 |
| CAAGGGCATC | CACATCTCGG | CGTACTCGTA | CGCCTCGCTC | GCCAAAGCCG | TTCTGCCGAT | 1320 |
| CATGAATCCG | GGCGGTGGTA | TCGTCGGTAT | GGACTTCGAC | CCCACGCGCG | CGATGCCGGC | 1380 |
| CTACAACTGG | ATGACCGTCG | CCAAGAGCGC | GCTCGAATCG | GTCAACCGGT | TCGTCGCGCG | 1440 |
| TGAGGCGGGC | AAGGTGGGCG | TGCGCTCGAA | TCTCGTTGCG | GCAGGACCGA | TCCGCACGCT | 1500 |
| GGCGATGAGC | GCAATCGTGG | GCGGTGCGCT | GGGCGACGAG | GCCGGCCAGC | AGATGCAGCT | 1560 |
| GCTCGAAGAG | GGCTGGGATC | AGCGCGCGCC | GCTGGGCTGG | AACATGAAGG | ACCCGACGCC | 1620 |

CGTCGCCAAG ACCGTGTGCG CACTGCTGTC GGACTGGCTG CCGGCCACCA CCGGCACCGT    1680

GATCTACGCC GACGGCGGCG CCAGCACGCA GCTGTTGTGA T    1721

( 2 ) INFORMATION FOR SEQ ID NO:4:

( i ) SEQUENCE CHARACTERISTICS:
        ( A ) LENGTH: 269 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Met Thr Gly Leu Leu Asp Gly Lys Arg Ile Leu Val Ser Gly Ile Ile
1               5                   10                  15

Thr Asp Ser Ser Ile Ala Phe His Ile Ala Arg Val Ala Gln Glu Gln
                20                  25                  30

Gly Ala Gln Leu Val Leu Thr Gly Phe Asp Arg Leu Arg Leu Ile Gln
            35                  40                  45

Arg Ile Thr Asp Arg Leu Pro Ala Lys Ala Pro Leu Leu Glu Leu Asp
    50                  55                  60

Val Gln Asn Glu Glu His Leu Ala Ser Leu Ala Gly Arg Val Thr Glu
65                  70                  75                  80

Ala Ile Gly Ala Gly Asn Lys Leu Asp Gly Val Val His Ser Ile Gly
                85                  90                  95

Phe Met Pro Gln Thr Gly Met Gly Ile Asn Pro Phe Phe Asp Ala Pro
            100                 105                 110

Tyr Ala Asp Val Ser Lys Gly Ile His Ile Ser Ala Tyr Ser Tyr Ala
        115                 120                 125

Ser Met Ala Lys Ala Leu Leu Pro Ile Met Asn Pro Gly Gly Ser Ile
    130                 135                 140

Val Gly Met Asp Phe Asp Pro Ser Arg Ala Met Pro Ala Tyr Asn Trp
145                 150                 155                 160

Met Thr Val Ala Lys Ser Ala Leu Glu Ser Val Asn Arg Phe Val Ala
                165                 170                 175

Arg Glu Ala Gly Lys Tyr Gly Val Arg Ser Asn Leu Val Gly Ala Gly
            180                 185                 190

Pro Ile Arg Thr Leu Ala Met Ser Ala Ile Val Gly Gly Ala Leu Gly
        195                 200                 205

Glu Glu Ala Gly Ala Gln Ile Gln Leu Leu Glu Glu Gly Trp Asp Gln
    210                 215                 220

Arg Ala Pro Ile Gly Trp Asn Met Lys Asp Ala Thr Pro Val Ala Lys
225                 230                 235                 240

Thr Val Cys Ala Leu Leu Ser Asp Trp Leu Pro Ala Thr Thr Gly Asp
                245                 250                 255

Ile Ile Tyr Ala Asp Gly Gly Ala His Thr Gln Leu Leu
            260                 265
```

( 2 ) INFORMATION FOR SEQ ID NO:5:

( i ) SEQUENCE CHARACTERISTICS:
        ( A ) LENGTH: 269 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Met Thr Gly Leu Leu Asp Gly Lys Arg Ile Leu Val Ser Gly Ile Ile
1               5                   10                  15
```

```
Thr  Asp  Ser  Ser  Ile  Ala  Phe  His  Ile  Ala  Arg  Val  Ala  Gln  Glu  Gln
               20                  25                       30

Gly  Ala  Gln  Leu  Val  Leu  Thr  Gly  Phe  Asp  Arg  Leu  Arg  Leu  Ile  Gln
          35                       40                  45

Arg  Ile  Thr  Asp  Arg  Leu  Pro  Ala  Lys  Ala  Pro  Leu  Leu  Glu  Leu  Asp
     50                  55                       60

Val  Gln  Asn  Glu  Glu  His  Leu  Ala  Ser  Leu  Ala  Gly  Arg  Val  Thr  Glu
65                       70                  75                            80

Ala  Ile  Gly  Ala  Gly  Asn  Lys  Leu  Asp  Gly  Val  Val  His  Ala  Ile  Gly
               85                       90                            95

Phe  Met  Pro  Gln  Thr  Gly  Met  Gly  Ile  Asn  Pro  Phe  Phe  Asp  Ala  Pro
               100                      105                           110

Tyr  Ala  Asp  Val  Ser  Lys  Gly  Ile  His  Ile  Ser  Ala  Tyr  Ser  Tyr  Ala
          115                      120                      125

Ser  Met  Ala  Lys  Ala  Leu  Leu  Pro  Ile  Met  Asn  Pro  Gly  Gly  Ser  Ile
     130                      135                 140

Val  Gly  Met  Asp  Phe  Asp  Pro  Ser  Arg  Ala  Met  Pro  Ala  Tyr  Asn  Trp
145                      150                      155                      160

Met  Thr  Val  Ala  Lys  Ser  Ala  Leu  Glu  Ser  Val  Asn  Arg  Phe  Val  Ala
                165                      170                      175

Arg  Glu  Ala  Gly  Lys  Tyr  Gly  Val  Arg  Ser  Asn  Leu  Val  Ala  Ala  Gly
               180                      185                      190

Pro  Ile  Arg  Thr  Leu  Ala  Met  Ser  Ala  Ile  Val  Gly  Gly  Ala  Leu  Gly
          195                      200                 205

Glu  Glu  Ala  Gly  Ala  Gln  Ile  Gln  Leu  Leu  Glu  Glu  Gly  Trp  Asp  Gln
     210                      215                      220

Arg  Ala  Pro  Ile  Gly  Trp  Asn  Met  Lys  Asp  Ala  Thr  Pro  Val  Ala  Lys
225                      230                      235                      240

Thr  Val  Cys  Ala  Leu  Leu  Ser  Asp  Trp  Leu  Pro  Ala  Thr  Thr  Gly  Asp
                     245                      250                 255

Ile  Ile  Tyr  Ala  Asp  Gly  Gly  Ala  His  Thr  Gln  Leu  Leu
               260                      265
```

( 2 ) INFORMATION FOR SEQ ID NO:6:

( i ) SEQUENCE CHARACTERISTICS:
        ( A ) LENGTH: 269 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Met  Thr  Gly  Leu  Leu  Glu  Gly  Lys  Arg  Ile  Leu  Val  Thr  Gly  Ile  Ile
1                   5                        10                           15

Thr  Asp  Ser  Ser  Ile  Ala  Phe  His  Ile  Ala  Lys  Val  Ala  Gln  Glu  Ala
               20                       25                      30

Gly  Ala  Glu  Leu  Val  Leu  Thr  Gly  Phe  Asp  Arg  Leu  Lys  Leu  Val  Lys
          35                       40                  45

Arg  Ile  Ala  Asp  Arg  Leu  Pro  Lys  Pro  Ala  Pro  Leu  Leu  Glu  Leu  Asp
     50                  55                       60

Val  Gln  Asn  Glu  Glu  His  Leu  Ser  Thr  Leu  Ala  Asp  Arg  Ile  Thr  Ala
65                       70                  75                            80

Glu  Ile  Gly  Glu  Gly  Asn  Lys  Ile  Asp  Gly  Val  Val  His  Ser  Ile  Gly
               85                       90                            95

Phe  Met  Pro  Gln  Ser  Gly  Met  Gly  Ile  Asn  Pro  Phe  Phe  Asp  Ala  Pro
               100                      105                           110
```

```
Tyr Glu Asp Val Ser Lys Gly Ile His Ile Ser Ala Tyr Ser Tyr Ala
    115             120                 125

Ser Leu Ala Lys Ala Val Leu Pro Ile Met Asn Pro Gly Gly Gly Ile
    130             135                 140

Val Gly Met Asp Phe Asp Pro Thr Arg Ala Met Pro Ala Tyr Asn Trp
145             150                 155                     160

Met Thr Val Ala Lys Ser Ala Leu Glu Ser Val Asn Arg Phe Val Ala
                165                 170                 175

Arg Glu Ala Gly Lys Val Gly Val Arg Ser Asn Leu Val Ala Ala Gly
            180                 185                 190

Pro Ile Arg Thr Leu Ala Met Ser Ala Ile Val Gly Gly Ala Leu Gly
        195                 200                 205

Asp Glu Ala Gly Gln Gln Met Gln Leu Leu Glu Glu Gly Trp Asp Gln
    210             215                 220

Arg Ala Pro Leu Gly Trp Asn Met Lys Asp Pro Thr Pro Val Ala Lys
225             230                 235                     240

Thr Val Cys Ala Leu Leu Ser Asp Trp Leu Pro Ala Thr Thr Gly Thr
                245                 250                 255

Val Ile Tyr Ala Asp Gly Gly Ala Ser Thr Gln Leu Leu
            260                 265
```

( 2 ) INFORMATION FOR SEQ ID NO:7:

( i ) SEQUENCE CHARACTERISTICS:
        ( A ) LENGTH: 269 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Met Thr Gly Leu Leu Glu Gly Lys Arg Ile Leu Val Thr Gly Ile Ile
1               5                   10                  15

Thr Asp Ser Ser Ile Ala Phe His Ile Ala Lys Val Ala Gln Glu Ala
            20                  25                  30

Gly Ala Glu Leu Val Leu Thr Gly Phe Asp Arg Leu Lys Leu Val Lys
            35                  40                  45

Arg Ile Ala Asp Arg Leu Pro Lys Pro Ala Pro Leu Leu Glu Leu Asp
    50                  55                  60

Val Gln Asn Glu Glu His Leu Ser Thr Leu Ala Asp Arg Ile Thr Ala
65                  70                  75                  80

Glu Ile Gly Glu Gly Asn Lys Ile Asp Gly Val Val His Ala Ile Gly
                85                  90                  95

Phe Met Pro Gln Ser Gly Met Gly Ile Asn Pro Phe Phe Asp Ala Pro
            100                 105                 110

Tyr Glu Asp Val Ser Lys Gly Ile His Ile Ser Ala Tyr Ser Tyr Ala
    115                 120                 125

Ser Leu Ala Lys Ala Val Leu Pro Ile Met Asn Pro Gly Gly Gly Ile
    130                 135                 140

Val Gly Met Asp Phe Asp Pro Thr Arg Ala Met Pro Ala Tyr Asn Trp
145             150                 155                     160

Met Thr Val Ala Lys Ser Ala Leu Glu Ser Val Asn Arg Phe Val Ala
                165                 170                 175

Arg Glu Ala Gly Lys Val Gly Val Arg Ser Asn Leu Val Ala Ala Gly
            180                 185                 190

Pro Ile Arg Thr Leu Ala Met Ser Ala Ile Val Gly Gly Ala Leu Gly
        195                 200                 205
```

|     |     |     |     |     |     |     |     |     |     |     |     |     |     |     |
|-----|-----|-----|-----|-----|-----|-----|-----|-----|-----|-----|-----|-----|-----|-----|
| Asp | Glu | Ala | Gly | Gln | Gln | Met | Gln | Leu | Leu | Glu | Glu | Gly | Trp | Asp | Gln |
|     | 210 |     |     |     |     | 215 |     |     |     |     | 220 |     |     |     |     |
| Arg | Ala | Pro | Leu | Gly | Trp | Asn | Met | Lys | Asp | Pro | Thr | Pro | Val | Ala | Lys |
| 225 |     |     |     |     | 230 |     |     |     |     | 235 |     |     |     |     | 240 |
| Thr | Val | Cys | Ala | Leu | Leu | Ser | Asp | Trp | Leu | Pro | Ala | Thr | Thr | Gly | Thr |
|     |     |     |     | 245 |     |     |     |     | 250 |     |     |     |     | 255 |     |
| Val | Ile | Tyr | Ala | Asp | Gly | Gly | Ala | Ser | Thr | Gln | Leu | Leu |     |     |     |
|     |     |     |     | 260 |     |     |     | 265 |     |     |     |     |     |     |     |

( 2 ) INFORMATION FOR SEQ ID NO:8:

( i ) SEQUENCE CHARACTERISTICS:
        ( A ) LENGTH: 262 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Gly | Phe | Leu | Ser | Gly | Lys | Arg | Ile | Leu | Val | Thr | Gly | Val | Ala | Ser |
| 1   |     |     |     | 5   |     |     |     |     | 10  |     |     |     |     | 15  |     |
| Lys | Leu | Ser | Ile | Ala | Tyr | Gly | Ile | Ala | Gln | Ala | Met | His | Arg | Glu | Gly |
|     |     |     | 20  |     |     |     |     | 25  |     |     |     |     | 30  |     |     |
| Ala | Glu | Leu | Ala | Phe | Thr | Tyr | Gln | Asn | Asp | Lys | Leu | Lys | Gly | Arg | Val |
|     |     |     | 35  |     |     |     | 40  |     |     |     |     | 45  |     |     |     |
| Glu | Glu | Phe | Ala | Ala | Gln | Leu | Gly | Ser | Ser | Ile | Val | Leu | Pro | Cys | Asp |
|     | 50  |     |     |     |     | 55  |     |     |     |     | 60  |     |     |     |     |
| Val | Ala | Glu | Asp | Ala | Ser | Ile | Asp | Ala | Met | Phe | Ala | Glu | Leu | Gly | Asn |
| 65  |     |     |     |     | 70  |     |     |     |     | 75  |     |     |     |     | 80  |
| Val | Trp | Pro | Lys | Phe | Asp | Gly | Phe | Val | His | Ser | Ile | Gly | Phe | Ala | Pro |
|     |     |     |     | 85  |     |     |     |     | 90  |     |     |     |     | 95  |     |
| Gly | Asp | Gln | Leu | Asp | Gly | Asp | Tyr | Val | Asn | Ala | Val | Thr | Arg | Glu | Gly |
|     |     |     | 100 |     |     |     |     | 105 |     |     |     |     | 110 |     |     |
| Phe | Lys | Val | Ala | His | Asp | Ile | Ser | Ser | Tyr | Ser | Phe | Val | Ala | Met | Ala |
|     |     | 115 |     |     |     |     | 120 |     |     |     |     | 125 |     |     |     |
| Lys | Ala | Cys | Arg | Thr | Met | Leu | Asn | Pro | Gly | Ser | Ala | Leu | Leu | Thr | Leu |
|     | 130 |     |     |     |     | 135 |     |     |     |     | 140 |     |     |     |     |
| Ser | Tyr | Leu | Gly | Ala | Glu | Arg | Ala | Ile | Pro | Asn | Tyr | Asn | Val | Met | Gly |
| 145 |     |     |     |     | 150 |     |     |     |     | 155 |     |     |     |     | 160 |
| Leu | Ala | Lys | Ala | Ser | Leu | Glu | Ala | Asn | Val | Arg | Tyr | Met | Ala | Asn | Ala |
|     |     |     |     | 165 |     |     |     |     | 170 |     |     |     |     | 175 |     |
| Met | Gly | Pro | Glu | Gly | Val | Arg | Val | Asn | Ala | Ile | Ser | Ala | Gly | Pro | Ile |
|     |     |     | 180 |     |     |     |     | 185 |     |     |     |     | 190 |     |     |
| Arg | Thr | Leu | Ala | Ala | Ser | Gly | Ile | Lys | Asp | Phe | Arg | Lys | Met | Leu | Ala |
|     |     | 195 |     |     |     |     | 200 |     |     |     |     | 205 |     |     |     |
| His | Cys | Glu | Ala | Val | Thr | Pro | Ile | Arg | Arg | Thr | Val | Thr | Ile | Glu | Asp |
|     | 210 |     |     |     |     | 215 |     |     |     |     | 220 |     |     |     |     |
| Val | Gly | Asn | Ser | Ala | Ala | Phe | Leu | Cys | Ser | Asp | Leu | Ser | Ala | Gly | Ile |
| 225 |     |     |     |     | 230 |     |     |     |     | 235 |     |     |     |     | 240 |
| Ser | Gly | Glu | Val | Val | His | Val | Asp | Gly | Gly | Phe | Ser | Ile | Ala | Ala | Met |
|     |     |     |     | 245 |     |     |     |     | 250 |     |     |     |     | 255 |     |
| Asn | Glu | Leu | Glu | Leu | Lys |     |     |     |     |     |     |     |     |     |     |
|     |     |     | 260 |     |     |     |     |     |     |     |     |     |     |     |     |

( 2 ) INFORMATION FOR SEQ ID NO:9:

( i ) SEQUENCE CHARACTERISTICS:
        ( A ) LENGTH: 262 amino acids
        ( B ) TYPE: amino acid (C) STRANDEDNESS: single
(D) TOPOLOGY: linear (xi) SEQUENCE DESCRIPTION: SEQ ID NO:9:

| Met | Gly | Phe | Leu | Ser | Gly | Lys | Arg | Ile | Leu | Val | Thr | Gly | Val | Ala | Ser |
| 1 | | | | 5 | | | | | 10 | | | | | 15 | |

| Lys | Leu | Ser | Ile | Ala | Tyr | Gly | Ile | Ala | Gln | Ala | Met | His | Arg | Glu | Gly |
| | | | 20 | | | | | 25 | | | | | 30 | | |

| Ala | Glu | Leu | Ala | Phe | Thr | Tyr | Gln | Asn | Asp | Lys | Leu | Lys | Gly | Arg | Val |
| | | 35 | | | | | 40 | | | | | 45 | | | |

| Glu | Glu | Phe | Ala | Ala | Gln | Leu | Gly | Ser | Asp | Ile | Val | Leu | Gln | Cys | Asp |
| | 50 | | | | | 55 | | | | | 60 | | | | |

| Val | Ala | Glu | Asp | Ala | Ser | Ile | Asp | Thr | Met | Phe | Ala | Glu | Leu | Gly | Lys |
| 65 | | | | | 70 | | | | | 75 | | | | | 80 |

| Val | Trp | Pro | Lys | Phe | Asp | Gly | Phe | Val | His | Ser | Ile | Gly | Phe | Ala | Pro |
| | | | | 85 | | | | | 90 | | | | | 95 | |

| Gly | Asp | Gln | Leu | Asp | Gly | Asp | Tyr | Val | Asn | Ala | Val | Thr | Arg | Glu | Gly |
| | | | 100 | | | | | 105 | | | | | 110 | | |

| Phe | Lys | Ile | Ala | His | Asp | Ile | Ser | Ser | Tyr | Ser | Phe | Val | Ala | Met | Ala |
| | | 115 | | | | | 120 | | | | | 125 | | | |

| Lys | Ala | Cys | Arg | Ser | Met | Leu | Asn | Pro | Gly | Ser | Ala | Leu | Leu | Thr | Leu |
| | 130 | | | | | 135 | | | | | 140 | | | | |

| Ser | Tyr | Leu | Gly | Ala | Glu | Arg | Ala | Ile | Pro | Asn | Tyr | Asn | Val | Met | Gly |
| 145 | | | | | 150 | | | | | 155 | | | | | 160 |

| Leu | Ala | Lys | Ala | Ser | Leu | Glu | Ala | Asn | Val | Arg | Tyr | Met | Ala | Asn | Ala |
| | | | | 165 | | | | | 170 | | | | | 175 | |

| Met | Gly | Pro | Glu | Gly | Val | Arg | Val | Asn | Ala | Ile | Ser | Ala | Gly | Pro | Ile |
| | | | 180 | | | | | 185 | | | | | 190 | | |

| Arg | Thr | Leu | Ala | Ala | Ser | Gly | Ile | Lys | Asp | Phe | Arg | Lys | Met | Leu | Ala |
| | | 195 | | | | | 200 | | | | | 205 | | | |

| His | Cys | Glu | Ala | Val | Thr | Pro | Ile | Arg | Arg | Thr | Val | Thr | Ile | Glu | Asp |
| | 210 | | | | | 215 | | | | | 220 | | | | |

| Val | Gly | Asn | Ser | Ala | Ala | Phe | Leu | Cys | Ser | Asp | Leu | Ser | Ala | Gly | Ile |
| 225 | | | | | 230 | | | | | 235 | | | | | 240 |

| Ser | Gly | Glu | Val | Val | His | Val | Asp | Gly | Gly | Phe | Ser | Ile | Ala | Ala | Met |
| | | | | 245 | | | | | 250 | | | | | 255 | |

| Asn | Glu | Leu | Glu | Leu | Lys |
| | | | 260 | | |

(2) INFORMATION FOR SEQ ID NO:10:

(i) SEQUENCE CHARACTERISTICS:
(A) LENGTH: 3051 base pairs
(B) TYPE: nucleic acid
(C) STRANDEDNESS: single
(D) TOPOLOGY: linear (xi) SEQUENCE DESCRIPTION: SEQ ID NO:10:

```
GGATCCGCCG CACGGGAGC  CCCGAGGCGA TTTCTGGCTG GACCGGCCAA CACGTTAAGT    60
TGACGGGCGA AGACGCAGGA CGCGAGGAAC AGAGGATGAC TGTGACTGAC AATCCGGCCG   120
ACACCGCGGG CGAGGCCACT GCAGGCCGCC CGGCGTTCGT CTCCCGTTCG GTGCTGGTGA   180
CCGGTGGTAA CCGCGGCATC GGCCTGGCGA TCGCGCGACG GCTGGCCGCC GACGGGCACA   240
AGGTGGCCGT CACCACCGC  GGTTCCGGTG CACCCGACGA CCTGTTCGGT GTTCAATGTG   300
ACGTCACCGA CAGCGCTGGT GTCGACCGCG CCTTCAAAGA GGTCGAGGAG CACCAGGGCC   360
CGGTCGAGGT GCTGGTGGCC AACGCAGGCA TCTCCAAGGA CGCATTCCTC ATGCGCATGA   420
```

```
CCGAGGAGCG GTTCGAAGAG GTCATCAACA CCAACCTCAC GGGCGCGTTC CGGTGCGCCC    480
AGCGGGCGTC GCGCACCATG CAGCGCAAGC GGTTCGGGCG CATCATCTTC ATCGGGTCGG    540
TCTCGGGCAT GTGGGGATC  GGCAATCAGG CCAACTACGC GGCCGCCAAG GCGGGCCTGA    600
TCGGCATGGC CCGCTCGATC TCCCGTGAGC TGGACAAGGC GGGCGTCACC GCGAACGTGT    660
TGCCCCCCGG TTACATCGAC ACCGAGATGA CCCGGGCGCT CGACGAGCGC ATCCAGGGGG    720
GCGCGATCGA CTTCATCCCG GACAAGCGGG TCGGCACGGT CGAGGAGGTC GCGGGCGCGG    780
TCAGCTTCCT GGCCTCGGAG GACGCCTCCT ACATCGCGGG CGCGGTCATC CCCGTCGACG    840
GCGGTATGGG CATGGCCAC  TAGTCAAAAG CCCGGACACA CAAGATTTCT CGCTCACAAG    900
GAGTCACCAA ATGACAGGCC TACTCGAAGG CAAGCGCATC CTCGTCACGG GATCATCAC    960
CGATTCGTCG ATCGCGTTCC ACATCGCCAA GGTCGCCCAG GAGGCCGGCG CCGAACTGGT   1020
GCTGACCGGT TTCGACCGCC TGAAGTTGGT CAAGCGCATC GCCGACCGCC TGCCCAAGCC   1080
GGCCCCGCTG CTGGAACTCG ACGTGCAGAA CGAGGAGCAC CTGTCGACTC TGGCCGACCG   1140
GATCACCGCC GAGATCGGTG AGGGCAACAA GATCGACGGT GTGGTGCACG CGATCGGGTT   1200
CATGCCGCAG AGCGGTATGG GCATCAACCC GTTCTTCGAC GCGCCGTACG AGGATGTGTC   1260
CAAGGGCATC CACATCTCGG CGTACTCGTA CGCCTCGCTC GCCAAGCCG  TTCTGCCGAT   1320
CATGAATCCG GGCGGCGGCA TCGTCGGCAT GGACTTCGAC CCCACGCGCG CGATGCCGGC   1380
CTACAACTGG ATGACCGTCG CCAAGAGCGC GCTCGAATCG GTCAACCGGT TCGTCGCGCG   1440
TGAGGCGGGC AAGGTGGGCG TGCGCTCGAA TCTCGTTGCG GCAGGACCGA TCCGCACGCT   1500
GGCGATGAGC GCAATCGTGG GCGGTGCGCT GGGCGACGAG GCCGGCCAGC AGATGCAGCT   1560
GCTCGAAGAG GGCTGGGATC AGCGCGCGCC GCTGGGCTGG AACATGAAGG ACCCGACGCC   1620
CGTCGCCAAG ACCGTGTGCG CACTGCTGTC GGACTGGCTG CCGGCCACCA CCGGCACCGT   1680
GATCTACGCC GACGGCGGCG CCAGCACGCA GCTGTTGTGA TACCGCCGTG TCGTATGACG   1740
CCTTGCTACT GCTGTCGTTC GACGGGCCGG AACTCCCGAG CAGGTGATGC CGTTCTTGGA   1800
GAACTCACCA GGGGCCGCGG AATCCCCAGG GAGCGGCTGG AATCGGTGGC CGAGCACTAT   1860
CTGCACTTCG GCGGGGTGTC ACCGATCAAC GGCATCAACC GGGACCTGAT CGTCGCGATC   1920
GAGGCCGAAC TCGCCCGACG CGGCCGCAAC CTTCCGGTCT ACTTCGGCAA CCGCAACTGG   1980
GAGCCGTACG TCGAAGACAC TGTCAAGGCG ATGTCCGACA ACGGAATCCG TCGTGCGGCG   2040
GTGTTCGCGA CCTCGGCGTG GGGTGGGTAC TCGGGATGCG CCCAGTACCA GGAGGACATC   2100
GCGCGTGGCC GGGCCGCCGC CGGGCCCGAG GCGCCGGAGC TGGTCAAGCT GCGCCAGTAT   2160
TTCGACCACC CGCTGTTCGT CGAGATGTTC GCCGACGCCG TCGCCGACGC CGCGGCCACC   2220
CTGCCCGAGG AACTGCGGGA CGAAGCGCGG CTGGTGTTCA CCGCCCACTC CATCCCGCTG   2280
CGTGCCGCGT CGCGTTGCGG TGCAGATCTC TACGAGCGGC AGGTGGGTTA CGCCGCGCGG   2340
CTGGTCGCGG CCGCAGCCGG GTACCGCGAA TACGACCAGG TATGGCAGTC CCGGTCCGGC   2400
CCGCCGCAGG TGCCGTGGCT CGAACCCGAC GTCGGAGATC ACCTTGAGGC GTTGGCGCGC   2460
AACGGCACCA GGGCGGTCAT CGTGTGTCCC CTCGGCTTCG TCGCCGACCA CATCGAGGTG   2520
GTGTGGGATC TGGACAACGA ACTGGCCGAG CAGGCCGCCG AGGCAGGCAT CGCGTTCGCG   2580
CGTGCCGCCA CGCCCAACTC CCAGCCACGT TTTGCCCAAC TTGTCGTCGA CCTGATCGAC   2640
GAAATGCTGC ACGGACTTCC GCCACGCCGG GTCGAGGGGC CCGATCCGTG CCCGCCTACG   2700
GCAGCAGTGT CAACGGCGCA CCGTGCACGC CGGCCTGCTC GGCGTGACCC GCCCCGGGCG   2760
CAGCGAGTCG GGCCGGGCGA TCAAGAACGC CAGGCGGAAT GCAGGATCGC CTCGAGTGCG   2820
```

```
GCCATACGCG  CCGAGCGCAC  CACCCGCGTG  AGGGGGCGCA  GCGCCGAGTC  GGCGATCTGA    2880

ACCTCCGACG  AACTCTGCAG  ACCGCTCGGG  ATCAGACCCG  CACTCACCGC  GATGATGGCG    2940

TCGACATGGG  CGGCGTTCTC  CAGCACCCGC  ACAGCCCGGG  TCGGCGCGTG  GTCGGGGACG    3000

CGGTGCGCGC  GCCCGGCGGC  GAGGATCTGC  TCGACCATCC  CGCGCGGATC  C             3051
```

( 2 ) INFORMATION FOR SEQ ID NO:11:

( i ) SEQUENCE CHARACTERISTICS:
        ( A ) LENGTH: 3120 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
AGCGCGACAT  ACCTGCTGCG  CAATTCGTAG  GGCGTCAATA  CACCCGCAGC  CAGGGCCTCG      60

CTGCCCAGAA  AGGGATCCGT  CATGGTCGAA  GTGTGCTGAG  TCACACCGAC  AAACGTCACG     120

AGCGTAACCC  CAGTGCGAAA  GTTCCGCCG   GAAATCGCAG  CCACGTTACG  CTCGTGGACA     180

TACCGATTTC  GGCCCGGCCG  CGGCGAGACG  ATAGGTTGTC  GGGGTGACTG  CCACAGCCAC     240

TGAAGGGGCC  AAACCCCCAT  TCGTATCCCG  TTCAGTCCTG  GTTACCGGAG  GAAACCGGGG     300

GATCGGGCTG  GCGATCGCAC  AGCGGCTGGC  TGCCGACGGC  CACAAGGTGG  CCGTCACCCA     360

CCGTGGATCC  GGAGCGCCAA  AGGGGCTGTT  GGCGTCGAA   TGTGACGTCA  CCGACAGCGA     420

CGCCGTCGAT  CGCGCCTTCA  CGGCGGTAGA  AGAGCACCAG  GGTCCGGTCG  AGGTGCTGGT     480

GTCCAACGCC  GGCCTATCCG  CGGACGCATT  CCTCATGCGG  ATGACCGAGG  AAAAGTTCGA     540

GAAGGTCATC  AACGCCAACC  TCACCGGGGC  GTTCCGGGTG  GCTCAACGGG  CATCGCGCAG     600

CATGCAGCGC  AACAAATTCG  GTCGAATGAT  ATTCATAGGT  TCGGTCTCCG  GCAGCTGGGG     660

CATCGGCAAC  CAGGCCAACT  ACGCAGCCTC  CAAGGCCGGA  GTGATTGGCA  TGGCCCGCTC     720

GATCGCCCGC  GAGCTGTCGA  AGGCAAACGT  GACCGCGAAT  GTGGTGGCCC  CGGGCTACAT     780

CGACACCGAT  ATGACCCGCG  CGCTGGATGA  GCGGATTCAG  CAGGGGGCGC  TGCAATTTAT     840

CCCAGCGAAG  CGGGTCGGCA  CCCCCGCCGA  GGTCGCCGGG  GTGGTCAGCT  TCCTGGCTTC     900

CGAGGATGCG  AGCTATATCT  CCGGTGCGGT  CATCCCGGTC  GACGGCGGCA  TGGGTATGGG     960

CCACTGACAC  AACACAAGGA  CGCACATGAC  AGGACTGCTG  GACGGCAAAC  GGATTCTGGT    1020

TAGCGGAATC  ATCACCGACT  CGTCGATCGC  GTTCACATC   GCACGGGTAG  CCCAGGAGCA    1080

GGGCGCCCAG  CTGGTGCTCA  CCGGGTTCGA  CCGGCTGCGG  CTGATTCAGC  GCATCACCGA    1140

CCGGCTGCCG  GCAAAGGCCC  CGCTGCTCGA  ACTCGACGTG  CAAAACGAGG  AGCACCTGGC    1200

CAGCTTGGCC  GGCCGGGTGA  CCGAGGCGAT  CGGGCGGGC   AACAAGCTCG  ACGGGTGGT     1260

GCATTCGATT  GGGTTCATGC  CGCAGACCGG  GATGGGCATC  AACCCGTTCT  CGACGCGCC    1320

CTACGCGGAT  GTGTCCAAGG  GCATCCACAT  CTCGGCGTAT  TCGTATGCTT  CGATGGCCAA    1380

GGCGCTGCTG  CCGATCATGA  ACCCCGGAGG  TTCCATCGTC  GGCATGGACT  CGACCCGAG    1440

CCGGGCGATG  CCGGCCTACA  ACTGGATGAC  GGTCGCCAAG  AGCGCGTTGG  AGTCGGTCAA    1500

CAGGTTCGTG  GCGCGCGAGG  CCGGCAAGTA  CGGTGTGCGT  TCGAATCTCG  TTGGCGCAGG    1560

CCCTATCCGG  ACGCTGGCGA  TGAGTGCGAT  CGTCGGCGGT  GCGCTCGGCG  AAGAGGCCGG    1620

CGCCCAGATC  CAGCTGCTCG  AGGAGGGCTG  GGATCAGCGC  GCTCCGATCG  GCTGGAACAT    1680

GAAGGATGCG  ACGCCGGTCG  CCAAGACGGT  GTGCGCGCTG  CTGTCTGACT  GGCTGCCGGC    1740

GACCACGGGT  GACATCATCT  ACGCCGACGG  CGGCGCGCAC  ACCCAATTGC  TCTAGAACGC    1800
```

-continued

| | | | | | |
|---|---|---|---|---|---|
| ATGCAATTTG | ATGCCGTCCT | GCTGCTGTCG | TTCGGCGGAC | CGGAAGGGCC | CGAGCAGGTG | 1860 |
| CGCCCGTTCC | TGGAGAACGT | TACCCGGGGC | CGCGGTGTGC | CTGCCGAACG | GTTGGACGCG | 1920 |
| GTGGCCGAGC | ACTACCTGCA | TTTCGGTGGG | GTATCACCGA | TCAATGGCAT | TAATCGCACA | 1980 |
| CTGATCGCGG | AGCTGGAGGC | GCAGCAAGAA | CTGCCGGTGT | ACTTCGGTAA | CCGCAACTGG | 2040 |
| GAGCCGTATG | TAGAAGATGC | CGTTACGGCC | ATGCGCGACA | ACGGTGTCCG | GCGTGCAGCG | 2100 |
| GTCTTTGCGA | CATCTGCGTG | GAGCGGTTAC | TCGAGCTGCA | CACAGTACGT | GGAGGACATC | 2160 |
| GCGCGGCCCC | CCGCGCGGCC | GGGCGCGACG | CGCCTGAACT | GGTAAAACTG | CGGCCCTACT | 2220 |
| TCGACCATCC | GCTGTTCGTC | GAGATGTTCG | CCGACGCCAT | CACCGCGGCC | GCCGCAACCG | 2280 |
| TGCGCGGTGA | TGCCCGGCTG | GTGTTCACCG | CGCATTCGAT | CCCGACGGCC | GCCGACCGCC | 2340 |
| GCTGTGGCCC | CAACCTCTAC | AGCCGCCAAG | TCGCCTACGC | CACAAGGCTG | GTCGCGGCCG | 2400 |
| CTGCCGGATA | CTGCGACTTT | GACCTGGCCT | GGCAGTCGAG | ATCGGGCCCG | CCGCAGGTGC | 2460 |
| CCTGGCTGGA | GCCAGACGTT | ACCGACCAGC | TCACCGGTCT | GGCTGGGGCC | GGCATCAACG | 2520 |
| CGGTGATCGT | GTGTCCCATT | GGATTCGTCG | CCGACCATAT | CGAGGTGGTG | TGGGATCTCG | 2580 |
| ACCACGAGTT | GCGATTACAA | GCCGAGGCAG | CGGGCATCGC | GTACGCCCGG | GCCAGCACCC | 2640 |
| CCAATGCCGA | CCCGCGGTTC | GCTCGACTAG | CCAGAGGTTT | GATCGACGAA | CTCCGTTACG | 2700 |
| GCCGTATACC | TGCGCGGGTG | AGTGGCCCCG | ATCCGGTGCC | GGGCTGTCTG | TCCAGCATCA | 2760 |
| ACGGCCAGCC | ATGCCGTCCG | CCGCACTGCG | TGGCTAGCGT | CAGTCCGGCC | AGGCCGAGTG | 2820 |
| CAGGATCGCC | GTGACCGCGG | ACATCCGGGC | CGAGCGCACC | ACGGCGGTCA | ACGGTCTCAA | 2880 |
| CGCATCGGTG | GCACGCTGAG | CGTCCGACAA | CGACTGCGTT | CCGATCGGCA | ATCGACTCAG | 2940 |
| CCCGGCACTG | ACCGCGATGA | TCGCATCGAC | GTGCGCGGCA | TTCTCGAGCA | CCCGCAATGC | 3000 |
| GCGCGATGGC | GCGTGGTCGG | GAACCCGGTG | TTGCCGTGAC | GATTCGAGCA | ACTGCTCGAC | 3060 |
| GAGGCCACGG | GGCTTGGCGA | CGTCGCTAGA | TCCCAGTCCG | ATGGTGCTCA | AGGCTTCGGC | 3120 |

( 2 ) INFORMATION FOR SEQ ID NO:12:

( i ) SEQUENCE CHARACTERISTICS:
        ( A ) LENGTH: 2232 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 494..1234

( i x ) FEATURE:
        ( A ) NAME/KEY: CDS
        ( B ) LOCATION: 1256..2062

( x i ) SEQUENCE DESCRIPTION: SEQ ID NO:12:

| | | | | | |
|---|---|---|---|---|---|
| GTTCGCTCCG | GCGCGGTCAC | GCGCATGCCC | TCGATGACGC | AGATCTCGTC | GGGCTCGATG | 60 |
| CGCTCTTCCC | AGACTTGCAG | CCCCGGGGCA | CGGCGGCGGT | TGGTGTCGAT | GATCGCGGCG | 120 |
| GGAAGATCCG | CGTCGATCCA | CTTGGCGCCA | TGGAAGGCAG | AAGCCGAGTA | GCCGGCCAGC | 180 |
| ACGCCGCGGC | GGCGCGAGCG | CAGCCACAGC | GCTTTTGCAC | GCAATTGCGC | GGTCAGTTCC | 240 |
| ACACCCTGCG | GCACGTACAC | GTCTTTATGT | AGCGCGACAT | ACCTGCTGCG | CAATTCGTAG | 300 |
| GGCGTCAATA | CACCCGCAGC | CAGGGCCTCG | CTGCCCAGAA | AGGGATCCGT | CATGGTCGAA | 360 |
| GTGTGCTGAG | TCACACCGAC | AAACGTCACG | AGCGTAACCC | CAGTGCGAAA | GTTCCCGCCG | 420 |
| GAAATCGCAG | CCACGTTACG | CTCGTGGACA | TACCGATTTC | GGCCCGGCCG | CGGCGAGACG | 480 |
| ATAGGTTGTC | GGG GTG ACT GCC ACA GCC ACT GAA GGG GCC AAA CCC CCA | | | | | 529 |

```
              Val Thr Ala Thr Ala Thr Glu Gly Ala Lys Pro Pro
               1               5                   10
TTC GTA TCC CGT TCA GTC CTG GTT ACC GGA GGA AAC CGG GGG ATC GGG        577
Phe Val Ser Arg Ser Val Leu Val Thr Gly Gly Asn Arg Gly Ile Gly
     15              20                  25

CTG GCG ATC GCA CAG CGG CTG GCT GCC GAC GGC CAC AAG GTG GCC GTC        625
Leu Ala Ile Ala Gln Arg Leu Ala Ala Asp Gly His Lys Val Ala Val
     30              35                  40

ACC CAC CGT GGA TCC GGA GCG CCA AAG GGG CTG TTT GGC GTC GAA TGT        673
Thr His Arg Gly Ser Gly Ala Pro Lys Gly Leu Phe Gly Val Glu Cys
 45              50                  55                      60

GAC GTC ACC GAC AGC GAC GCC GTC GAT CGC GCC TTC ACG GCG GTA GAA        721
Asp Val Thr Asp Ser Asp Ala Val Asp Arg Ala Phe Thr Ala Val Glu
                 65                  70                  75

GAG CAC CAG GGT CCG GTC GAG GTG CTG GTG TCC AAC GCC GGC CTA TCC        769
Glu His Gln Gly Pro Val Glu Val Leu Val Ser Asn Ala Gly Leu Ser
             80                  85                  90

GCG GAC GCA TTC CTC ATG CGG ATG ACC GAG GAA AAG TTC GAG AAG GTC        817
Ala Asp Ala Phe Leu Met Arg Met Thr Glu Glu Lys Phe Glu Lys Val
         95                  100                 105

ATC AAC GCC AAC CTC ACC GGG GCG TTC CGG GTG GCT CAA CGG GCA TCG        865
Ile Asn Ala Asn Leu Thr Gly Ala Phe Arg Val Ala Gln Arg Ala Ser
     110                 115                 120

CGC AGC ATG CAG CGC AAC AAA TTC GGT CGA ATG ATA TTC ATA GGT TCG        913
Arg Ser Met Gln Arg Asn Lys Phe Gly Arg Met Ile Phe Ile Gly Ser
 125                 130                 135                 140

GTC TCC GGC AGC TGG GGC ATC GGC AAC CAG GCC AAC TAC GCA GCC TCC        961
Val Ser Gly Ser Trp Gly Ile Gly Asn Gln Ala Asn Tyr Ala Ala Ser
             145                 150                 155

AAG GCC GGA GTG ATT GGC ATG GCC CGC TCG ATC GCC CGC GAG CTG TCG       1009
Lys Ala Gly Val Ile Gly Met Ala Arg Ser Ile Ala Arg Glu Leu Ser
         160                 165                 170

AAG GCA AAC GTG ACC GCG AAT GTG GTG GCC CCG GGC TAC ATC GAC ACC       1057
Lys Ala Asn Val Thr Ala Asn Val Val Ala Pro Gly Tyr Ile Asp Thr
     175                 180                 185

GAT ATG ACC CGC GCG CTG GAT GAG CGG ATT CAG CAG GGG GCG CTG CAA       1105
Asp Met Thr Arg Ala Leu Asp Glu Arg Ile Gln Gln Gly Ala Leu Gln
 190                 195                 200

TTT ATC CCA GCG AAG CGG GTC GGC ACC CCC GCC GAG GTC GCC GGG GTG       1153
Phe Ile Pro Ala Lys Arg Val Gly Thr Pro Ala Glu Val Ala Gly Val
 205                 210                 215                 220

GTC AGC TTC CTG GCT TCC GAG GAT GCG AGC TAT ATC TCC GGT GCG GTC       1201
Val Ser Phe Leu Ala Ser Glu Asp Ala Ser Tyr Ile Ser Gly Ala Val
             225                 230                 235

ATC CCG GTC GAC GGC GGC ATG GGT ATG GGC CAC TGACACAACA CAAGGACGCA     1254
Ile Pro Val Asp Gly Gly Met Gly Met Gly His
         240                 245

C ATG ACA GGA CTG CTG GAC GGC AAA CGG ATT CTG GTT AGC GGA ATC         1300
  Met Thr Gly Leu Leu Asp Gly Lys Arg Ile Leu Val Ser Gly Ile
   1               5                   10                  15

ATC ACC GAC TCG TCG ATC GCG TTT CAC ATC GCA CGG GTA GCC CAG GAG       1348
Ile Thr Asp Ser Ser Ile Ala Phe His Ile Ala Arg Val Ala Gln Glu
             20                  25                  30

CAG GGC GCC CAG CTG GTG CTC ACC GGG TTC GAC CGG CTG CGG CTG ATT       1396
Gln Gly Ala Gln Leu Val Leu Thr Gly Phe Asp Arg Leu Arg Leu Ile
         35                  40                  45

CAG CGC ATC ACC GAC CGG CTG CCG GCA AAG GCC CCG CTG CTC GAA CTC       1444
Gln Arg Ile Thr Asp Arg Leu Pro Ala Lys Ala Pro Leu Leu Glu Leu
     50                  55                  60

GAC GTG CAA AAC GAG GAG CAC CTG GCC AGC TTG GCC GGC CGG GTG ACC       1492
```

| | | | | | | | | | | | | | | | |
|---|---|---|---|---|---|---|---|---|---|---|---|---|---|---|---|
| Asp | Val | Gln | Asn | Glu | Glu | His | Leu | Ala | Ser | Leu | Ala | Gly | Arg | Val | Thr |
| | 65 | | | | | 70 | | | | 75 | | | | | |

| GAG | GCG | ATC | GGG | GCG | GGC | AAC | AAG | CTC | GAC | GGG | GTG | GTG | CAT | GCG | ATT | 1540 |
|---|---|---|---|---|---|---|---|---|---|---|---|---|---|---|---|---|
| Glu | Ala | Ile | Gly | Ala | Gly | Asn | Lys | Leu | Asp | Gly | Val | Val | His | Ala | Ile | |
| 80 | | | | | 85 | | | | | 90 | | | | | 95 | |

| GGG | TTC | ATG | CCG | CAG | ACC | GGG | ATG | GGC | ATC | AAC | CCG | TTC | TTC | GAC | GCG | 1588 |
|---|---|---|---|---|---|---|---|---|---|---|---|---|---|---|---|---|
| Gly | Phe | Met | Pro | Gln | Thr | Gly | Met | Gly | Ile | Asn | Pro | Phe | Phe | Asp | Ala | |
| | | | | 100 | | | | | 105 | | | | | | 110 | |

| CCC | TAC | GCG | GAT | GTG | TCC | AAG | GGC | ATC | CAC | ATC | TCG | GCG | TAT | TCG | TAT | 1636 |
|---|---|---|---|---|---|---|---|---|---|---|---|---|---|---|---|---|
| Pro | Tyr | Ala | Asp | Val | Ser | Lys | Gly | Ile | His | Ile | Ser | Ala | Tyr | Ser | Tyr | |
| | | | 115 | | | | | 120 | | | | | 125 | | | |

| GCT | TCG | ATG | GCC | AAG | GCG | CTG | CTG | CCG | ATC | ATG | AAC | CCC | GGA | GGT | TCC | 1684 |
|---|---|---|---|---|---|---|---|---|---|---|---|---|---|---|---|---|
| Ala | Ser | Met | Ala | Lys | Ala | Leu | Leu | Pro | Ile | Met | Asn | Pro | Gly | Gly | Ser | |
| | | 130 | | | | | 135 | | | | | 140 | | | | |

| ATC | GTC | GGC | ATG | GAC | TTC | GAC | CCG | AGC | CGG | GCG | ATG | CCG | GCC | TAC | AAC | 1732 |
|---|---|---|---|---|---|---|---|---|---|---|---|---|---|---|---|---|
| Ile | Val | Gly | Met | Asp | Phe | Asp | Pro | Ser | Arg | Ala | Met | Pro | Ala | Tyr | Asn | |
| | 145 | | | | | 150 | | | | | 155 | | | | | |

| TGG | ATG | ACG | GTC | GCC | AAG | AGC | GCG | TTG | GAG | TCG | GTC | AAC | AGG | TTC | GTG | 1780 |
|---|---|---|---|---|---|---|---|---|---|---|---|---|---|---|---|---|
| Trp | Met | Thr | Val | Ala | Lys | Ser | Ala | Leu | Glu | Ser | Val | Asn | Arg | Phe | Val | |
| 160 | | | | | 165 | | | | | 170 | | | | | 175 | |

| GCG | CGC | GAG | GCC | GGC | AAG | TAC | GGT | GTG | CGT | TCG | AAT | CTC | GTT | GCC | GCA | 1828 |
|---|---|---|---|---|---|---|---|---|---|---|---|---|---|---|---|---|
| Ala | Arg | Glu | Ala | Gly | Lys | Tyr | Gly | Val | Arg | Ser | Asn | Leu | Val | Ala | Ala | |
| | | | | 180 | | | | | 185 | | | | | 190 | | |

| GGC | CCT | ATC | CGG | ACG | CTG | GCG | ATG | AGT | GCG | ATC | GTC | GGC | GGT | GCG | CTC | 1876 |
|---|---|---|---|---|---|---|---|---|---|---|---|---|---|---|---|---|
| Gly | Pro | Ile | Arg | Thr | Leu | Ala | Met | Ser | Ala | Ile | Val | Gly | Gly | Ala | Leu | |
| | | | 195 | | | | | 200 | | | | | 205 | | | |

| GGC | GAG | GAG | GCC | GGC | GCC | CAG | ATC | CAG | CTG | CTC | GAG | GAG | GGC | TGG | GAT | 1924 |
|---|---|---|---|---|---|---|---|---|---|---|---|---|---|---|---|---|
| Gly | Glu | Glu | Ala | Gly | Ala | Gln | Ile | Gln | Leu | Leu | Glu | Glu | Gly | Trp | Asp | |
| | | 210 | | | | | 215 | | | | | 220 | | | | |

| CAG | CGC | GCT | CCG | ATC | GGC | TGG | AAC | ATG | AAG | GAT | GCG | ACG | CCG | GTC | GCC | 1972 |
|---|---|---|---|---|---|---|---|---|---|---|---|---|---|---|---|---|
| Gln | Arg | Ala | Pro | Ile | Gly | Trp | Asn | Met | Lys | Asp | Ala | Thr | Pro | Val | Ala | |
| | 225 | | | | | 230 | | | | | 235 | | | | | |

| AAG | ACG | GTG | TGC | GCG | CTG | CTG | TCT | GAC | TGG | CTG | CCG | GCG | ACC | ACG | GGT | 2020 |
|---|---|---|---|---|---|---|---|---|---|---|---|---|---|---|---|---|
| Lys | Thr | Val | Cys | Ala | Leu | Leu | Ser | Asp | Trp | Leu | Pro | Ala | Thr | Thr | Gly | |
| 240 | | | | | 245 | | | | | 250 | | | | | 255 | |

| GAC | ATC | ATC | TAC | GCC | GAC | GGC | GGC | GCG | CAC | ACC | CAA | TTG | CTC | | | 2062 |
|---|---|---|---|---|---|---|---|---|---|---|---|---|---|---|---|---|
| Asp | Ile | Ile | Tyr | Ala | Asp | Gly | Gly | Ala | His | Thr | Gln | Leu | Leu | | | |
| | | | | 260 | | | | | 265 | | | | | | | |

| TAGAACGCAT | GCAATTTGAT | GCCGTCCTGC | TGCTGTCGTT | CGGCGGACCG | GAAGGGCCCG | 2122 |
|---|---|---|---|---|---|---|
| AGCAGGTGCG | GCCGTTCCTG | GAGAACGTTA | CCCGGGGCCG | CGGTGTGCCT | GCCGAACGGT | 2182 |
| TGGACGCGGT | GGCCGAGCAC | TACCTGCATT | TCGGTGGGGT | ATCACCGATC | | 2232 |

(2) INFORMATION FOR SEQ ID NO:13:

(i) SEQUENCE CHARACTERISTICS:
        (A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO:13:

| Val | Thr | Ala | Thr | Ala | Thr | Glu | Gly | Ala | Lys | Pro | Pro | Phe | Val | Ser | Arg |
|---|---|---|---|---|---|---|---|---|---|---|---|---|---|---|---|
| 1 | | | | 5 | | | | | 10 | | | | | 15 | |

| Ser | Val | Leu | Val | Thr | Gly | Gly | Asn | Arg | Gly | Ile | Gly | Leu | Ala | Ile | Ala |
|---|---|---|---|---|---|---|---|---|---|---|---|---|---|---|---|
| | | | 20 | | | | | 25 | | | | | 30 | | |

| Gln | Arg | Leu | Ala | Ala | Asp | Gly | His | Lys | Val | Ala | Val | Thr | His | Arg | Gly |
|---|---|---|---|---|---|---|---|---|---|---|---|---|---|---|---|
| | | 35 | | | | | 40 | | | | | 45 | | | |

| Ser | Gly | Ala | Pro | Lys | Gly | Leu | Phe | Gly | Val | Glu | Cys | Asp | Val | Thr | Asp |
|---|---|---|---|---|---|---|---|---|---|---|---|---|---|---|---|
| | 50 | | | | | 55 | | | | | 60 | | | | |

```
Ser  Asp  Ala  Val  Asp  Arg  Ala  Phe  Thr  Ala  Val  Glu  Glu  His  Gln  Gly
 65             70                  75                  80

Pro  Val  Glu  Val  Leu  Val  Ser  Asn  Ala  Gly  Leu  Ser  Ala  Asp  Ala  Phe
                    85                  90                       95

Leu  Met  Arg  Met  Thr  Glu  Glu  Lys  Phe  Glu  Lys  Val  Ile  Asn  Ala  Asn
               100                 105                      110

Leu  Thr  Gly  Ala  Phe  Arg  Val  Ala  Gln  Arg  Ala  Ser  Arg  Ser  Met  Gln
          115                      120                      125

Arg  Asn  Lys  Phe  Gly  Arg  Met  Ile  Phe  Ile  Gly  Ser  Val  Ser  Gly  Ser
     130                      135                 140

Trp  Gly  Ile  Gly  Asn  Gln  Ala  Asn  Tyr  Ala  Ala  Ser  Lys  Ala  Gly  Val
145                 150                      155                           160

Ile  Gly  Met  Ala  Arg  Ser  Ile  Ala  Arg  Glu  Leu  Ser  Lys  Ala  Asn  Val
               165                      170                      175

Thr  Ala  Asn  Val  Val  Ala  Pro  Gly  Tyr  Ile  Asp  Thr  Asp  Met  Thr  Arg
               180                 185                      190

Ala  Leu  Asp  Glu  Arg  Ile  Gln  Gln  Gly  Ala  Leu  Gln  Phe  Ile  Pro  Ala
          195                      200                 205

Lys  Arg  Val  Gly  Thr  Pro  Ala  Glu  Val  Ala  Gly  Val  Val  Ser  Phe  Leu
     210                 215                      220

Ala  Ser  Glu  Asp  Ala  Ser  Tyr  Ile  Ser  Gly  Ala  Val  Ile  Pro  Val  Asp
225                      230                 235                           240

Gly  Gly  Met  Gly  Met  Gly  His
                    245
```

( 2 ) INFORMATION FOR SEQ ID NO:14:

( i ) SEQUENCE CHARACTERISTICS:
        ( A ) LENGTH: 269 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met  Thr  Gly  Leu  Leu  Asp  Gly  Lys  Arg  Ile  Leu  Val  Ser  Gly  Ile  Ile
 1              5                   10                  15

Thr  Asp  Ser  Ser  Ile  Ala  Phe  His  Ile  Ala  Arg  Val  Ala  Gln  Glu  Gln
               20                  25                       30

Gly  Ala  Gln  Leu  Val  Leu  Thr  Gly  Phe  Asp  Arg  Leu  Arg  Leu  Ile  Gln
          35                      40                       45

Arg  Ile  Thr  Asp  Arg  Leu  Pro  Ala  Lys  Ala  Pro  Leu  Leu  Glu  Leu  Asp
     50                       55                  60

Val  Gln  Asn  Glu  Glu  His  Leu  Ala  Ser  Leu  Ala  Gly  Arg  Val  Thr  Glu
 65                  70                      75                           80

Ala  Ile  Gly  Ala  Gly  Asn  Lys  Leu  Asp  Gly  Val  His  Ala  Ile  Gly
                    85                  90                       95

Phe  Met  Pro  Gln  Thr  Gly  Met  Gly  Ile  Asn  Pro  Phe  Phe  Asp  Ala  Pro
               100                 105                      110

Tyr  Ala  Asp  Val  Ser  Lys  Gly  Ile  His  Ile  Ser  Ala  Tyr  Ser  Tyr  Ala
          115                      120                      125

Ser  Met  Ala  Lys  Ala  Leu  Leu  Pro  Ile  Met  Asn  Pro  Gly  Gly  Ser  Ile
     130                      135                 140

Val  Gly  Met  Asp  Phe  Asp  Pro  Ser  Arg  Ala  Met  Pro  Ala  Tyr  Asn  Trp
145                 150                      155                           160

Met  Thr  Val  Ala  Lys  Ser  Ala  Leu  Glu  Ser  Val  Asn  Arg  Phe  Val  Ala
```

|     |     |     | 165 |     |     |     |     | 170 |     |     |     |     | 175 |     |     |
|-----|-----|-----|-----|-----|-----|-----|-----|-----|-----|-----|-----|-----|-----|-----|-----|
| Arg | Glu | Ala | Gly | Lys | Tyr | Gly | Val | Arg | Ser | Asn | Leu | Val | Ala | Ala | Gly |
|     |     |     | 180 |     |     |     |     | 185 |     |     |     |     | 190 |     |     |
| Pro | Ile | Arg | Thr | Leu | Ala | Met | Ser | Ala | Ile | Val | Gly | Gly | Ala | Leu | Gly |
|     |     | 195 |     |     |     |     | 200 |     |     |     |     | 205 |     |     |     |
| Glu | Glu | Ala | Gly | Ala | Gln | Ile | Gln | Leu | Leu | Glu | Glu | Gly | Trp | Asp | Gln |
|     | 210 |     |     |     |     | 215 |     |     |     |     | 220 |     |     |     |     |
| Arg | Ala | Pro | Ile | Gly | Trp | Asn | Met | Lys | Asp | Ala | Thr | Pro | Val | Ala | Lys |
| 225 |     |     |     |     | 230 |     |     |     |     | 235 |     |     |     |     | 240 |
| Thr | Val | Cys | Ala | Leu | Leu | Ser | Asp | Trp | Leu | Pro | Ala | Thr | Thr | Gly | Asp |
|     |     |     |     | 245 |     |     |     |     | 250 |     |     |     |     | 255 |     |
| Ile | Ile | Tyr | Ala | Asp | Gly | Gly | Ala | His | Thr | Gln | Leu | Leu |     |     |     |
|     |     |     | 260 |     |     |     |     | 265 |     |     |     |     |     |     |     |